(12) United States Patent
Lemoine et al.

(10) Patent No.: US 7,625,905 B2
(45) Date of Patent: Dec. 1, 2009

(54) OCTAHYDRO-PYRROLO[3,4-C]PYRROLE CCR5 RECEPTOR ANTAGONISTS

(75) Inventors: Remy Lemoine, San Francisco, CA (US); Chris Richard Melville, Palo Alto, CA (US); David Mark Rotstein, Sunnyvale, CA (US); Jutta Wanner, Mountain View, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/901,498

(22) Filed: Sep. 18, 2007

(65) Prior Publication Data

US 2008/0103125 A1    May 1, 2008

Related U.S. Application Data

(60) Provisional application No. 60/845,334, filed on Sep. 18, 2006.

(51) Int. Cl.
*A61K 31/4545* (2006.01)

(52) U.S. Cl. ............. 514/256; 514/210.18; 514/252.06; 514/255.05; 514/318; 514/322; 514/338; 514/406; 544/238; 544/333; 544/405; 548/364.7; 546/193; 546/199; 546/275.4; 546/276.7

(58) Field of Classification Search ........................ None
See application file for complete search history.

(56) References Cited

U.S. PATENT DOCUMENTS

2006/0014767 A1    1/2006   Lee et al.

2007/0191335 A1    8/2007   Lemoine et al.
2007/0191406 A1    8/2007   Lemoine et al.

FOREIGN PATENT DOCUMENTS

| WO | WO 2004/054974 A2 | 7/2004 |
|---|---|---|
| WO | WO 2004/054974 A3 | 7/2004 |
| WO | WO 2004/055016 A1 | 7/2004 |
| WO | WO 2005/009959 A1 | 2/2005 |
| WO | WO 2005/101989 A2 | 11/2005 |
| WO | WO 2005/101989 A3 | 11/2005 |
| WO | WO 2006/001751 A1 | 1/2006 |
| WO | WO 2006/067385 A1 | 6/2006 |

*Primary Examiner*—Kamal A Saeed
*Assistant Examiner*—Valerie Rodriguez-Garcia
(74) *Attorney, Agent, or Firm*—Brian L. Buckwalter

(57) ABSTRACT

Chemokine receptor antagonists, in particular, 3,7-diazabicyclo[3.3.0]octane compounds according to formula (I) wherein $R^1$-$R^3$ and Ar are as defined herein are antagonists of chemokine CCR5 receptors which are useful for treating or preventing an human immunodeficiency virus (HIV) infection, or treating AIDS or ARC. The invention further provides methods for treating diseases that are alleviated with CCR5 antagonists. The invention includes pharmaceutical compositions and methods of using the compounds for the treatment of these diseases. The invention further includes processes for the preparation of compounds according to formula I.

(I)

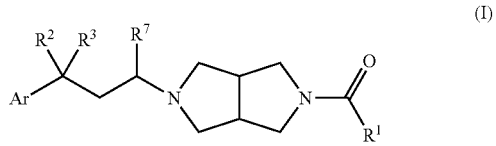

11 Claims, No Drawings

US 7,625,905 B2

OCTAHYDRO-PYRROLO[3,4-C]PYRROLE CCR5 RECEPTOR ANTAGONISTS

CROSS REFERENCE TO PRIOR APPLICATIONS

This application is claims benefit of U.S. Provisional Application No. 60/845,334, filed Sep. 18, 2006, which is hereby incorporated by reference in its entirety.

FIELD OF THE INVENTION

This invention relates to octahydro-pyrrolo[3,4-c]pyrrole derivatives useful in the treatment of a variety of disorders, including those in which the modulation of CCR5 receptors is desirable. More particularly, the present invention relates to (4,6-dimethyl-pyrimidin-5-yl)-[5-(3-phenyl-propyl)-hexahydro-pyrrolo[3,4-c]pyrrol-2-yl]-methanone compounds and related derivatives more fully described herein, to compositions containing, to uses of such derivatives and to processes for preparing said compounds. Disorders that may be treated or prevented by the present derivatives include HIV and HIV-mediated retroviral infections (and the resulting acquired immune deficiency syndrome, AIDS), diseases of the immune system and inflammatory diseases.

BACKGROUND OF THE INVENTION

A-M. Vandamme et al. (Antiviral Chemistry & Chemotherapy, 1998 9:187-203) describe current HAART clinical treatments of HIV-1 infections in man including triple drug combinations. Highly active anti-retroviral therapy (HAART) has traditionally consisted of combination therapy with nucleoside reverse transcriptase inhibitors (NRTI), non-nucleoside reverse transcriptase inhibitors (NNRTI) and protease inhibitors (PI). These compounds inhibit biochemical processes required for viral replication. In compliant drug-naive patients, HAART is effective in reducing mortality and progression of HIV-1 to AIDS. While HAART has dramatically altered the prognosis for HIV infected persons, there remain many drawbacks to the current therapy including highly complex dosing regimes and side effects which can be very severe (A. Carr and D. A. Cooper, Lancet 2000 356 (9239):1423-1430). Moreover, these multidrug therapies do not eliminate HIV-1 and long-term treatment usually results in multidrug resistance, thus limiting their utility in long term therapy. Development of new drug therapies to provide better HIV-1 treatment remains a priority.

The chemokines, a subset of the cytokine family of soluble immune modulators, are a large family of pro-inflammatory peptides that exert their pharmacological effect through G-protein-coupled receptors. The name "chemokine", is a contraction of "chemotactic cytokines". The chemokines are leukocyte chemotactic proteins capable of attracting leukocytes to various tissues, which is an essential response to inflammation and infection. Human chemokines include approximately 50 structurally homologous small proteins comprising 50-120 amino acids. (M. Baggiolini et al., Ann. Rev. Immunol. 1997 15:675-705) The CCR5 receptor is one member of this family.

Chemokine receptors are seven membrane-spanning receptors that signal through heterotrimeric G protein when bound to an agonist. Human CCR5 is composed of 352 amino acids with an intra-cellular C-terminus containing structural motifs for G-protein association and ligand-dependent signaling (M. Oppermann Cellular Signaling 2004 16:1201-1210). The extracellular N-terminal domain contributes to high-affinity chemokine binding and interactions with the gp120 HIV protein (T. Dragic J. Gen. Virol. 2001 82:1807-1814; C. Blanpain et al. J. Biol. Chem. 1999 274:34719-34727). The natural ligands for the CCR5 are the macrophage inflammatory proteins (MIP) designated MIP-1a and MIP-1b and RANTES. The binding site for RANTES (Regulated upon Activation and is Normal T-cell Expressed and Secreted) has been shown to be on the N-terminal domain and HIV gp120 has been suggested to interact initially with the N-terminal domain and also with the ECL2 (extra-cellular loop 2). (B. Lee, et al. J. Biol. Chem. 1999 274:9617-26)

Modulators of the CCR5 receptor may be useful in the treatment of various inflammatory diseases and conditions, and in the treatment of infection by HIV-1 and genetically related retroviruses. As leukocyte chemotactic factors, chemokines play an indispensable role in the attraction of leukocytes to various tissues of the body, a process which is essential for both inflammation and the body's response to infection. Because chemokines and their receptors are central to the pathophysiology of inflammatory, autoimmune and infectious diseases, agents which are active in modulating, preferably antagonizing, the activity of chemokines and their receptors, are useful in the therapeutic treatment of these diseases. The CCR5 receptor is of particular importance in the context of treating inflammatory and infectious diseases.

HIV-1 infects cells of the monocyte-macrophage lineage and helper T-cell lymphocytes by exploiting a high affinity interaction of the viral enveloped glycoprotein (Env) with the CD4 antigen. The CD4 antigen, however, appeared to be a necessary, but not sufficient requirement for cell entry and at least one other surface protein was required to infect the cells (E. A. Berger et al., Ann. Rev. Immunol. 1999 17:657-700). Two chemokine receptors, either the CCR5 (M-trophic strains) or the CXCR4 (T-trophic strains) receptor were subsequently found to be co-receptors which are required, along with CD4, for infection of cells by the human immunodeficiency virus (HIV). The central role of CCR5 in the pathogenesis of HIV was inferred by epidemiological identification of powerful disease modifying effects of the naturally occurring null allele CCR5 Δ32. The Δ32 mutation has a 32-base pair deletion in the CCR5 gene resulting in a truncated protein designated Δ32. Relative to the general population, Δ32/Δ32 homozygotes are significantly common in exposed/uninfected individuals suggesting the role of CCR5 in HIV cell entry (R. Liu et al., Cell 1996 86(3):367-377; M. Samson et al., Nature 1996 382(6593):722-725).

The HIV-1 envelope protein is comprised of two subunits: gp120, the surface subunit and gp41, the transmembrane subunit. The two subunits are non-covalently associated and form homotrimers which compose the HIV envelope. Each gp41 subunit contains two helical heptad repeat regions, HR1 and HR2 and a hydrophobic fusion region on the C-terminus.

Viral fusion and cell entry is a complex multi-step process and each step affords the potential for therapeutic intervention. The CD4 binding site on the gp120 of HIV appears to first interact with the CD4 molecule on the cell surface inducing a conformation change in gp120 which creates or exposes a cryptic CCR5 (or CXCR4) binding site, and undergoes conformational changes which permits binding of gp120 to the CCR5 and/or CXCR4 cell-surface receptor. The bivalent interaction brings the virus membrane into close proximity with the target cell membrane and the hydrophobic fusion region can insert into the target cell membrane. A conformation change in gp41 creates a contact between the outer leaflet of the target cell membrane and the viral membrane which produces a fusion pore whereby viral core containing genomic RNA enters the cytoplasm. The conformational changes induced by these steps expose additional targets for chemotherapeutic intervention. Each of these steps affords an opportunity for therapeutic intervention in preventing or slowing HIV infection.

Small molecules (Q. Guo et al. *J. Virol.* 2003 77:10528-63) and antibodies (D. R. Kuritzkes et al. 10th *Conference on Retroviruses and Opportunistic Infections*, Feb. 10-14, 2003, Boston, Mass. Abstract 13; K. A. Nagashima et al. *J. Infect. Dis.* 2001 183:1121-25) designed to prevent the gp120/CD4 interaction have been disclosed. Small molecule antagonists of, and antibodies to, CCR5 are discussed below. A small molecular weight antagonist of CXCR4 has been explored (J. Blanco et al. *Antimicrob. Agents Chemother.* 2000 46:1336-39). Enfuvirtide (T20, ENF or FUZEON®) is a 36 amino acid peptide corresponding to residues 643-678 in the HR2 domain of gp41. Enfuvirtide binds to the trimeric coiled-coil by the HR1 domains and acts in a dominant negative manner to block the endogenous six helix bundle formation thus inhibiting viral fusion. (J. M. Kilby et al., *New Eng. J. Med.* 1998 4(11):1302-1307). Enfuvirtide has been approved for clinical use.

Potential CCR5 antagonists have been reviewed. (A. Palani and J. R. Tagat, "Discovery and Development of Small-Molecule Chemokine Coreceptor CCR5 Antagonists" *J. Med. Chem.* 2006 49(10):2851-2857; J. D. Reeves and A. J. Piefer, "Emerging Drug Targets for Antiviral Therapy" *Drugs* 2005 65(13):1747-1766; M. Westby and E. van der Ryst, "CCR5 antagonists: Host-targeted antivirals for the treatment of HIV infection" *Antiviral Chem. Chemother.* 2005 16(6):339-354; B. Juelg and F.-D., "CCR5 antagonists: a new tool in fighting HIV" *J. HIV Ther. Current Trends* 2005 10(4):68-71).

Takeda identified TAK-779 as a potential CCR5 antagonist. (M. Shiraishi et al., *J. Med. Chem.* 2000 43(10):2049-2063; M. Babba et al. *Proc. Nat. Acad. Sci. USA* 1999 96:5698-5703) and TAK-220 (C. Tremblay et al. *Antimicrob. Agents Chemother.* 2005 49(8):3483-3485). WO0039125 (D. R. Armour et al.) and WO0190106 (M. Perros et al.) disclose heterocyclic compounds that are potent and selective CCR5 antagonists. Pfizer has received FDA approval to market miraviroc (UK-427,857; SELZENTRY®, CELZENTRY®) for treatment of HIV-1 infections and AIDS (P. Dorr et al., *Antimicrob. Agents Chemother.* 2005 49(11):4721-4732; A. Wood and D. Armour, *Prog. Med. Chem.* 2005 43:239-271; C. Watson et al., *Mol. Pharm.* 2005 67(4):1268-1282; M. J. Macartney et al., 43rd *Intersci. Conf. Antimicrob. Agents Chemother.* Sep. 14-17, 2003, Abstract H-875). Schering has advanced Sch-351125 (SCH-C) into Phase I/II clinical studies and reported the advance of a more potent follow-up compound, Vicroviroc (Sch-417690, SCH-D) into Phase I studies (S. W. McCrombie et al., WO00066559; B. M. Baroudy et al. WO00066558; A. Palani et al., *J. Med. Chem.* 2001 44(21):3339-3342; J. R. Tagat et al., *J. Med. Chem.* 2001 44(21):3343-3346; J. A. Esté, *Cur. Opin. Invest. Drugs* 2002 3(3):379-383; J. M. Struzki et al. *Proc. Nat. Acad. Sci. USA* 2001 98:12718-12723). Merck has disclosed the preparation of (2S)-2-(3-chlorophenyl)-1-N-(methyl)-N-(phenyl-sulfonyl)amino]-4-[spiro(2,3-dihydrobenzothiophene-3,4'-piperidin-1'-yl)butane S-oxide and related derivatives with good affinity for the CCR5 receptor and potent-HIV activity. (P. E. Finke et al., *Bioorg. Med. Chem. Lett.*, 2001 11:265-270; P. E. Finke et al., *Bioorg. Med. Chem. Lett.*, 2001 11:2469-2475; P. E. Finke et al., *Bioorg. Med. Chem. Lett.*, 2001 11:2475-2479; J. J. Hale et al., *Bioorg. Med. Chem. Lett.*, 2001 11:2741-22745; D. Kim et al., *Bioorg. Med. Chem. Lett.*, 2001 11:3099-3102) C. L. Lynch et al. *Org. Lett.* 2003 5:2473-2475; R. S. Veazey et al. *J. Exp. Med.* 2003 198: 1551-1562. GSK-873140 (ONO-4128, E-913, AK-602) was identified in a program initiated at Kumamoto University (K. Maeda et al. *J. Biol. Chem.* 2001 276:35194-35200; H. Nakata et al. *J. Virol.* 2005 79(4):2087-2096) and has been advanced to clinical trials. In WO2004/054974 published Jul. 1, 2004 and in WO2004/055016 published Jul. 1, 2004, W. M. Kazmierski et al. disclose CCR5 antagonists. In WO00/166525; WO00/187839; WO02/076948; WO02/076948; WO02/079156, WO2002070749, WO2003080574, WO2003042178, WO2004056773, WO2004018425 and WO2006/001751 AstraZeneca disclose 4-amino piperidine compounds which are CCR5 antagonists.

In U.S. Publication No. 20050176703 published Aug. 11, 2005, S. D. Gabriel and D. M. Rotstein disclosed heterocyclic CCR5 antagonist capable of prevent HIV cell entry. Related octahydro-pyrrolo[3,4-c]pyrrole compounds which are antagonists of the CCR5 receptor have been disclosed in Assignee's copending non-provisional application US 20060014767 filed Jun. 8, 2005 (WO 2005121145, published Dec. 22, 2005) entitled Heterocyclic Antiviral Compounds, in the names of E. K. Lee et al. published Dec. 22, 2005; U.S. Ser. No. 11/706,807, filed Feb. 15, 2007, entitled Heterocyclic Antiviral Compounds in the names of R. Lemoine et al.; and U.S. Ser. No. 11/706,728, filed Feb. 15, 2007, entitled Heterocyclic Antiviral Compounds in the names of R. Lemoine et al. which are all hereby incorporated by reference in their entirety. In addition to the potential for CCR5 modulators in the management of HIV infections, the CCR5 receptor is an important regulator of immune function and compounds of the present invention may prove valuable in the treatment of disorders of the immune system. Treatment of solid organ transplant rejection, graft v. host disease, arthritis, rheumatoid arthritis, inflammatory bowel disease, atopic dermatitis, psoriasis, asthma, allergies or multiple sclerosis by administering to a human in need of such treatment an effective amount of a CCR5 antagonist compound of the present invention is also possible. (M. A. Cascieri and M. S. Springer, *Curr. Opin. Chem. Biol.* 2000 4:420-427; A. Proudfoot et al., *Immunol. Rev.* 2000 177:246-256; P. Houshmand and A. Zlotnik, *Curr. Opin. Chem. Biol.* 2003 7:457-460)

SUMMARY OF THE INVENTION

The present invention relates to a compounds according to formula I which are CCR5 receptor antagonists, methods for treating an HIV-1 infection, or preventing an HIV-1 infection, or treating AIDS or ARC, or inflammatory or autoimmune diseases alleviated by administration of a compound according to formula I and pharmaceutical compositions for treating diseases containing a compound according to formula I admixed with at least one carrier, diluent or excipient,

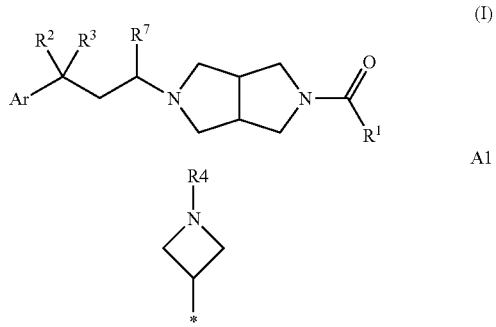

-continued

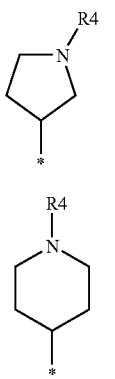

wherein $R^1$ is selected from the group consisting of (a) phenyl, (b) pyridinyl, (c) pyrimidinyl, each optionally substituted with $C_{1-6}$ alkyl, $C_{1-6}$ haloalkyl, $C_{1-6}$ alkoxy, hydroxy, cyano, $NHSO_2C_{1-6}$ alkyl, $SO_2NR^{9a}R^{10a}$, —$NR^{9b}R^{10b}$, and halogen, and (d) B1

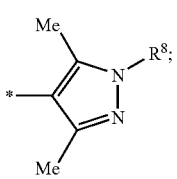

wherein $R^8$ is $C_{3-7}$ cycloalkyl, phenyl or heteroaryl selected from the group consisting of pyridine, pyrimidine, pyrazine and pyridazine said heteroaryl or said phenyl optionally substituted with $C_{1-3}$ alkyl or $C_{1-3}$ haloalkyl;

One of $R^2$ and $R^3$ is hydrogen and the other of $R^2$ and $R^3$ is A1, A2 or A3, or $R^2$ and $R^3$ together are $(CH_2)_m NR^4 (CH_2)_n$;

$R^4$ is $C_{1-6}$ alkyl, $C_{1-6}$ haloalkyl, $CH_2C{\equiv}N$, —$C({=}O)R^5$ or —$SO_2R^5$;

$R^5$ is (a) $C_{1-6}$ alkyl, (b) $C_{3-6}$ cycloalkyl optionally independently substituted with one or two $C_{1-6}$ alkyl, halogen, hydroxy, cyano, oxo or $C_{1-6}$ haloalkyl, (c) $C_{1-6}$ haloalkyl, (d) $C_{1-6}$ hydroxyalkyl, (e) $C_{1-3}$ alkoxy-$C_{1-3}$ alkyl, (f) $C_{3-6}$ cycloalkyl-$C_{1-6}$ alkyl, (g) $C_{1-6}$ alkoxy, (h) amino, (i) $C_{1-6}$ alkylamino, (j) di-$C_{1-6}$ alkylamino (k) $C_{3-6}$ cycloalkylamino, (l) phenyl-$C_{1-3}$ alkyl or (m) phenyl said phenyl optionally substituted with one to three groups independently selected in each occurrence form the group consisting of $C_{1-6}$ alkyl, $C_{1-6}$ alkoxy, halogen, —$SO_2NR^{6a}R^{6b}$ and —$NHSO_2C_{1-6}$ alkyl; (n) tetrahydropyranyl, (o) tetrahydrofuranyl; (p) cycloalkoxy optionally independently substituted with one or two halogen, hydroxy or oxo, (q) $C_{4-6}$ cycloalkyl-amino, (r) tetrahydropyranyl-methyl, (s) pyridinyl or (t) cyanomethyl;

$R^{6a}$ and $R^{6b}$ are independently hydrogen, $C_{1-6}$ alkyl or $C_{1-6}$ acyl;

$R^7$ is hydrogen or $C_{1-3}$ alkyl;

$R^{9a}$ and $R^{10a}$ (i) taken independently, one of $R^{9a}$ and $R^{10a}$ is hydrogen or $C_{1-6}$ alkyl and the other of $R^{9a}$ and $R^{10a}$ is selected from the group consisting of hydrogen, $C_{1-6}$ alkyl and —$C({=}O)R^7$;

(ii) taken together with the nitrogen atom to which they are attached form an azetidine, pyrrolidine, piperidine or azepine ring said azetidine, pyrrolidine, piperidine or azepine ring optionally substituted with hydroxy, amino, $C_{1-3}$ alkylamine or $C_{1-3}$ dialkylamine; or, (iii) taken together are $(CH_2)_2$—X—$(CH_2)_2$;

$R^{9b}$ is defined as $R^{9a}$ and $R^{10b}$ is defined as $R^{10a}$;

$R^{11}$ is hydrogen, $C_{1-6}$ alkyl or $C_{1-6}$ acyl;

X is O, $S(O)_p$ or $NR^{11}$ wherein p is an integer from 0 to 2;

Ar is phenyl optionally substituted with one to three substituents independently selected in each occurrence from the group consisting of halogen, $C_{1-6}$ alkyl, $C_{1-6}$ alkoxy, cyano and nitro;

m and n are independently one or two; or, pharmaceutically acceptable salts thereof.

The present invention further provides for a method for treating an HIV-1 infection, or preventing an HIV-1 infection, or treating AIDS or ARC which consists of co-administering compounds according to formula I and one or more other agents beneficial in treating or preventing an HIV-infection or preventing the progression of the disease. The present invention further provides for a method for treating inflammatory and autoimmune diseases associated with abnormal levels of leukocyte activity. Such inflammatory/autoimmune diseases include rheumatoid arthritis and asthma. The CCR5 antagonists described herein would also be useful in management of organ or tissue transplant rejection.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

The symbols "*" at the end of a bond or "------" drawn through a bond each refer to the point of attachment of a functional group or other chemical moiety to the rest of the molecule of which it is a part. Thus, for example:

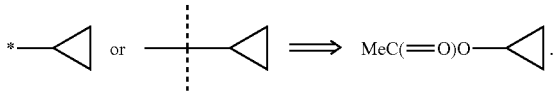

A bond drawn into ring system (as opposed to connected at a distinct vertex) indicates that the bond may be attached to any of the suitable ring atoms.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

In one embodiment of the present invention there is provided a compound according to formula I wherein $R^1$, $R^2$, $R^3$, $R^4$, $R^5$, $R^{6a}$, $R^{6b}$, $R^7$, $R^8$, $R^{9a}$, $R^{9b}$, $R^{10a}$, $R^{10b}$, $R^{11}$, A1, A2, A3, $B^1$, Ar, X, m, n and p are as defined herein above. The phrase "as defined herein above" refers to the broadest definition for each group as provided in the Summary of the Invention. In other embodiments provided below, substituents present in each embodiment which are not explicitly defined retain the broadest definition provided in the Summary of the Invention.

In another embodiment of the present invention there is provided a compound according to formula I wherein Ar is phenyl optionally substituted with one to three halogen substituents and, and $R^1$, $R^2$, $R^3$, $R^4$, $R^5$, $R^{6a}$, $R^{6b}$, $R^7$, $R^8$, $R^{9a}$, $R^{9b}$, $R^{10a}$, $R^{10b}$, $R^{11}$, A1, A2, A3, B1, X, m, n and p are as defined herein above.

In a second embodiment of the present invention there is provided a compound according to formula I wherein $R^1$ is selected from the group consisting of phenyl, pyridinyl and pyrimidinyl optionally substituted with $C_{1-6}$ alkyl, $C_{1-6}$ haloalkyl, $C_{1-6}$ alkoxy, hydroxy, cyano and halogen; one of $R^2$ and $R^3$ is hydrogen and the other of $R^2$ and $R^3$ is A1, A2 or A3, or $R^2$ and $R^3$ together are $(CH_2)_mNR^4(CH_2)_n$; $R^4$ is $C_{1-6}$ alkyl, $C_{1-6}$ haloalkyl, $CH_2C\equiv N$, —C(=O)$R^5$ or —SO$_2R^5$; $R^5$ is (a) $C_{1-6}$ alkyl, (b) $C_{3-6}$ cycloalkyl optionally independently substituted with one or two $C_{1-6}$ alkyl, halogen, hydroxy, cyano, oxo or $C_{1-6}$ haloalkyl, (c) $C_{1-6}$ haloalkyl, (d) $C_{1-6}$ hydroxyalkyl, (e) $C_{1-3}$ alkoxy-$C_{1-3}$ alkyl, (f) $C_{3-6}$ cycloalkyl-$C_{1-6}$ alkyl, (g) $C_{1-6}$ alkoxy, (h) amino, (i) $C_{1-6}$ alkylamino, (j) di-$C_{1-6}$ alkylamino (k) $C_{3-6}$ cycloalkylamino, (l) phenyl-$C_{1-3}$ alkyl or (m) phenyl said phenyl optionally substituted with one to three groups independently selected in each occurrence form the group consisting of $C_{1-6}$ alkyl, $C_{1-6}$ alkoxy, halogen, —SO$_2NR^{6a}R^{6b}$ and —NHSO$_2C_{1-6}$ alkyl; (n) tetrahydropyranyl, (o) tetrahydrofuranyl; (p) cycloalkoxy optionally independently substituted with one or two halogen, hydroxy or oxo, (q) $C_{4-6}$ cycloalkyl-amino, (r) tetrahydropyranyl-methyl, (s) pyridinyl or (t) cyanomethyl; $R^{6a}$ and $R^{6b}$ are independently hydrogen, $C_{1-6}$ alkyl or $C_{1-6}$ acyl; Ar is phenyl optionally substituted with one to three substituents independently selected in each occurrence from the group consisting of halogen, $C_{1-6}$ alkyl, $C_{1-6}$ alkoxy, cyano and nitro; m and n are independently one or two; or, pharmaceutically acceptable salts thereof.

In another embodiment of the present invention there is provided a compound according to formula I wherein $R^1$ is selected from the group consisting of phenyl, pyridinyl and pyrimidinyl optionally substituted with $C_{1-6}$ alkyl, $C_{1-6}$ haloalkyl, $C_{1-6}$ alkoxy, hydroxy, cyano and halogen; one of $R^2$ and $R^3$ is hydrogen and the other of $R^2$ and $R^3$ is A1, A2 or A3, or $R^2$ and $R^3$ together are $(CH_2)_mNR^4(CH_2)_n$; $R^4$ is $C_{1-6}$ alkyl, $C_{1-6}$ haloalkyl, $CH_2C\equiv N$, —C(=O)$R^5$ or —SO$_2R^5$; $R^5$ is (a) $C_{1-6}$ alkyl, (b) $C_{3-6}$ cycloalkyl optionally independently substituted with one or two $C_{1-6}$ alkyl, halogen, hydroxy, cyano, oxo or $C_{1-6}$ haloalkyl, (c) $C_{1-6}$ haloalkyl, (d) $C_{1-6}$ hydroxyalkyl, (e) $C_{1-3}$ alkoxy-$C_{1-3}$ alkyl, (f) $C_{3-6}$ cycloalkyl-$C_{1-6}$ alkyl, (g) $C_{1-6}$ alkoxy, (h) amino, (i) $C_{1-6}$ alkylamino, (j) di-$C_{1-6}$ alkylamino (k) $C_{3-6}$ cycloalkylamino, (l) phenyl-$C_{1-3}$ alkyl or (m) phenyl said phenyl optionally substituted with one to three groups independently selected in each occurrence form the group consisting of $C_{1-6}$ alkyl, $C_{1-6}$ alkoxy, halogen, —SO$_2NR^{6a}R^{6b}$ and —NHSO$_2C_{1-6}$ alkyl; (n) tetrahydropyranyl, (o) tetrahydrofuranyl; (p) cycloalkoxy optionally independently substituted with one or two halogen, hydroxy or oxo, (q) $C_{4-6}$ cycloalkyl-amino, (r) tetrahydropyranyl-methyl, (s) pyridinyl or (t) cyanomethyl; $R^{6a}$ and $R^{6b}$ are independently hydrogen, $C_{1-6}$ alkyl or $C_{1-6}$ acyl; Ar is phenyl optionally substituted with one to three halogen substituents; and, m and n are independently one or two; or, pharmaceutically acceptable salts thereof.

In another embodiment of the present invention there is provided a compound according to formula I wherein $R^1$ is 2,4-dimethyl-pyridin-3-yl, 2,4-dimethyl-6-cyano-pyridin-3-yl, 4,6-dimethyl-pyridin-5-yl, 4,6-dimethyl-2-trifluoromethyl-pyrimidin-5-yl; one of $R^2$ and $R^3$ is hydrogen and the other of $R^2$ and $R^3$ is A1, A2 or A3, or $R^2$ and $R^3$ together are $(CH_2)_mNR^4(CH_2)_n$; $R^4$ is $C_{1-6}$ alkyl, $C_{1-6}$ haloalkyl, $CH_2C\equiv N$, —C(=O)$R^5$ or —SO$_2R^5$; $R^5$ is (a) $C_{1-6}$ alkyl, (b) $C_{3-6}$ cycloalkyl optionally independently substituted with one or two $C_{1-6}$ alkyl, halogen, hydroxy, cyano, oxo or $C_{1-6}$ haloalkyl, (c) $C_{1-6}$ haloalkyl, (d) $C_{1-6}$ hydroxyalkyl, (e) $C_{1-3}$ alkoxy-$C_{1-3}$ alkyl, (f) $C_{3-6}$ cycloalkyl-$C_{1-6}$ alkyl, (g) $C_{1-6}$ alkoxy, (h) amino, (i) $C_{1-6}$ alkylamino, (j) di-$C_{1-6}$ alkylamino (k) $C_{3-6}$ cycloalkylamino, (l) phenyl-$C_{1-3}$ alkyl or (m) phenyl said phenyl optionally substituted with one to three groups independently selected in each occurrence form the group consisting of $C_{1-6}$ alkyl, $C_{1-6}$ alkoxy, halogen, —SO$_2NR^{6a}R^{6b}$ and —NHSO$_2C_{1-6}$ alkyl; (n) tetrahydropyranyl, (o) tetrahydrofuranyl; (p) cycloalkoxy optionally independently substituted with one or two halogen, hydroxy or oxo, (q) $C_{4-6}$ cycloalkyl-amino, (r) tetrahydropyranyl-methyl, (s) pyridinyl or (t) cyanomethyl; $R^{6a}$ and $R^{6b}$ are independently hydrogen, $C_{1-6}$ alkyl or $C_{1-6}$ acyl; Ar is phenyl optionally substituted with one to three halogen substituents; and, m and n are independently one or two; or, pharmaceutically acceptable salts thereof.

In a third embodiment of the present invention there is provided a compound according to formula I wherein $R^1$ is 2,6-dimethylphenyl, 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl; $R^2$ is A3; $R^3$ is hydrogen; $R^4$ is —C(=O)$R^5$ or —SO$_2R^5$; Ar is phenyl optionally substituted with one to three halogens; and $R^5$, $R^6$, $R^{6a}$, A3, m and n are as defined herein above or pharmaceutically acceptable salts thereof.

In a fourth embodiment of the present invention there is provided a compound according to formula I wherein $R^1$ is 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl; $R^2$ is A3; $R^3$ is hydrogen; $R^4$ is —SO$_2$R$^5$; $R^5$ is (a) $C_{1-6}$ alkyl, (b) $C_{3-6}$ cycloalkyl optionally substituted with one or two groups independently selected in each occurrence from the group consisting of hydroxyl, halogen, $C_{1-6}$ alkyl, $C_{1-6}$ haloalkyl and oxo, (c) optionally substituted phenyl or (d) optionally substituted phenyl-$C_{1-3}$ alkyl; Ar is phenyl optionally substituted with one to three halogens; and $R^{6a}$, $R^{6b}$, A3, m and n are as defined herein above, or pharmaceutically acceptable salts thereof.

In fifth embodiment of the present invention there is provided a compound according to formula I wherein $R^1$ is 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl; $R^2$ is A3; $R^3$ is hydrogen; $R^4$ is —CO$_2$R$^5$; $R^5$ is (a) $C_{1-6}$ alkyl, (b) $C_{1-6}$ alkoxy, (c) $C_{1-6}$ hydroxyalkyl, (d) $C_{3-6}$ cycloalkyl optionally substituted with one or two groups independently selected in each occurrence from the group consisting of hydroxyl, halogen, $C_{1-6}$ alkyl, $C_{1-6}$ haloalkyl and oxo, or (e) $C_{1-3}$ alkoxy-$C_{1-3}$ alkyl; and Ar is phenyl optionally substituted with one to three halogens; and $R^{6i}$, $R^{6b}$, A3, m and n are as defined herein above, or pharmaceutically acceptable salts thereof.

In sixth another embodiment of the present invention there is provided a compound according to formula I wherein $R^1$ is 2,6-dimethylphenyl, 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl; $R^2$ is A1 or A2; $R^3$ is hydrogen; $R^4$ is —C(=O)R$^5$ or —SO$_2$R$^5$; Ar is phenyl optionally substituted with one to three halogens; and $R^5$, $R^{6a}$, $R^{6b}$, A1, A2, m and n are as defined herein above or pharmaceutically acceptable salts thereof.

In a seventh embodiment of the present invention there is provided a compound according to formula I wherein $R^1$ is 2,6-dimethylphenyl, 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl; $R^2$ and $R^3$ together are $(CH_2)_m NR^4(CH_2)_n$; $R^4$ is —C(=O)R$^5$ or —SO$_2$R$^5$; Ar is phenyl optionally substituted with one to three halogens; and $R^5$, $R^{6a}$, $R^{6b}$, m and n are as defined herein above or pharmaceutically acceptable salts thereof.

In another embodiment of the present invention there is provided a compound according to formula I wherein $R^1$ is 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl; $R^2$ and $R^3$ together are $(CH_2)_m NR^4 (CH_2)_n$; $R^4$ is —C(=O)R$^5$ or —SO$_2$R$^5$; Ar is phenyl optionally substituted with one to three halogens; and $R^5$, $R^{6a}$, $R^{6b}$, m and n are as defined herein above or pharmaceutically acceptable salts thereof.

In an eighth embodiment of the present invention there is provided a compound according to formula I wherein $R^1$ is 2,6-dimethylphenyl, 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl; $R^2$ and $R^3$ together are $(CH_2)_m NR^4(CH_2)_n$; m and n are one; $R^4$ is —C(=O)R$^5$ or —SO$_2$R$^5$; Ar is phenyl optionally substituted with one to three halogens; $R^5$ is (a) $C_{1-6}$ alkyl, (b) $C_{1-6}$ haloalkyl, (c) $C_{3-6}$ cycloalkyl optionally independently substituted with one or two $C_{1-6}$ alkyl, halogen, hydroxy, cyano, oxo or $C_{1-6}$ haloalkyl, (d) tetrahydropyranyl, (e) tetrahydrofuranyl, $R^{6a}$, $R^{6b}$ are as defined herein above or pharmaceutically acceptable salts thereof.

In a ninth embodiment of the present invention there is provided a compound according to formula I wherein $R^1$ is 2,6-dimethylphenyl, 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl; $R^2$ and $R^3$ together are $(CH_2)_m NR^4(CH_2)_n$; $R^4$ is $C_{1-6}$ alkyl or $C_{1-6}$ haloalkyl; Ar is phenyl optionally substituted with one to three halogens; and $R^5$, $R^{6a}$, $R^{6b}$, m and n are as defined herein above or pharmaceutically acceptable salts thereof.

In a tenth embodiment of the present invention there is provided a compound according to formula I which compound is a free base or a pharmaceutically acceptable salt form of compounds I-1 to I-45 of TABLE I, compounds II-1 to II-40 of TABLE II, compounds III-1 to III-12 of TABLE III, compounds IV-1 to IV-20 of TABLE IV, or compounds V-1 to V-31 of TABLE V.

In an eleventh embodiment of the present invention there is provided a method for treating an HIV-1 infection, or preventing an HIV-1 infection, or treating AIDS or ARC, comprising administering to a host in need thereof a therapeutically effective amount of a compound according to formula I wherein $R^1$, $R^2$, $R^3$, $R^4$, $R^5$, $R^{6a}$, $R^{6b}$, $R^7$, $R^8$, $R^{9a}$, $R^{9b}$, $R^{10a}$, $R^{10b}$, $R^{11}$, A1, A2, A3, B1, Ar, X, m, n and p are as defined herein above, or pharmaceutically acceptable salts thereof.

In still another embodiment of the present invention there is provided a method for treating an HIV-1 infection, or preventing an HIV-1 infection, or treating AIDS or ARC, comprising administering to a host in need thereof a therapeutically effective amount of a compound according to formula I wherein $R^1$ is selected from the group consisting of phenyl, pyridinyl and pyrimidinyl optionally substituted with $C_{1-6}$ alkyl, $C_{1-6}$ haloalkyl, $C_{1-6}$ alkoxy, hydroxy, cyano and halogen; one of $R^2$ and $R^3$ is hydrogen and the other of $R^2$ and $R^3$ is A1, A2 or A3, or $R^2$ and $R^3$ together are $(CH_2)_m NR^4 (CH_2)_n$; $R^4$ is $C_{1-6}$ alkyl, $C_{1-6}$ haloalkyl, CH$_2$C≡N, —C(=O)R$^5$ or —SO$_2$R$^5$; $R^5$ is (a) $C_{1-6}$ alkyl, (b) $C_{3-6}$ cycloalkyl optionally independently substituted with one or two $C_{1-6}$ alkyl, halogen, hydroxy, cyano, oxo or $C_{1-6}$ haloalkyl, (c) $C_{1-6}$ haloalkyl, (d) $C_{1-6}$ hydroxyalkyl, (e) $C_{1-3}$ alkoxy-$C_{1-3}$ alkyl, (f) $C_{3-6}$ cycloalkyl-$C_{1-6}$ alkyl, (g) $C_{1-6}$ alkoxy, (h) amino, (i) $C_{1-6}$ alkylamino, (j) di-$C_{1-6}$ alkylamino (k) $C_{3-6}$ cycloalkylamino, (l) phenyl-$C_{1-3}$ alkyl or (m) phenyl said phenyl optionally substituted with one to three groups independently selected in each occurrence form the group consisting of $C_{1-6}$ alkyl, $C_{1-6}$ alkoxy, halogen, —SO$_2$NR$^{6a}$R$^{6b}$ and —NHSO$_2$C$_{1-6}$ alkyl; (n) tetrahydropyranyl, (o) tetrahydrofuranyl; (p) cycloalkoxy optionally independently substituted with one or two halogen, hydroxy or oxo, (q) $C_{4-6}$ cycloalkyl-amino, (r) tetrahydropyranyl-methyl, (s) pyridinyl or (t) cyanomethyl; $R^{6a}$ and $R^{6b}$ are independently hydrogen, $C_{1-6}$ alkyl or $C_{1-6}$ acyl; Ar is phenyl optionally substituted with one to three substituents independently selected in each occurrence from the group consisting of halogen, $C_{1-6}$ alkyl, $C_{1-6}$ alkoxy, cyano and nitro; m and n are independently one or two; or, pharmaceutically acceptable salts thereof.

In a twelfth embodiment of the present invention there is provided a method for treating an HIV-1 infection, or preventing an HIV-1 infection, or treating AIDS or ARC, comprising co-administering to a host in need thereof a therapeutically effective amount of a compound according to formula I wherein $R^1$, $R^2$, $R^3$, $R^4$, $R^5$, $R^{6a}$, $R^{6b}$, $R^7$, $R^8$, $R^{9a}$, $R^{9b}$, $R^{10a}$, $R^{10b}$, $R^{11}$, A1, A2, A3, B1, Ar, X, m, n and p are as defined herein above, or pharmaceutically acceptable salts thereof, and at least one compound selected from the group consisting of HIV-1 protease inhibitors, nucleoside reverse transcriptase inhibitors, non-nucleoside reverse transcriptase inhibitors, CCR5 antagonists and viral fusion inhibitors.

In another embodiment of the present invention there is provided a method for treating an HIV-1 infection, or preventing an HIV-1 infection, or treating AIDS or ARC, comprising co-administering to a host in need thereof a therapeutically effective amount of a compound according to formula I wherein $R^1$ is selected from the group consisting of phenyl, pyridinyl and pyrimidinyl optionally substituted with $C_{1-6}$ alkyl, $C_{1-6}$ haloalkyl, $C_{1-6}$ alkoxy, hydroxy, cyano and halogen; or pharmaceutically acceptable salts thereof, and at least one compound selected from the group consisting of HIV-1 protease inhibitors, nucleoside reverse transcriptase inhibitors, non-nucleoside reverse transcriptase inhibitors, CCR5 antagonists and viral fusion inhibitors.

In a thirteenth embodiment of the present invention there is provided a method for treating an HIV-1 infection, or preventing an HIV-1 infection, or treating AIDS or ARC, comprising co-administering to a host in need thereof a therapeutically effective amount of a compound according to formula I wherein $R^1$, $R^2$, $R^3$, $R^4$, $R^5$, $R^{6a}$, $R^{6b}$, $R^7$, $R^8$, $R^{9a}$, $R^{9b}$, $R^{10a}$, $R^{10b}$, $R^{11}$, A1, A2, A3, B1, Ar, X, m, n and p are as defined herein above, or pharmaceutically acceptable salts thereof, and at least one compound selected from the group consisting of zidovudine, lamivudine, didanosine, zalcitabine, stavudine, rescriptor, sustiva and viramune, efavirenz, nevirapine or delavirdine, saquinavir, ritonavir, nelfinavir, indinavir, amprenavir, lopinavir and enfuvirtide.

In yet another embodiment of the present invention there is provided a method for treating an HIV-1 infection, or preventing an HIV-1 infection, or treating AIDS or ARC, comprising co-administering to a host in need thereof a therapeutically effective amount of a compound according to formula I wherein $R^1$ is selected from the group consisting of phenyl, pyridinyl and pyrimidinyl optionally substituted with $C_{1-6}$ alkyl, $C_{1-6}$ haloalkyl, $C_{1-6}$ alkoxy, hydroxy, cyano and halogen; or pharmaceutically acceptable salts thereof, and at least one compound selected from the group consisting of zidovudine, lamivudine, didanosine, zalcitabine, stavudine, rescriptor, sustiva and viramune, efavirenz, nevirapine or delavirdine, saquinavir, ritonavir, nelfinavir, indinavir, amprenavir, lopinavir and enfuvirtide In a fourteenth embodiment of the present invention there is provided a method for treating a mammal with a disease state that is alleviated by a $CCR^5$ receptor antagonist wherein said disease is solid organ transplant rejection, graft v. host disease, arthritis, rheumatoid arthritis, inflammatory bowel disease, atopic dermatitis, psoriasis, asthma, allergies or multiple sclerosis which comprises administering to the mammal in need thereof a therapeutically effective amount of a compound according to formula I wherein $R^1$, $R^2$, $R^3$, $R^4$, $R^5$, $R^{6a}$, $R^{6b}$, $R^7$, $R^8$, $R^{9a}$, $R^{9b}$, $R^{10a}$, $R^{10b}$, $R^{11}$, A1, A2, A3, B1, Ar, X, m, n and p are as defined herein above, or pharmaceutically acceptable salts thereof.

In another embodiment of the present invention there is provided a method for treating a mammal afflicted with arthritis or rheumatoid arthritis which comprises administering to the mammal in need thereof a therapeutically effective amount of a compound according to formula I wherein $R^1$, $R^2$, $R^3$, $R^4$, $R^5$, $R^{6a}$, $R^{6b}$, $R^7$, $R^8$, $R^{9a}$, $R^{9b}$, $R^{10a}$, $R^{10b}$, $R^{11}$, A1, A2, A3, B1, Ar, X, m, n and p are as defined herein above, or pharmaceutically acceptable salts thereof.

In still another embodiment of the present invention there is provided a method for treating a mammal afflicted with solid organ transplant rejection or graft v. host disease which comprises administering to the mammal in need thereof a therapeutically effective amount of a compound according to formula I wherein $R^1$ is selected from the group consisting of phenyl, pyridinyl and pyrimidinyl optionally substituted with $C_{1-6}$ alkyl, $C_{1-6}$ haloalkyl, $C_{1-6}$ alkoxy, hydroxy, cyano and halogen, or pharmaceutically acceptable salts thereof.

In a fifteenth embodiment of the present invention there is provided pharmaceutical composition comprising a therapeutically effective quantity of a compound according to formula I wherein $R^1$, $R^2$, $R^3$, $R^4$, $R^5$, $R^{6a}$, $R^{6b}$, $R^7$, $R^8$, $R^{9a}$, $R^{9b}$, $R^{10a}$, $R^{10b}$, $R^{11}$, A1, A2, A3, B1, Ar, X, m, n and p are as defined herein above, or pharmaceutically acceptable salts thereof and at least one pharmaceutically acceptable carrier, excipient or diluent.

In a further embodiment of the present invention there is provided pharmaceutical composition comprising a therapeutically effective quantity of a compound according to formula I wherein $R^1$ is selected from the group consisting of phenyl, pyridinyl and pyrimidinyl optionally substituted with $C_{1-6}$ alkyl, $C_{1-6}$ haloalkyl, $C_{1-6}$ alkoxy, hydroxy, cyano and halogen, or pharmaceutically acceptable salts thereof and at least one pharmaceutically acceptable carrier, excipient or diluent Definitions The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. The open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkylalkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cycloalkyl and R" is $C_{1-3}$ alkylene as defined herein.

The term "cycloalkoxy" as used herein means an —O-cycloalkyl group, wherein cycloalkyl is as defined above such as cyclohexyloxy cyclopentyloxy, cyclobutyloxy and cyclopropyloxy. "Lower alkoxy" as used herein denotes an alkoxy group with a "lower alkyl" group as previously defined. "$C_{3-7}$ cycloalkoxy" as used herein refers to an —O-cycloalkyl wherein the cycloalkyl is three to seven-membered ring.

The term "haloalkyl" as used herein denotes a unbranched or branched chain alkyl group as defined above wherein 1, 2, 3 or more hydrogen atoms are substituted by a halogen.

Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. $C_{1-6}$ alkoxy-$C_{1-3}$ alkyl refers to the substituent wherein a $C_{1-3}$ alkyl is substituted by a $C_{1-6}$ alkoxy radical.

The terms "amino", "alkylamino" and "dialkylamino" as used herein refer to —$NH_2$, —NHR and —$NR_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to $NH_2(CH_2)n$-, $RHN(CH_2)n$-, and $R_2N(CH_2)n$- respectively wherein n is 1 to 6 and R is alkyl as defined above. "$C_{1-10}$ alkylamino" as used herein refers to an -aminoalkyl wherein alkyl is $C_{1-10}$. The term "phenylamino" as used herein refers to —NBPh wherein Ph represents an optionally substituted phenyl group. The term "$C_{4-6}$ cycloalkylamino" refers to a group —NHR wherein R is a cycloalkyl group as defined herein.

Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of phenylalkyl radicals include, but are not limited to, benzyl, phenylethyl and 3-phenylpropyl. The terms "arylalkyl" or "aralkyl" are interpreted similarly except R' is an aryl radical as defined herein. The terms "(het)arylalkyl" or "(het)aralkyl" are interpreted similarly except R' is optionally an aryl or a heteroaryl radical as defined herein.

The terms "tetrahydrofuran" and "tetrahydropyran" refer to a five- and six-membered heterocyclic rings containing one oxygen atom is the ring wherein the point of attachment is anywhere on the ring.

It will be appreciated by the skilled artisan that the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. The present invention includes all the individual stereoisomers (e.g. enantiomers), racemic mixtures or partially resolved mixtures of the compounds of formula I and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "Topics in Stereochemistry", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, α-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxillary) to produce diastereomers which can be separated by chromatography or by fractional crystallization after which time the chiral auxiliary is chemically removed to afford the pure enantiomers.

The compounds of formula I contain at least one basic center and suitable acid addition salts are formed from acids which form non-toxic salts. Examples of salts of inorganic acids include the hydrochloride, hydrobromide, hydroiodide, chloride, bromide, iodide, sulphate, bisulphate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 66, 1-19, 1977.

Protecting groups are used in the preparation of compounds of the present invention and the term "protecting group" as used herein refers to a chemical group that (a) efficiently combines with a reactive group in a molecule; (b) prevents a reactive group from participating in an undesirable chemical reaction; and (c) can be easily removed after protection of the reactive group is no longer required. Protecting groups are used in synthesis to temporarily mask the characteristic chemistry of a functional group because it interferes with another reaction. Reagents and protocols for to introduce and remove protecting groups are well known and have been reviewed in numerous texts (e.g., T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 John Wiley and Sons, 1971-1996). One skilled in the chemical arts will appreciate that on occasion protocols must be optimized for a particular molecule and such optimization is well with the ability of one skilled in these arts. Amino-protecting groups used extensively herein include N-urethanes such as the N-benzyloxycarbonyl group (cbz) or tert-butoxycarbonyl (BOC) which is prepared by reaction with di(t-butyl)dicarbonate and benzyl groups. Benzyl groups are removed conveniently by hydrogenolysis and BOC groups are labile under acidic conditions.

Current HIV-1 therapy utilizes drug "cocktails" containing two or more drugs which frequently have different modes of action including NRTIs, NNRTIs, PIs and fusion inhibitors. This strategy decreases the opportunity for resistant mutants to emerge.

The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA. Typical suitable NRTIs include zidovudine (AZT; RETROVIR®); didanosine (ddI; VIDEX®); zalcitabine (ddC; HIVID®); stavudine (d4T; ZERIT®); lamivudine (3TC; EPIVIR®); abacavir (ZIAGEN®); adefovir dipivoxil [bis(POM)-PMEA; PREVON®]; lobucavir (BMS-180194), a nucleoside reverse transcriptase inhibitor disclosed in EP-0358154 and EP-0736533; BCH-10652, a reverse transcriptase inhibitor (in the form of a racemic mixture of BCH-10618 and BCH-10619) under development by Biochem Pharma; emitricitabine [(−)-FTC] in development by Triangle Pharmaceuticals; β-L-FD4 (also called β-L-D4C and named, β-L-2',3'-dicleoxy-5-fluoro-cytidene) licensed Vion Pharmaceuticals; DAPD, the purine nucleoside, (−)-β-D-2,6-diamino-purine dioxolane disclosed in EP-0656778 and licensed to Triangle Pharmaceuticals; and lodenosine (FddA), 9-(2,3-dideoxy-2-fluoro-β-D-threo-pentofuranosyl) adenine, an acid stable purine-based reverse transcriptase inhibitor under development by U.S. Bioscience Inc.

The term "non-nucleoside reverse transcriptase inhibitors" ("NNRTI"'s) as used herein means non-nucleosides that inhibit the activity of HIV-1 reverse transcriptase. Typical suitable NNRTIs include nevirapine (BI-RG-587; VIRAMUNE®); delaviradine (BHAP, U-90152; RESCRIPTOR®); efavirenz (DMP-266; SUSTIVA®); PNU-142721, a furopyridine-thio-pyrimidine under development by Pfizer; AG-1549 (formerly Shionogi # S-11153); 5-(3,5-dichlorophenyl)-thio-4-isopropyl-1-(4-pyridyl)methyl-1H-imidazol-2-ylmethyl carbonate disclosed in WO 96/10019; MKC-442 (1-(ethoxy-methyl)-5-(1-methylethyl)-6-(phenylmethyl)-(2,4(1H, 3H)-pyrimidinedione); and (+)-calanolide A (NSC-675451) and B, coumarin derivatives disclosed in U.S. Pat. No. 5,489,697. TMC 125 (etravirine) and TMC 278 are two NNRTIs currently in development by Tibotech The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character. Typical suitable PIs include saquinavir (Ro 31-8959; INVIRASE®; FORTOVASE®); ritonavir (ABT-538; NORVIR®); indinavir (MK-639; CRIXIVAN®); nelfnavir (AG-1343; VIRACEPT®); amprenavir (141W94; AGENERASE®); lasinavir (BMS-234475); DMP-450, a cyclic urea under development by Triangle Pharmaceuticals; BMS-2322623, an azapeptide under development by Bristol-Myers Squibb as a 2nd-generation HIV-1 PI; ABT-378 under development by Abbott; and AG-1549 an imidazole carbamate under development by Agouron Pharmaceuticals, Inc.

Other antiviral agents include hydroxyurea, ribavirin, IL-2, IL-12, pentafuside. Hydroxyurea (Droxia), a ribonucleoside triphosphate reductase inhibitor shown to have a synergistic effect on the activity of didanosine and has been studied with stavudine. IL-2 (aldesleukin; PROLEUKIN®) is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314. Pentafuside (FUZEON®) a 36-amino acid synthetic peptide that inhibits fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. Ribavirin, 1-β-D-ribofuranosyl-1H-1,2,4-triazole-3-carboxamide.

The term "viral fusion inhibitors" as used herein refers to compounds which inhibit fusion of the free virus particle and introduction of the viral RNA into a host cell independent of the molecular locus of inhibitor binding. Viral fusion inhibitors therefore include, but are not limited to T-20 peptide and protein soluble receptors, antibodies, chimeric antibodies, humanized antibodies. Other CD-4 binding ligands including BMS-378806, BMS-488043 or CXCR4 binding ligands including KRH-1636 (K. Ichiyama et al. *Proc. Nat. Acad. Sci. USA* 2003 100(7):4185-4190) could also be co-administered with the present invention.

In addition to the potential for CCR5 modulators in the management of HIV infections, the CCR5 receptor is an important regulator of immune function and compounds of the present invention may prove valuable in the treatment of disorders of the immune system. Treatment of solid organ transplant rejection, graft v. host disease, arthritis, rheumatoid arthritis, inflammatory bowel disease, atopic dermatitis, psoriasis, asthma, allergies or multiple sclerosis by administering to a human in need of such treatment an effective amount of a CCR5 antagonist compound of the present invention is also possible.

Methods for Treating Rheumatoid Arthritis

Modulators of the CCR5 receptor may be useful in the treatment of various inflammatory conditions. Rheumatoid arthritis is characterized by infiltration of memory T lymphocytes and monocytes into inflamed joints. As leukocyte chemotactic factors, chemokines play an indispensable role in the attraction of macrophages to various tissues of the body, a process which is essential for both inflammation and the body's response to infection. Because chemokines and their receptors regulate trafficking and activation of leukocytes which contribute to the pathophysiology of inflammatory and infectious diseases, agents which modulate CCR5 activity, preferably antagonizing interactions of chemokines and their receptors, are useful in the therapeutic treatment of such inflammatory diseases.

Elevated levels of CC chemokines, especially CCL2, CCL3 and CCL5, have been found in the joints of patients with rheumatoid arthritis and have been correlated with the recruitment on monocytes and T cells into synovial tissues (I. F. Charo and R. M. Ransohoff, *New Eng. J. Med.* 2006 354: 610-621). T-cells recovered from synovial fluid of rheumatoid arthritis have been shown to express CCR5 and CXCR3. P. Gao et al., *J. Leukocyte Biol.* 2003 73:273-280) Met-RANTES is an amino-terminal modified RANTES derivative which blocks RANTES binding to the CCR1 and CCR5receptors with nanomolar potency. (A. E. Proudfoot et al., *J. Biol. Chem.* 1996 271:2599-2603). The severity of arthritis in rats adjuvant-induced arthritis was reduced by the administration of Met-RANTES. In addition, the levels of pro-inflammatory cytokines TNF-α and IL-1β. (S. Shahrara et al. *Arthr. & Rheum.* 2005 52:1907-1919) Met-RANTES has been shown to ameliorate the development of inflammation in an art recognized rodent model of inflammation, the collagen induced arthritis. (C. Plater-Zyberk et al. *Immunol. Lett.* 1997 57:117-120)

TAK-779 has also been shown to reduce both the incidence and severity of arthritis in the collagen-induced arthritis model. The antagonist inhibited the infiltration of inflammatory CCR5+ T-cells into the joint. (Y.-F. Yang et al., *Eur. J. Immunol.* 2002 32:2124-2132). Another CCR5 antagonist, SCH-X, was shown to reduce the incidence and severity of collagen-induced arthritis in rhesus monkeys. (M. P. M. Vierboom et al., *Arthr. & Rheum.* 2005 52(20):627-636).

In some anti-inflammatory conditions compounds of the present invention may be administered in combination with other anti-inflammatory drugs which may have a alternative mode of action. Compounds which may be combined with CCR5 antagonists include, but are not limited to:

(a) a lipoxygenase antagonist or biosynthesis inhibitor such as an inhibitor of 5-lipoxygenase, leukotriene antagonists (e.g., zafirlukast, montelukast, pranlukast, iralukast, pobilukast, SKB-106,203), leukotriene biosynthesis inhibitors (e.g., zileuton, BAY-1005);

(b) a non-steroidal anti-inflammatory agent or cyclooxygenase (COX1 and/or COX2) inhibitor such as such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicarns (isoxicarn, piroxicam, sudoxicam and tenoxican), salicylates (acetyl salicylic acid, sulfasalazine), pyrazolones (apazone, bezpiperylon, feprazone, mofebutazone, oxyphenbutazone, phenylbutazone) and celecoxib;

(c) a TNF inhibitor such as infliximab (REMICADE®), etanercept (ENBREL®), or adalimumab (HUMIRA®);

(d) anti-inflammatory steroids such as beclomethasone, methylprednisolone, betamethasone, prednisone, dexamethasone, and hydrocortisone;

(e) immunomodulators such as cyclosporine, leflunomide (ARAVA®), azathioprine (AZASAN®), penicillamine and levamisole;

(f) folate antagonists such as methotrexate;

(g) gold compounds such as aurothioglucose, gold sodium thiomalate or auranofin.

Methods for Treating Transplant Rejection

Rejection following solid organ transplantation also is characterized by infiltration of T-cells and macrophages expressing the CCR5 receptor into the interstitial area. (J. Pattison et al., *Lancet* 1994 343:209-211) Renal transplant patients homozygous for the CCR5Δ32 deletion a significant survival advantage of patients heterozygous for the CCR5Δ32 deletion or homozygous wild type patients. (M. Fischereder et al., *Lancet* 2001 357:1758-1761) CCR5$^{-/-}$ knock-out mice showed significant prolong graft survival in after transplantation of heart and islet tissue. (W. Gao et al., *Transplantation* 2001 72:1199-1205; R. Abdi et al., *Diabetes* 2002 51:2489-2495. Blocking the CCR5 receptor activation has been found to significantly extend cardiac allograph survival. (W. W. Hancock et al., *Curr. Opin. Immunol.* 2003 15:479-486).

In treatment of transplant rejection or graft vs. host diseases CCR5 antagonists of the present invention may be administered in combination with other immunosuppressive agents including, but are not limited to, cyclosporine (SANDIMMUNE®), tacrolimus (PROGRAF®, FK-506), sirolimus (RAPAMUNE®, rapamycin), mycophenolate mofetil (CELLCEPT®), methotrexate, anti-IL-2 receptor (anti-CD25) antibodies such as daclizumab (ZENAPAX®) or basiliximab (SIMULECT®), anti-CD3 antibodies visilizumab (NUVION®) or muromonab (OKT3, ORTHOCLONE®).

Methods for Treating Asthma and COPD

Antagonism of the CCR5 receptor has been suggested as a target to inhibit of progression of asthma and COPD by antagonism of Th1 activation: B. Ma et al., J. Immunol. 2006 176(8):4968-4978, B. Ma et al., *J. Clin. Investig.* 2005 115 (12):3460-3472 and J. K. L. Walker et al., *Am. J. Respir. Cell Mo. Biol.* 2006 34:711-718.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride (BOC$_2$O), benzyl (Bn), butyl (Bu), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphospno)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), lithium hexamethyl disilazane (LiHMDS), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: NewYork, 1991, Volumes 140. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

Examples of representative compounds encompassed by, and within the scope of, the present invention are provided in the following Tables. These examples and preparations which follow are provided to enable those skilled in the art to more clearly understand and to practice the present invention. They should not be considered as limiting the scope of the invention, but merely as being illustrative and representative thereof.

In general, the nomenclature used in this application is based on AUTONOM™ v.4.0, a Beilstein Institute computerized system for the generation of IUPAC systematic nomenclature. If there is a discrepancy between a depicted structure and a name given that structure, the depicted structure is to be accorded more weight.

2-Benzyl-octahydro-pyrrolo[3,4-c]pyrrole (16a) was prepared by [2,3]-dipolar cycloaddition of an imine ylide with N-benzylmaleimide as described previously (R. Colon-Cruz et al. WO 02/070523 and M. Björsne et al. WO 02/060902). Reduction of the imide, and selective debenzylation are accomplished as described therein. Pyrrolo[3,4-c]pyrrole-2 (1H)-carboxylic acid, hexahydro-, 1,1-dimethylethyl ester (16b) is prepared from 16a by acylation and debenzylation (R. Colon-Cruz et al. WO 02/070523, supra).

Compounds of the present invention which are 2-[2-(4-phenyl-piperidin-4-yl)-ethyl]-octahydro-pyrrolo[3,4-c]pyrrole derivatives (TABLE I) are typically prepared by reductive amination of 16a or 16b with an aldehyde, e.g., 14, as depicted in step 5 of SCHEME A to afford 18a.

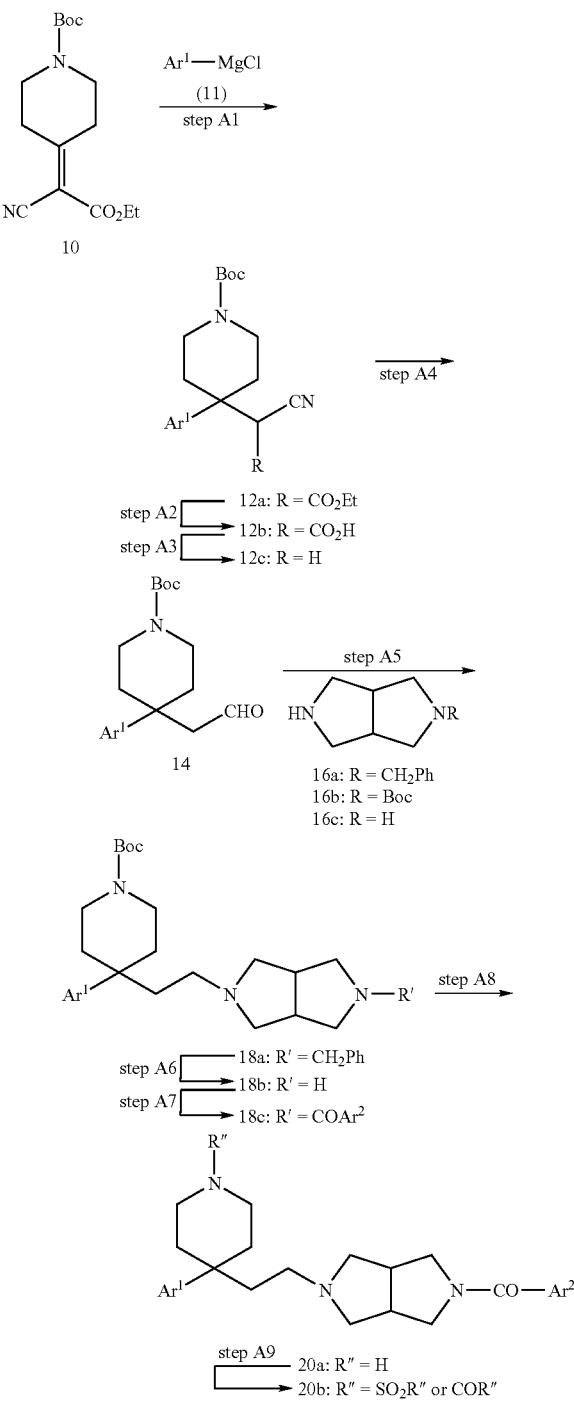

N-Boc-4-(2-oxo-ethyl)-4-phenyl-piperidine (14, Ar=C$_6$H$_5$) was prepared by conjugate addition of an aryl Grignard reagent 11 to N-Boc-4-(1-cyano-2-ethoxy-2-oxoethylidene)-1-piperidine (CAS Reg. No. 193537-11-0), to afford 12a which is saponified and decarboxylated to afford the nitrile 12c. Hydrolysis of esters may be achieved under conditions of acid or base catalysis in aqueous salt to afford the corresponding carboxylic acid. Typically the ester is treated with an excess of a suitable base (e.g., LiOH, NaOH or KOH) in aqueous organic solvent (e.g., EtOH, MeOH, THF, dioxane, MeCN) at RT for up to 18 h. The reaction can be accelerated by running the reaction at elevated temperature, typically reflux temperatures.

The resulting nitrile is then reduced to the corresponding aldehyde 14 (B. Chaudar et al. *Synth. Commun.* 2006 36(3): 279-284; W. Z. Kazmierski et al WO2004054974 published Jul. 1, 2004). Nitriles can be reduced to aldehydes using a metal hydride reducing agent to add a hydride to the nitrile and hydrolyzing the resulting imine in situ. Typical hydride reagents which have been used include $LiAlH_4$, $LiAlH(O$-tert-$Bu)_3$, DIBAL and $NaAlH_4$. (J. March, *Advanced Organic Chemistry*, John Wiley and Sons, NY, 1992, pp 919-920). Compounds with substitution on the aryl ring are prepared analogously from substituted Grignard reagents.

Amine protecting groups are well know in the art and have been reviewed in numerous texts (e.g., T. W. Greene and P. G. M. Wuts, *Protective Groups in Organic Synthesis*, 3rd edition, John Wiley & Sons, New York, 1999, and Harrison and Harrison et al., *Compendium of Synthetic Organic Methods*, Vols. 1-8 John Wiley and Sons, 1971-1996). The benzyl, methoxybenzyl or benzyloxycarbonyl groups are commonly used and are cleaved, for example, hydrogenolytically, e.g. with hydrogen in the presence of a catalyst such as palladium/charcoal in a solvent such as MeOH, EtOH, EtOAc, DMF, DMF/acetone or glacial HOAc optionally with the addition of an acid such as HCl at temperatures between 0 and 50° C., but preferably at ambient temperature, and at a hydrogen pressure of 1 to 7 bar, but preferably 3 to 5 bar. Alternately a tert-butyl or tert-butyloxycarbonyl group an effective amine protecting group that is preferably cleaved by treating with an acid such as TTA or HCl, optionally using a solvent such as DCM, dioxane or $Et_2O$. tert-Butyl protecting groups are not cleaved by hydrogenation.

The side chain bearing the aldehyde is introduced onto the octahydro-pyrrolo[3,4-c]pyrrole scaffold by reductive amination. Reductive amination is preferably carried out by combining an amine and carbonyl compound in the presence of a complex metal hydride reducing agent such as $NaBH_4$, $LiBH_4$, $NaB(CN)H_3$, $Zn(BH_4)_2$, sodium triacetoxyborohydride or borane/pyridine conveniently at a pH of 1-7 or in the presence of hydrogen and a hydrogenation catalyst, e.g. in the presence of palladium/charcoal, at a hydrogen pressure of 1 to 5 bar, preferably at temperatures between 20° C. and the boiling temperature of the solvent used. Optionally a dehydrating agent, such as molecular sieves or $Ti(IV)(O$-$i$-$Pr)_4$, is added to facilitate formation of the intermediate imine at ambient temperature. It may also be advantageous to protect potentially reactive groups during the reaction with conventional protecting groups which are cleaved again by conventional methods after the reaction. Reductive amination procedures have been reviewed: R. M. Hutchings and M. K. Hutchings Reduction of C=N to CHNH by *Metal Hydrides in Comprehensive Organic Synthesis* col. 8, I. Fleming (Ed) Pergamon, Oxford 1991 pp. 47-54.

After the first nitrogen substituent is introduced and elaborated the remaining nitrogen of the octahydro-pyrrolo[3,4-c]pyrrole scaffold is deprotected and acylated to afford 18c. Acylations can be conveniently carried out with a corresponding acyl halide or acid anhydride, which are prepared from the corresponding carboxylic acid, in a solvent such as DCM, $CHCl_3$, $CCl_4$, $Et_2O$, THF, dioxane, benzene, toluene, MeCN, DMF, aqueous sodium hydroxide solution or sulfolane optionally in the presence of an inorganic or organic base at temperatures between -20 and 200° C., but preferably at temperatures between -10 and 160° C. Typical organic bases include tertiary amines include but are not limited to TEA, pyridine. Typical inorganic bases include but are not limited to $K_2CO_3$, $Na_2CO_3$ and $NaHCO_3$. Sulfonylations can be carried out analogously from the appropriate alkyl or aryl sulfonyl chloride.

Alternatively an amide can be prepared by the coupling reaction of an amine compound of formula 16a, 16b, 18b, 38, 60b, 68b or 74b and a carboxylic acid in the presence of a coupling reagent, e.g diimides (e.g., EDCI, DCC), EEDQ, benzotriazol-1-yloxy-tris(dimethylamino)phosphonium hexafluorophosphate (BOP), DEAD-$Ph_3P$, diethylcyanophosphate, diethylphosphorylazide, 2-chloro-1-methylpyridinium iodide, or ethyl chloroformate, in an inert solvent, e.g. acetone, DMF, MeCN; halogenated hydrocarbons, such as DCM, DCE, $CHCl_3$; and ethers, such as THF and dioxane. If desired, this reaction may be carried out in the presence of an additive such as HOBt or 1-hydroxyazabenzotriazole or in the presence of a base such as pyridine, TEA, DIPEA or NMM.

Finally deprotection of the piperidine nitrogen and subsequent acylation, sulfonylation or alkylation affords the desired compounds of the invention. Acylation with a carboxylic acid, $R'''CO_2H$, carboxylic acid chloride, $R'''COCl$ or carboxylic acid anhydride $(R'''CO)_2O$ or sulfonylation with a sulfonyl chloride, $R'''SO_2Cl$ is carried as described previously. The amine can be alkylated with an alkyl, heteroalkyl or haloalkyl substituted with a leaving group. Common leaving groups which can be used included halogen, especially bromo iodo or chloro groups, alkylsulfonates or haloalkylsulfonates. R''' can be alkyl, haloalkyl, heteroalkyl, optionally substituted cycloalkyl, alkylcycloalkyl, optionally substituted phenyl, furanyl or pyranyl.

The following examples illustrate that the sequence in which these steps are performed is a matter of convenience and they can be readily reversed such that the acylation is first carried out on the 2-benzyl-octahydro-pyrrolo[3,4-c]pyrrole after which the second amine is deprotected and subjected to reductive amination. Furthermore elaboration of the piperidine, pyrrolidinyl or azetindinyl nitrogen substituent can be carried out before or after the reductive amination step.

TABLE I

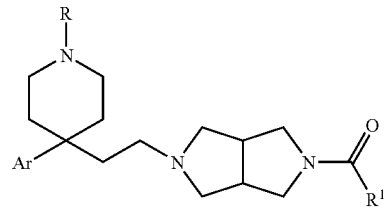

| Cpd # | Ar | $R^1$ | R | ms |
|---|---|---|---|---|
| I-1 | Ph | A | $COOCMe_3$ | 534 |
| I-2 | 3-F-Ph | A | $COOCMe_3$ | 552 |
| I-3 | 3-F-Ph | A | COPh | 556 |
| I-4 | Ph | A | COPh | 538 |
| I-5 | Ph | A | $COOCMe_3$ | 518 |
| I-6 | 3-F-Ph | A | $COOCMe_3$ | 536 |
| I-7 | 3-F-Ph | A | $SO_2$-3-F-Ph | 610 |
| I-8 | Ph | A | $SO_2$-3-F-Ph | 592 |
| I-9[1] | Ph | A | CO—$C_6H_4$-4-$SO_2NH_2$ | 617 |
| I-10[1] | Ph | A | CO—$C_6H_4$-4-$SO_2NHMe$ | 631 |
| I-11[1] | Ph | A | CO—$C_6H_4$-4-$SO_2NMe_2$ | 645 |
| I-12[1] | Ph | A | CO—$C_6H_4$-3-$SO_2NH_2$ | 617 |
| I-13[1] | Ph | A | CO—$C_6H_4$-3-$SO_2NHMe$ | 631 |
| I-14[1] | Ph | A | CO—$C_6H_4$-3-$SO_2NMe_2$ | 645 |
| I-15[1] | 3-F-Ph | A | CO—$C_6H_4$-4-$SO_2NHMe$ | 649 |
| I-16[1] | 3-F-Ph | A | CO—$C_6H_4$-4-$SO_2NHMe_2$ | 663 |

TABLE I-continued

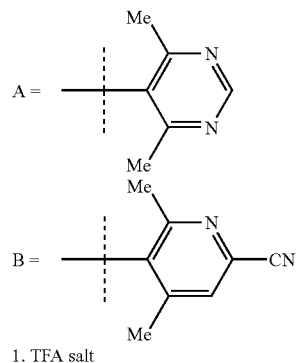

| Cpd # | Ar | R¹ | R | ms |
|---|---|---|---|---|
| I-17[1] | 3-F-Ph | A | CO—$C_6H_4$-3-$SO_2NH_2$ | 635 |
| I-18[1] | 3-F-Ph | A | CO—$C_6H_4$-3-$SO_2NHMe$ | 649 |
| I-19[1] | 3-F-Ph | A | CO—$C_6H_4$-3-$SO_2NMe_2$ | 663 |
| I-20[1] | Ph | A | CO—$C_6H_4$-4-$NHSO_2Me$ | 631 |
| I-21[1] | 3-F-Ph | A | CO—$C_6H_4$-4-$NHSO_2Me$ | 649 |
| I-22 | 3-F-Ph | A | COMe | 494 |
| I-23 | Ph | A | COMe | 476 |
| I-24 | Ph | A | CO-i-Pr | 504 |
| I-25 | 3-F-Ph | A | CO-i-Pr | 532 |
| I-26[1] | Ph | A | CO-c-$C_3H_5$ | 502 |
| I-27[1] | Ph | A | CO-c-$C_4H_7$ | 516 |
| I-28[1] | Ph | A | CO-c-$C_5H_9$ | 530 |
| I-29[1] | Ph | A | CO-c-$C_6H_{11}$ | 544 |
| I-30[1] | Ph | A | CO—(tetrahydropyran) | 546 |
| I-31[1] | Ph | A | CO—$CH_2CMe_3$ | 532 |
| I-32[1] | Ph | A | CO—$CH_2$-c-$C_5C_9$ | 544 |
| I-33[1] | Ph | A | CO—$CH_2CF_3$ | 544 |
| I-34[1] | 3-F-Ph | A | CO-c-$C_3H_5$ | 520 |
| I-35[1] | 3-F-Ph | A | CO-c-$C_4H_7$ | 534 |
| I-36[1] | 3-F-Ph | A | CO-c-$C_5H_9$ | 548 |
| I-37[1] | 3-F-Ph | A | CO-c-$C_6H_{11}$ | 562 |
| I-38[1] | 3-F-Ph | A | CO—(tetrahydropyran) | 564 |
| I-39[1] | 3-F-Ph | A | $COCH_2CMe_3$ | 550 |
| I-40[1] | 3-F-Ph | A | $COCH_2$-c-$C_5H_9$ | 562 |
| I-41[1] | 3-F-Ph | A | $COCH_2CF_3$ | 562 |
| I-42 | 3-F-Ph | A | CO—(1-Me-cyclopropyl) | 534 |
| I-43 | 3-F-Ph | A | CO—(1-$CF_3$-cyclopropyl) | 588 |
| I-44 | 3-F-Ph | A | $COCMe_2CH_2OH$ | 552 |
| I-45 | 3-F-Ph | B | CO—$CMe_3$ | 580 |

A = 4,6-dimethyl-pyrimidin-5-yl

B = 2,4-dimethyl-6-cyano-pyridin-3-yl

1. TFA salt

Compounds of the present invention which are 2-[2-(3-phenyl-azetidin-3-yl)-ethyl]-octahydro-pyrrolo[3,4-c]pyrrole derivatives (TABLE II) are typically prepared by reductive amination of 16a or 16b with an aldehyde 28d as depicted in SCHEME B. Alternately, the amine component of the reductive amination can be (4,6-dimethyl-pyrimidin-5-yl)-(hexahydro-pyrrolo[3,4-c]pyrrol-2-yl)-methanone (38, Ar²=4,6-dimethyl-pyrimidin-5-yl) or other amide depicted in TABLE II.

SCHEME B

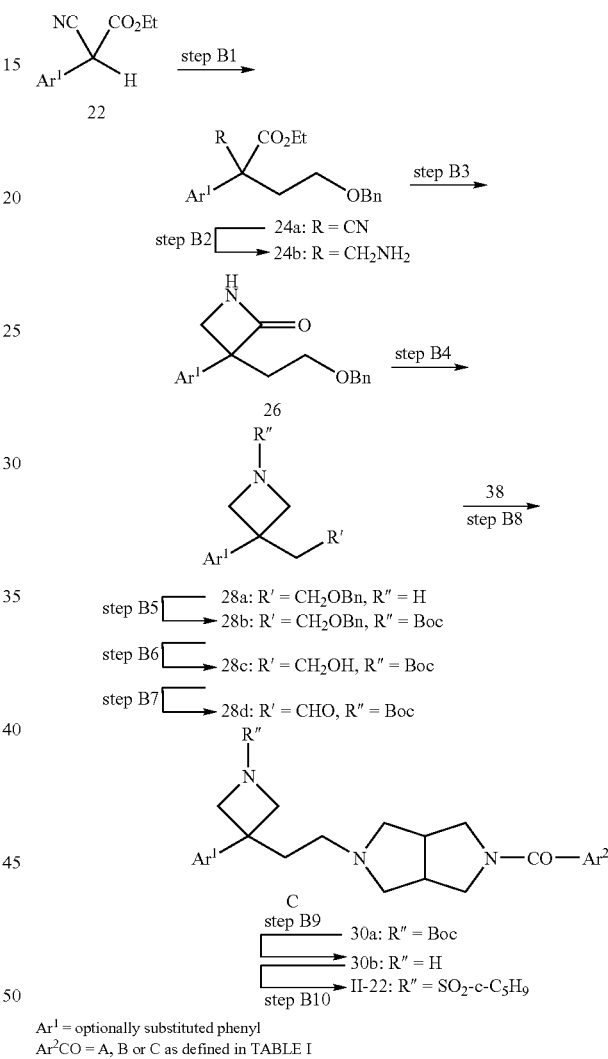

Ar¹ = optionally substituted phenyl
Ar²CO = A, B or C as defined in TABLE I

The requisite (3-phenyl-azetidin-3-yl)-acetaldehydes 28d are prepared as depicted in SCHEME B. Ethyl phenylcyanoacetate (22) is alkylated with benzyl 2-bromoethyl ether to afford 24a. Carboxylic acid esters and nitriles can be alkylated at the α-position by deprotonation of the ester or amide with a strong base (e.g., LDA, (iso-Pr)₂NLi, lithium N-cyclohexyl-N-iso-propyl amide, tert-BuOK, $NaNH_2$, NaH and KH). The reaction is typically run in inert nonprotic solvents (e.g., THF, dioxane, DME, DMF) at temperatures from −78 to 0° C.

Reduction of the nitrile, closure of the β-lactam and subsequent reduction of the lactam affords the azetidine 28a which is converted to the corresponding N-Boc derivative 28b. The benzyl protecting group is cleaved and the resulting alcohol oxidized to the aldehyde which is incorporated into the final product by reductive amination and further elaboration of the azetidine as described previously.

Reduction of the nitrile 24a can be accomplished under known hydrogenation conditions in the presence of a metal catalyst, e.g. Raney nickel catalysts, palladium catalysts or platinum catalysts, preferably Raney nickel catalysts in an inert solvent, e.g. HOAc, alcohols, such as MeOH, EtOH; EtOAc, THF, and DMF. If desired, this reaction may be carried out in the presence or absence of an additive such as $NH_4OH$. Reduction of nitriles, amides and nitro groups are also conveniently carried out with $NaBH_4$ and $CoCl_2$ in hydroxylic and non-hydroxylic solvents (T. Satoh et al., *Tetrahedron Lett.* 1969 4588).

Reduction of the lactam to the corresponding azetidine can be accomplished with a suitable reducing agent e.g. $LiAlH_4$, DIBAL-H or LiBH4 in a reaction inert solvent, e.g. aliphatic hydrocarbons, such as hexane, heptane and petroleum ether; aromatic hydrocarbons, such as benzene, toluene, o-dichlorobenzene, and xylene; ethers, such as $Et_2O$, diisopropyl ether, THF, diglyme and dioxane, preferably the ethers.

TABLE II

| Cpd # | Ar | $R^1$ | R | ms |
|---|---|---|---|---|
| II-1 | Ph | A | CO-c-$C_5H_9$ | 502 |
| II-2 | Ph | A | $SO_2$—$C_6H_4$-3-F | 564 |
| II-3 | Ph | A | CO-c-$C_6H_4$-3-F | 528 |
| II-4 | Ph | A | CO-(tetrahydropyran) | 518 |
| II-5 | Ph | A | CO-(tetrahydrofuran) | 504 |
| II-6 | Ph | A | CO—$CH_2$-c-$C_5H_9$ | 516 |
| II-7 | Ph | A | CO—$CCMe_3$ | 490 |
| II-8 | Ph | A | CO—$CH_2CF_3$ | 516 |
| II-9 | Ph | A | CO-(difluorocyclobutyl) | 524 |
| II-10 | Ph | A | CO-(hydroxycyclohexyl) | 532 |
| II-11 | Ph | A | $COCH_2$-(tetrahydropyran) | 532 |
| II-12 | Ph | A | CO-(tetrahydrofuran) | 504 |
| II-13 | Ph | A | CO-(methylcyclopropyl) | 488 |
| II-14 | Ph | A | CO-(cyanocyclopropyl) | 499 |
| II-15 | Ph | A | CO-($CF_3$-cyclopropyl) | 542 |
| II-16 | Ph | A | CO—$CMe_2CH_2OH$ | 506 |
| II-17 | Ph | A | CO-(hydroxycyclopropyl) | 490 |
| II-18 | Ph | A | CO-(cyclopentanone) | 516 |
| II-19 | Ph | A | $SO_2$-i-Pr | 512 |
| II-20 | Ph | A | $SO_2$-c-$C_3H_5$ | 510 |
| II-21 | Ph | A | CO-(hydroxycyclopentyl) | 518 |
| II-22 | Ph | A | $SO_2$—$C_5H_9$ | 538 |
| II-23 | Ph | A | $CH_2CF_3$ | 488 |
| II-24 | Ph | A | $CH_2CHF_2$ | 470 |
| II-25 | Ph | D | CO-(tetrahydrofuran) | 572 |
| II-26 | Ph | D | CO-(difluorocyclohexyl) | 620 |
| II-27 | Ph | D | CO-(difluorocyclobutyl) | 592 |
| II-28 | 3-Cl-Ph | A | CO-(difluorocyclohexyl) | 587 |
| II-29 | 3-Cl-Ph | A | CO-(difluorocyclobutyl) | 559 |
| II-30 | Ph | B | CO-(difluorocyclobutyl) | 548 |

TABLE II-continued

| Cpd # | Ar | R¹ | R | ms |
|---|---|---|---|---|
| II-31 | Ph | E | CO-(4,4-difluorocyclohexyl) | 619 |
| II-32 | Ph | E | CO-(3,3-difluorocyclobutyl) | 591 |
| II-33 | Ph | F | CO-(4,4-difluorocyclohexyl) | 568 |
| II-34 | Ph | G | CO-(4,4-difluorocyclohexyl) | 551 |
| II-35 | Ph | G | CO-(3,3-difluorocyclobutyl) | 523 |
| II-36 | Ph | A | CO-3,5-di-F-C₆H₃ | 546 |
| II-37 | Ph | G | CO-(tetrahydrofuran-3-yl) | 503 |
| II-38 | Ph | B | CO-(tetrahydrofuran-3-yl) | 528 |
| II-39 | Ph | A | CO-(4,4-difluorocyclohexyl) | 552 |
| II-40 | Ph | B | CO-(4,4-difluorocyclohexyl) | 576 |
| II-41 | Ph | B | CO-(3,3-difluorocyclobutyl) | 548 |
| II-42 | Ph | E | CO-(3,3-difluorocyclobutyl) | 591 |
| II-43 | Ph | F | CO-(4,4-difluorocyclohexyl) | 568 |

R¹ groups:

A: R = H
D: R = CF₃
(4,6-dimethylpyrimidin-2-yl with 5-substituent)

B: R = CN
E: R = CF₃
G: R = H
(3,4-dimethylpyridin-2-yl with 5-substituent)

C: (3,5-dimethyl-1-(5-trifluoromethylpyridin-2-yl)pyrazol-4-yl)

F: (3,4-dimethyl-6-oxo-6H-pyran-5-yl)

Compounds of the present invention which are 2-[2-(3-phenyl-pyrrolidin-3-yl)-ethyl]-octahydro-pyrrolo[3,4-c]pyrrole derivatives (TABLE III) are typically prepared by reductive amination of 16a or 16b with an aldehyde 36c as depicted in SCHEME C.

SCHEME C

Ar₁CR₂CN step C1 [ 32a: R = H
         → 32b: R = CH₂CO₂Me ]

→ step C2 →

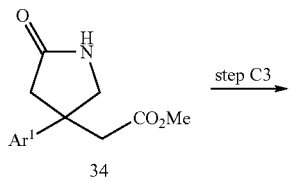

34

→ step C3 →

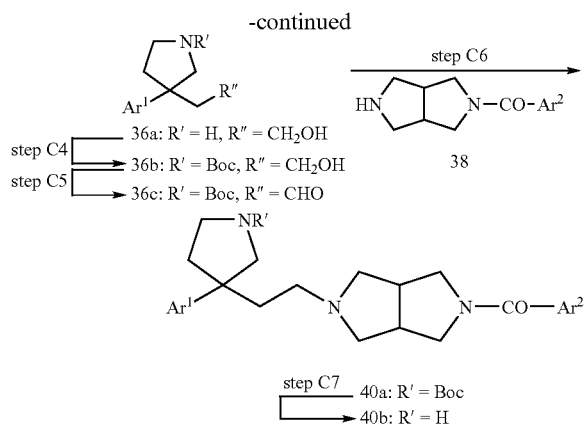

The preparation of N-Boc-3-(2-oxo-ethyl)-3-phenyl-pyrrolidine was carried out by a sequence analogous to SCHEME B except an arylacetonitrile is bis-alkylated with ethyl bromoacetate. Selective reduction of the nitrile to the corresponding amine was carried out with hydrogen and Raney-nickel and one of the newly appended acetic ester groups in cyclized to the lactam after which both the lactam and the ester are reduced. The amine is protected with a Boc group and the alcohol is re-oxidized to an aldehyde.

TABLE III

| Cpd # | Ar | $R^1$ | R | ms |
|---|---|---|---|---|
| III-1 | Ph | A | CO-c-$C_5H_9$ | 516 |
| III-2 | Ph | A | CO—$CH_2$-c-$C_5H_9$ | 530 |
| III-3 | Ph | A | CO-Me | 462 |
| III-4 | Ph | A | CO—$CMe_3$ | 504 |
| III-5 | Ph | B | CO-c-$C_5H_9$ | 540 |
| III-6 | Ph | B | CO—$CH_2$-c-$C_5H_9$ | 554 |
| III-7 | Ph | B | CO-Me | 486 |
| III-8 | Ph | B | CO—$CMe_3$ | 528 |
| III-9 | Ph | B | CO-(3,3-difluorocyclobutyl) | 562 |
| III-10 | Ph | C | CO-Me | 595 |
| III-11 | Ph | C | CO-c-$C_5H_9$ | 649 |
| III-12 | Ph | C | CO-(3,3-difluorocyclobutyl) | 671 |
| III-13 | 3F-Ph | B | $SO_2Me$ | 540 |
| III-14 | 3F-Ph | B | $CH_2CHF_2$ | 526 |

Compounds of the present invention which are 2-(3-azetidin-3-yl-3-phenyl-propyl)-octahydro-pyrrolo[3,4-c]pyrrole derivatives (TABLE IV) are typically prepared by reductive amination of 16a, 16b or 38 with an aldehyde derived from the oxidation of 46b as depicted in SCHEME D.

-continued

[Structure: Ar¹—CH(—)—CH₂CH₂—N(pyrrolopyrrole)N—CO—Ar²; azetidine with N-R″ attached]

step D7: 48a: R″ = Boc → 48b: R″ = H
step D8: 48b → 48c: R″ = SO₂Me

Ar¹ = optionally substituted phenyl
Ar²CO = A, B or C as defined in TABLE IV

The alcohol is obtained from 42a (CASRN 36476-86-5) by addition of an optionally substituted Grignard reagent to the nitrile and hydrolysis of the intermediate imine to afford ketone 42b. The addition of Grignard reagents can be carried out in inert solvents including ether and aromatic hydrocarbons. Good results are frequently obtained with benzene containing one equivalent of an ethereal solvent. Cuprous salts also can be beneficial (J. March, Advanced Organic Chemistry John Wiley & Sons, NY 4$^{th}$ ed, 1992 p. 936). The required 2-carbon fragment is introduced by a Wadsworth phosphonate coupling (W. S. Wadsworth, Jr. Org. React. 1977 25:73-253) with the salt of (diethoxy-phosphoryl)-acetic acid ethyl ester which affords 44. Exposure of 44 to hydrogen and a hydrogenation catalyst in the presence of (Boc)₂O results in concomitant hydrogenation of the olefin, hydrogenolysis of the benzhydryl substituent on the amine and acylation of the resulting secondary amine. The resulting ester is reduced to the alcohol 46b with DIBAL-H.

The requisite propanal derivative 46c is prepared in situ by oxidation of 46b with TEMPO and used in the reductive amination step without chromatographic purification. The oxidation of alcohols to aldehydes, ketones and carboxylic acids is an extraordinarily common transformation in organic synthesis and a correspondingly large number of alternative procedures, conditions and reagents are available which permit the oxidation of almost any alcohol. Among the commonly used reagents are $CrO_3$ or pyridinium dichromate (Jones oxidation ($CrO_3$/acetone), Collins reagent ($CrO_3$/pyridine)) in aqueous, organic or mixed solvents under acidic and basic conditions. Potassium permanganate, $MnO_2$ and Ce(IV) have been used extensively in organic synthesis. DMSO based oxidants including DMSO/DCC (Moffatt Oxidation), DMSO/Ac₂O, DMSO/SO₃ DMSO/(COCl)₂ (Swern Oxidation) in organic solvents in the presence of tertiary amines are often successful. Silver oxide or silver carbonate/CELITE® have been used successfully. The Dess-Martin periodinane run under neutral or near neutral conditions in organic solvents is commonly used. 2,2,6,6-Tetramethylpiperidine 1-oxyl (TEMPO) and sodium hypochlorite has been widely adapted to the oxidation of alcohols.

TABLE IV

[Structure with R-azetidine, Ar, and R¹-CO pyrrolopyrrole]

| Cpd # | Ar | R¹ | R | ms |
|---|---|---|---|---|
| IV-1 | Ph | A | CO—O-t-Bu | 520 |
| IV-2 | Ph | A | CO-c-C₅H₉ | 516 |
| IV-3 | Ph | A | CH₂CF₃ | 502 |
| IV-4 | Ph | A | CO—CH₂CHMe₂ | 504 |
| IV-5 | Ph | A | CO—(difluorocyclobutyl) | 538 |
| IV-6 | Ph | A | SO₂-i-Pr | 526 |
| IV-7 | Ph | A | SO₂-Me | 498 |
| IV-8 | Ph | A | SO₂-c-C₅H₉ | 552 |
| IV-9 | Ph | A | SO₂-c-C₃H₅ | 524 |
| IV-10 | Ph | A | CO-i-Pr | 490 |
| IV-11 | Ph | A | SO₂—CH₂CHMe₂ | 540 |
| IV-12 | Ph | A | SO₂-c-C₃H₅ | 548 |
| IV-13 | Ph | A | SO₂-c-C₅H₉ | 576 |
| IV-14 | 3-F-Ph | A | SO₂-m-F—C₆H₄ | 596 |
| IV-15 | 3-F-Ph | A | SO₂-c-C₅H₉ | 570 |
| IV-16 | 3-F-Ph | A | SO₂-c-C₃H₅ | 542 |
| IV-17 | 3-F-Ph | A | SO₂-(2-pyridyl) | 579 |
| IV-18 | 3-F-Ph | A | SO₂NMe₂ | 545 |
| IV-19 | Ph | B | COMe | 486 |
| IV-20 | 3-F-Ph | A | CH₂CN | 477 |
| IV-21 | 3,5-di-F-Ph | A | SO₂-c-C₃H₅ | 560 |

A = 4,5,6-trimethylpyrimidin-2-yl (Me at 4,5,6; H at 2)

B = 3,4-dimethyl-6-cyanopyridin-2-yl (Me groups, CN substituent)

Compounds of the present invention which are 2-(3-phenyl-3-piperidin-4-yl-propyl)-octahydro-pyrrolo[3,4-c]pyrrole derivatives (TABLE V) are typically prepared by reductive amination of 16a, 16b or 38 with 56b. The starting material for the preparation of 56b was the commercially available Boc protected piperidine 50a (CAS Reg. No. 91419-52-2) which was deprotected and converted to 50b. The resulting nitrile was converted to 56b and subsequently incorporated onto the octahydro-pyrrolo[3,4-c]pyrrole scaffold to produce 58a as described previously in SCHEME D. Removal of the Boc protecting group and acylation, sulfonylation or alkylation was carried out by normal procedures.

SCHEME E

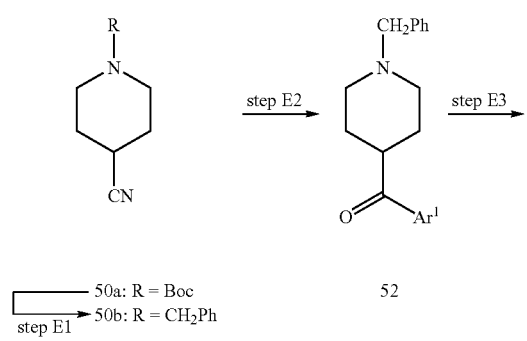

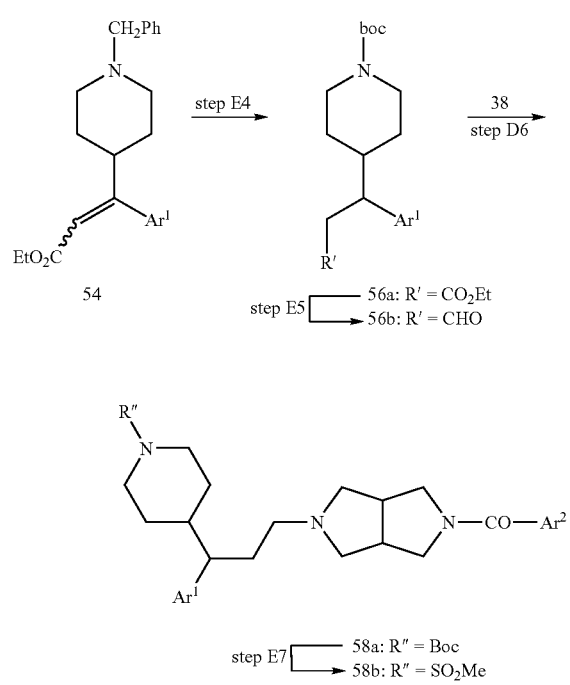

Ar¹ = optionally substituted phenyl
Ar²CO = A or B as defined in TABLE IV

TABLE V

| Cpd. No. | Ar | R¹ | R | ms |
|---|---|---|---|---|
| V-1 | Ph | A | CH₂CF₃ | 530 |
| V-2 | Ph | A | CONH-t-Bu | 547 |

TABLE V-continued

| Cpd. No. | Ar | R¹ | R | ms |
|---|---|---|---|---|
| V-3 | Ph | A | CONH-i-Pr | 533 |
| V-4 | Ph | A | CO—NHEt | 519 |
| V-5 | Ph | A | CO—NH-c-C₅H₉ | 559 |
| V-6 | Ph | A | CO—O—(3-hydroxycyclopentyl) | 576 |
| V-7 | Ph | A | CO—OMe | 506 |
| V-8 | Ph | A | SO₂-Ph | 588 |
| V-9 | Ph | A | SO₂-i-Pr | 554 |
| V-10 | Ph | A | SO₂CH₂Ph | 602 |
| V-11 | Ph | A | SO₂-Et | 540 |
| V-12 | Ph | A | SO₂-Me | 526 |
| V-13 | Ph | A | CO-Et | 504 |
| V-14 | Ph | A | CO—CH₂CHMe₂ | 532 |
| V-15 | Ph | A | CO—CMe₃ | 532 |
| V-16 | Ph | A | COCH₂OMe | 520 |
| V-17 | Ph | A | CO—CH₂-c-C₅H₉ | 558 |
| V-18 | Ph | A | SO₂—C₅H₉ | 580 |
| V-19 | Ph | A | CO-i-Pr | 518 |
| V-20 | Ph | A | SO₂-c-C₃H₅ | 552 |
| V-21 | Ph | A | CH₂CHF₂ | 512 |
| V-22 | Ph | A | COCF₃ | 544 |
| V-23 | Ph | A | SO₂CH₂CF₃ | 594 |
| V-24 | Ph | B | SO₂Me | 550 |
| V-25 | 3-F-Ph | A | CH₂CHF₂ | 530 |
| V-26 | 3-F-Ph | A | SO₂Me | 544 |
| V-27 | 3-F-Ph | A | SO₂-(2-pyridyl) | 607 |
| V-28 | 3-F-Ph | A | SO₂NMe₂ | 573 |
| V-29 | 3-F-Ph | A | SO₂Me | 544 |
| V-30 | 3-F-Ph | A | SO₂Me | 544 |
| V-31 | Ph | A | CH₂CN | 487 |
| V-32 | 3,5-di-F-Ph | A | SO₂Me | ## |
| V-33 | 3,5-di-F-Ph | A | CH₂CHF₂ | |
| V-34 | 3,5-di-F-Ph | E | CH₂CHF₂ | |

TABLE V-continued

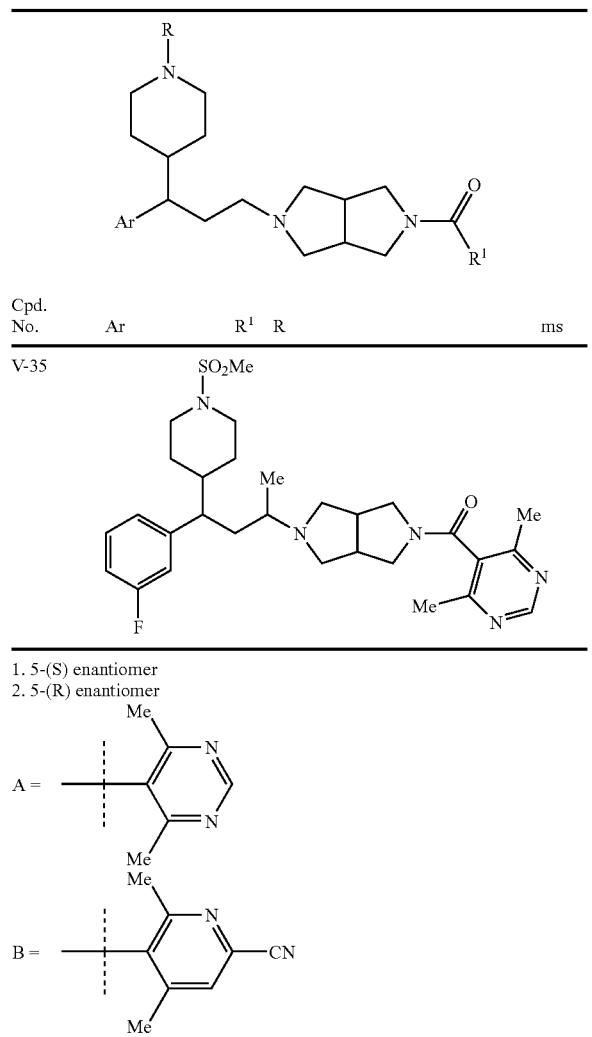

| Cpd. No. | Ar | R¹ | R | ms |
|---|---|---|---|---|
| V-35 | | | $SO_2Me$ | |

1. 5-(S) enantiomer
2. 5-(R) enantiomer

A = (4,6-dimethylpyrimidin-5-yl)

B = (4,6-dimethyl-2-cyanopyridin-3-yl)

Biological Assays

The capacity for novel compounds of the present invention to bind to the CCR5 receptor and thereby antagonize CCR5 function can be evaluated with assay systems known in the art. The capacity of compounds of the present invention to inhibit infection of $CD4^+/CCR5^+$ expressing cells can be determined using a cell-cell fusion assay as described in example 8 or an antiviral assay as described in example 9.

Functional assays directly measure the ability of a compound to produce a biologically relevant response or inhibit a response produced by a natural ligand (i.e., characterizes the agonist vs. antagonist properties of the test compounds). In a calcium flux assay, cells expressing the CCR5 are loaded with calcium sensitive dyes prior to addition of compound or the natural CCR5 ligand. Compounds with agonist properties will induce a calcium flux signal in the cell, while the compounds of this invention are identified as compounds which do not induce signaling by themselves but are capable of blocking signaling by the natural ligand RANTES.

A chemotaxis assay is a functional assay which measures the ability of a non-adherent cell line expressing human CCR5 receptor to migrate across a membrane in response to either test compounds or natural attractant ligand(s) (i.e., RANTES, MIP-1β). Generally, chemotaxis assays monitor the directional movement or migration of a suitable cell (such as a leukocyte (e.g., lymphocyte, eosinophil, basophil)) into or through a barrier (e.g., endothelium, a permeable filter membrane), toward, from a first surface of the barrier toward an opposite second surface containing attractant ligands. Membranes or filters provide convenient barriers to monitor the directional movement or migration of a suitable cell into or through a filter, toward increased levels of an attractant. In some assays, the membrane is coated with a substance to facilitate adhesion, such as ICAM-1, fibronectin or collagen. Such assays provide an in vitro approximation of leukocyte "homing". Compounds that are antagonists not only fail to induce chemotaxis, but are also capable of inhibiting cell migration in response to known CCR5 ligands.

A suitable membrane, having a suitable pore size for monitoring specific migration in response to compound, including, for example, nitrocellulose, polycarbonate, is selected. For example, pore sizes of about 3-8 microns, and preferably about 5-8 microns can be used. The pore size can be uniform on a filter or within a range of suitable pore sizes.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed in the presence and absence of the antibody by determining the presence of the label adherent to the membrane and/or present in the second chamber using an appropriate method (e.g., by detecting radioactivity, fluorescence, immunoassay).

In a more physiologically relevant variation of a chemotaxis assay, particularly for T cells, monocytes or cells expressing a mammalian CCR5, transendothelial migration is monitored. Such assays mimic leukocytes migration from blood vessels toward chemoattractants present in the tissues at sites of inflammation by crossing the endothelial cell layer lining the vessel wall.

Endothelial cells can be cultured and form a confluent layer on a microporous filter or membrane, optionally coated with a substance such as collagen, fibronectin, or other extracellular matrix proteins, to facilitate the attachment of endothelial cells. A variety of mammalian endothelial cells can are available for monolayer formation, including for example, vein, artery or microvascular endothelium. Generally, the assay is performed by detecting the directional migration of cells into or through a membrane or filter.

In a composition comprising cells capable of migration and expressing a mammalian CCR5 receptor can be placed in the first chamber. A composition comprising one or more natural attractant ligands capable of inducing chemotaxis of the cells in the first chamber is placed in the second chamber. Preferably shortly before the cells are placed in the first chamber, or simultaneously with the cells, a composition comprising the compound to be tested is placed, preferably, in the first chamber. Compounds which can bind receptor and inhibit the induction of chemotaxis by natural attractant ligands, of the cells expressing a mammalian CCR5 are inhibitors of receptor function. A reduction in the extent of migration induced by the ligand or promoter in the presence of the antibody is indicative of inhibitory activity.

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, a non-nucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions, and that the treatment of animals includes the treatment of humans as well as other primates. Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLE 1

4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidine-1-carboxylic acid tert-butyl ester (I-2) and (4,6-dimethyl-pyrimidin-5-yl)-(5-{2-[1-(3-fluoro-benzenesulfonyl)-4-(3-fluoro-phenyl)-piperidin-4-yl]-ethyl}-hexahydro-pyrrolo[3,4-c]pyrrol-2-yl)-methanone (I-7)

The structures are depicted in SCHEME A wherein Ar$^1$ is 3-fluoro-phenyl and Ar$^2$ is 4,6-dimethyl-pyrimidin-5-yl. 4-(Cyano-ethoxycarbonyl-methylene)-piperidine-1-carboxylic acid tert-butyl ester (10) was prepared by the procedure disclosed by W. M. Kazmierski et al. in WO2004054974.

step A1—3-Fluorophenyl magnesium bromide (100 mL, 0.1 mol, 1M in THF) was added dropwise over 2 h to a mixture of CuI (2.5 g, 13.13 mmol), 10 (12.5 g, 42.47 mmol) in THF (100 mL). The resulting mixture was stirred at 0° C. for 1 h then quenched with saturated $NH_4Cl$. The biphasic mixture was partitioned between EtOAc and saturated $NH_4Cl$. The aqueous layer was back-extracted once with EtOAc. The combined extracts were dried ($Na_2SO_4$), filtered and evaporated. The residue was purified by $SiO_2$ chromatography eluting with a hexanes/EtOAc gradient (0 to 20% EtOAc) to afford 12.5 g (75%) of 12a.

step A2—A solution of NaOH (12.8 g, 0.32 mol) in water (75 mL) was added to a solution of 12a and EtOH (100 mL). The resulting mixture was stirred at RT for 15 h then diluted with $H_2O$ (100 mL), cooled to 0° C., and adjusted to pH 3 with concentrated HCl. The mixture was extracted twice with EtOAc while maintaining the pH of the aqueous layer at ca. 3. The combined extracts were dried ($Na_2SO_4$), filtered and evaporated to afford 11.5 g (100%) of 12b.

step A3—Copper(I) oxide (1.14 g, 7.967 mmol) was added to a solution of 12b (11.5 g, 31.73 mmol) and MeCN (150 mL). The resulting suspension was stirred at reflux for 1 h then cooled to RT. After 10-15 min of heating the purple suspension turned dark orange. The cooled reaction mixture was filtered through CELITE® and the cake was rinsed with MeOH. The filtrate was evaporated and the residue was recrystallized from i-$Pr_2O$ to afford 6 g (60%) of 12c.

step A4—DIBAL-H (50 mL, 58 mmol, 1M in DCM) was added dropwise over 2 h to a solution of 12c (6 g, 18.84 mmol) in DCM (100 mL) at −78° C. When the addition was complete, the reaction mixture was stirred at −78 to −60° C. for 2 h then quenched at −60° C. by dropwise addition of MeOH (3 mL). The reaction mixture was partitioned between DCM and a saturated aqueous solution of citric acid. The aqueous layer was back extracted three times with DCM and the combined extracts were dried ($Na_2SO_4$), filtered and evaporated to afford 5.1 g (85%) of 14.

step A5—Sodium triacetoxyborohydride (4 g, 18.87 mmol) was added at RT to a solution of 14 (5.1 g, 15.87 mmol) and 16a (3.5 g, 17.3 mmol) in DCM (100 m-L). The resulting mixture was stirred at RT for 2 h then partitioned between DCM and a saturated aqueous solution $NaHCO_3$. The aqueous layer was back-extracted twice with DCM. The combined organic layers were dried ($Na_2SO_4$), filtered and evaporated. The residue was purified by $SiO_2$ chromatography eluting with a gradient of DCM/DCM-MeOH—$NH_4OH$ [60/10/1] (100 to 50% DCM) to afford 2.35 g (50%) of 18a.

step A6—Hydrogen (1 atm, balloon) was bubbled through a suspension of 18a (2.35 g, 4.629 mmol) and 10% Pd/C (0.35 g) in EtOH (100 mL). The reaction mixture was vigorously stirred at RT under hydrogen (1 atm) for 16 h. An additional 0.35 g of 20% Pd(OH)$_2$/C was then added and the resulting mixture was stirred at RT under $H_2$ (1 atm) for 5 h then filtered. The cake was rinsed with MeOH and the filtrate was evaporated to afford 1.933 g (100%) of 18b.

step A7—To a mixture of 18b (1.933 g, 4.629 mmol), 4,6-dimethyl-pyrimidine-5-carboxylic acid (0.85 g, 5.586 mmol), EDCI (1.07 g, 5.581 mmol) and HOBt (0.85 g, 5.55 mmol) in DCM (40 mL) was added DIPEA (1.2 ml, 6.886 mmol). The resulting mixture was stirred at RT overnight then partitioned between DCM and $H_2O$. The aqueous layer was back extracted once with DCM and the combined organic extracts were dried ($Na_2SO_4$), filtered and evaporated. The residue was purified by $SiO_2$ chromatography eluting with a gradient of DCM/DCM-MeOH—$NH_4OH$ [60/10/1] (100 to 60% DCM) to afford 1.714 g (67%) of I-2.

step A8—To a solution of I-2 (1.67 g, 3.027 mmol), dioxane (10 mL) and MeOH (10 mL) was added ethereal HCl (20 mL, 1M HCl in $Et_2O$). The resulting mixture was stirred at RT for 3 h and then at 40° C. for 2 h. The reaction mixture was cooled to RT and evaporated to afford 2.035 g (100%) of 20a as a hexahydrochloride salt.

step A9—To a solution of 20a (0.075 g, 90.82 μmol) in DCM (0.5 mL) and pyridine (0.25 mL) was added 3-fluorobenzenesulfonyl chloride (18 μL, 0.222 mmol). The resulting clear solution was stirred at RT for 24 h then MeOH (1 μL) was added. The reaction mixture was stirred at RT for 1 hour then evaporated. The residue was purified by $SiO_2$ chromatography eluting with a gradient of DCM/DCM-MeOH—$NH_4OH$ [60/10/1] (100 to 60% DCM) to afford 0.035 g (65%) of I-7.

tert-Butyl 4-{2-[5-(4,6-dimethyl-pyrimidine-5-carbonyl)-hexahydro-pyrrolo[3,4-c]pyrrol-2-yl]-ethyl}-4-phenyl-piperidine-1-carboxylate (I-1) was prepared analogously to I-2 except in step 1, phenyl magnesium bromide was used in place of 3-fluoro-phenyl magnesium bromide. I-8 was prepared from I-1 as described in steps 8 and 9.

EXAMPLE 2

1-[4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidin-1-yl]-2,2-dimethyl-propan-1-one (I-6)

Pivaloyl chloride (27 μL, 0.222 mmol) was added to a solution of 20a (0.075 g, equivalent to 0.046 g (mass adjusted) of the amine, 90.82 μmol) in DCM (1 mL) and pyridine (0.25 mL). The resulting clear solution was stirred at RT for 24 h then evaporated. The residue was purified by $SiO_2$ chromatography eluting with a gradient of DCM/DCM-MeOH—$NH_4OH$ (60/10/1) (100 to 50% DCM) to afford 0.02 g (43%) of I-6.

The following were prepared analogously from (4,6-dimethyl-pyrimidin-5-yl)-(5-{2-[4-(3-fluoro-phenyl)-piperidin-4-yl]-ethyl}-hexahydro-pyrrolo[3,4-c]pyrrol-2-yl)-methanone using the acylating agent in parenthesis in place of pivaloyl chloride: I-3 (benzoyl chloride), I-22 (acetic anhydride), I-25 (isobutyryl chloride), I-34 (cyclopropanecarbonyl chloride), I-35 (cyclobutanecarbonyl chloride), I-36 (cyclopentanecarbonyl chloride), I-37 (cyclohexanecarbonyl chloride), I-38 (tetrahydropyran-4-carbonyl chloride), I-39 (3,3-dimethyl-butyryl chloride), I-40 (cyclopentyl-acetyl chloride), I-41 (2,2,2-trifluoropropionyl chloride).

The following were prepared analogously from (4,6-dimethyl-pyrimidin-5-yl)-{5-[2-(4-phenyl-piperidin-4-yl)-ethyl]-hexahydro-pyrrolo[3,4-c]pyrrol-2-yl}-methanone using the acylating agent in parenthesis in place of pivaloyl chloride: I-4 (benzoyl chloride), I-5 (pivaloyl chloride), I-23 (acetic anhydride), I-24 (isobutyryl chloride), I-26 (cyclopropanecarbonyl chloride), I-27 (cyclobutanecarbonyl chloride), I-28 (cyclopentanecarbonyl chloride), I-29 (cyclohexanecarbonyl chloride), I-30 (tetrahydropyran-4-carbonyl chloride), I-31 (3,3-dimethyl-butyryl chloride), I-32 (cyclopentyl-acetyl chloride), I-33 (2,2,2-trifluoropropionyl chloride).

EXAMPLE 3

(4,6-Dimethyl-pyrimidin-5-yl)-(5-{2-[4-(3-fluoro-phenyl)-1-(1-trifluoromethyl-cyclopropanecarbonyl)-piperidin-4-yl]-ethyl}-hexahydro-pyrrolo[3,4-c]pyrrol-2-yl)-methanone (I-43)

DIPEA (70 μl, 0.381 mmol) was added to a mixture of 20a (Ar$^1$=3-F-Ph and Ar$^2$=4,6-dimethyl-pyrimidin-5-yl; 0.075 g, 90.82 μmol), 1-trifluoromethylcyclopropanecarboxylic acid (0.029 g, 0.191 mmol), EDCI (0.027 g, 0.143 mmol), HOBt (0.022 g, 0.143 mmol) and DCM (1 mL). The resulting mixture was stirred at RT for 72 h and then partitioned between DCM and H$_2$O. The aqueous layer was twice back-extracted with DCM and the combined extracts were dried (Na$_2$SO$_4$), filtered and evaporated. The residue was purified by HPLC (7-10 SB-Phenyl column, water/acetonitrile 90/10 to 10/90 in 5 min, 1 mL/min) to give 0.022 g (41%) of I-43.

The following were prepared analogously from (4,6-dimethyl-pyrimidin-5-yl)-(5-{2-[4-(3-fluoro-phenyl)-piperidin-4-yl]-ethyl}-hexahydro-pyrrolo[3,4-c]pyrrol-2-yl)-methanone using the carboxylic acid in parenthesis in place of 1-trifluoromethylcyclopropanecarboxylic acid: I-42 (1-methyl-cyclopropanecarboxylic acid), I-15 (4-methylsulfamoyl-benzoic acid), I-16 (4-dimethylsulfamoyl-benzoic acid), I-17 (3-sulfamoyl-benzoic acid), I-18 (3-methylsulfamoyl-benzoic acid), I-19 (3-dimethylsulfamoyl-benzoic acid), I-21 (4-methanesulfonylamino-benzoic acid) and I-44 (2,2-dimethyl-3-hydroxy-propionic acid).

Similarly, I-9 (4-sulfamoyl-benzoic acid), I-10 (4-methylsulfamoyl-benzoic acid), I-11 (4-dimethylsulfamoyl-benzoic acid), I-12 (3-sulfamoyl-benzoic acid), I-13 (3-methylsulfamoyl-benzoic acid), I-14 (3-dimethylsulfamoyl-benzoic acid) and I-20 (4-methanesulfonylamino-benzoic acid) were prepared from 20a (Ar$^1$=C$_6$H$_5$ and Ar$^2$=4,6-dimethyl-pyrimidin-5-yl).

EXAMPLE 4

5-(5-{2-[1-(2,2-Dimethyl-propionyl)-4-(3-fluoro-phenyl)-piperidin-4-yl]-ethyl}-hexahydro-pyrrolo[3,4-c]pyrrole-2-carbonyl)-4,6-dimethyl-pyridine-2-carbonitrile (I-45)

(SCHEME A, Ar$^1$=3-fluorophenyl and Ar$^2$=6-cyano-2,4-dimethyl-pyridin-3-yl)

step A7—DIPEA (92 μl, 0.526 mmol) was added to a mixture of 18b (0.146 g, 0.351 mmol), 6-cyano-2,4-dimethyl-nicotinic acid (0.074 g, 0.421 mmol) and TBTU (0.147 g, 0.456 mmol) in DCM (5 mL) and DMF (0.5 mL). The resulting mixture was stirred at RT overnight then partitioned between DCM and H$_2$O. The aqueous layer was twice back-extracted twice with DCM. The combined extracts were dried (Na$_2$SO$_4$), filtered and evaporated. The residue was purified by SiO$_2$ chromatography eluting with a gradient of DCM/DCM-MeOH—NH$_4$OH [60/10/1] (100 to 50% DCM) to afford 0.045 g (22%) of 18c (Ar$^2$=6-cyano-2,4-dimethyl-pyridin-3-yl).

step A8—To a solution of 18c (0.045 g, 78.16 μmol) and DCM (1 mL) at RT was added 4M HCl in dioxane (1 mL). The reaction mixture was stirred at RT for 3 h then evaporated. The residue was triturated twice with Et$_2$O. The solvent was evaporated to afford 0.051 g (100%) of 20a (Ar$^2$=6-cyano-2,4-dimethyl-pyridin-3-yl).

step A9—To a solution of 20a (theoretically 78.16 μmol) in DCM (0.5 mL) and pyridine (0.25 mL) at RT was added trimethylacetyl chloride (48 μL, 0.391 mmol). The mixture was stirred at RT overnight then quenched with MeOH. The resulting solution was then stirred at RT for 1 h then evaporated. The residue was purified by SiO$_2$ chromatography eluting with a gradient of DCM/DCM-MeOH—NH$_4$OH [60/10/1] (100 to 50% DCM) to afford 0.012 g (28%) of I-45.

EXAMPLE 5

1-(3-{2-[5-(4,6-Dimethyl-pyrimidine-5-carbonyl)-hexahydro-pyrrolo[3,4-c]pyrrol-2-yl]-ethyl}-3-phenyl-pyrrolidin-1-yl)-ethanone (III-3)

SCHEME C (Ar$^1$=phenyl, Ar$^2$=4,6-dimethyl-pyrimidin-5-yl)

step C1—Lithium hexamethyldisilazane (200 mL, 0.2 mol, 1M in THF) was added dropwise to a solution of phenylacetonitrile (32a, 11 mL, 94.79 mmol, Ar$^1$=Ph) cooled to −78° C. in THF (100 mL). The resulting slurry was stirred at −78° C. for 1 h and then at 10° C. degrees for 15 min. The resulting clear solution was cooled to −78° C. and ethyl bromoacetate (24 ml, 0.216 mol) was added dropwise. The reaction mixture was stirred at −78° C. then warmed to RT and stirred for 24 h. The volatile solvents were evaporated and the residue partitioned between Et$_2$O and saturated aqueous NH$_4$Cl. The aqueous layer was twice back-extracted with Et$_2$O. Combined organic extracts were dried (MgSO$_4$), filtered and evaporated. The residue was purified by SiO$_2$ chromatography eluting with an EtOAc/hexane gradient (0 to 15% EtOAc) to afford 19 g (69%) of 32b.

step C2—A mixture of 32b (19 g, 65.67 mmol) and Ra—Ni (20 g of the slurry) was shaken at RT under H$_2$ (50 psi) for 48 h. The reaction mixture was filtered and the cake was rinsed with EtOH. The filtrate was evaporated to afford a viscous light yellow syrup which was purified by SiO$_2$ chromatography eluting with EtOAc to afford 15 g (92%) of 34.

step C3—LiAlH$_4$ (170 mL, 0.17 mol, 1M in Et$_2$O) was added dropwise to a solution of 34 (14 g, 56.614 mmol) in THF (100 mL) at RT. The resulting mixture was stirred at 70° C. overnight then cooled to 0° C. and quenched with H$_2$O (1.25 mL), 10% NaOH (1.25 mL) and H$_2$O (3.7 mL). The resulting precipitate was filtered and rinsed with EtOAc and the filtrate was evaporated to afford 8.46 g (78%) of 36a.

step C4—Di-tert-butyl dicarbonate (19 g, 87.06 mmol) was added at 0° C. to a mixture of 36a (8.46 g, 44.23 mmol) and NaHCO$_3$ (3.7 g, 44.04 mmol) in THF (150 mL) and H$_2$O (30 mL). The resulting mixture was warmed to RT and stirred overnight. The resulting solution was filtered and the cake was rinsed with THF. The filtrate was evaporated and the residue was purified by SiO$_2$ chromatography eluting with EtOAc/hexanes (1:1) to afford 10.3 g (80%) of 36b.

step C5—A solution of Dess-Martin periodinane (1.15 g, 2.711 mmol) in DCM (15 mL) and tert-BuOH (0.25 mL) was stirred at RT for 5 min. A solution of 36b (0.495 g, 1.699 mmol) and DCM (5 mL) was added and the resulting mixture was stirred at RT overnight then partitioned between DCM and 1M LiOH. The aqueous layer was back-extracted once with DCM. The combined organic extracts were dried (Na$_2$SO$_4$), filtered and evaporated to afford 36c which was used in the next step without purification.

step C6—Sodium triacetoxyborohydride (0.43 g, 2.029 mmol) was added to a solution of 36c (theoretically 1.699 mmol) and 38 (Ar$^2$=4,6-dimethyl-pyrimidin-5-yl, 0.42 g, 1.705 mmol) in DCM (15 mL). The resulting mixture was stirred at RT overnight then partitioned between DCM and a saturated aqueous NaHCO$_3$. The aqueous layer was twice back-extracted with DCM. The combined extracts were dried (Na$_2$SO$_4$), filtered and evaporated. The residue was purified by SiO$_2$ chromatography eluting with a gradient of DCM/DCM-MeOH—NH$_4$OH [60/10/1] (100 to 50% DCM) to afford 0.23 g (26% in two steps) of 40a.

step C7—A solution of 40a (0.23 g, 0.443 mmol), dioxane (2 mL), MeOH (2 mL) and 4M HCl in dioxane (2 mL) was stirred at 40° C. degrees for 4 h then evaporated to give 0.298 g (100%) of 40b as a heptahydrochloride salt.

step C8—Ac$_2$O (25 μl, 0.265 mmol) was added to a solution of 40b (0.06 g, 88.92 μmol) in DCM (0.4 mL) and pyridine (0.4 mL). The resulting mixture was stirred at RT for 72 h then quenched with MeOH (1 mL). The reaction mixture was stirred at RT then evaporated. The residue was purified by SiO$_2$ chromatography eluting with a gradient of DCM/DCM-MeOH—NH$_4$OH [60/10/1] (100 to 50% DCM) to afford 0.028 g (69%) of III-3.

The following were prepared analogously from (4,6-dimethyl-pyrimidin-5-yl)-{5-[2-(3-phenyl-pyrrolidin-3-yl)-ethyl]-hexahydro-pyrrolo[3,4-c]pyrrol-2-yl}-methanone using the acid chloride in parenthesis in place of acetic anhydride in the final step: III-1 (cyclopentanecarbonyl chloride), III-2 (cyclopentyl-acetyl chloride) and III-4 (pivaloyl chloride).

EXAMPLE 6

5-(5-{2-[1-(3,3-Difluoro-cyclobutanecarbonyl)-3-phenyl-pyrrolidin-3-yl]-ethyl}-hexahydro-pyrrolo[3,4-c]pyrrole-2-carbonyl)-4,6-dimethyl-pyridine-2-carbonitrile (III-9)

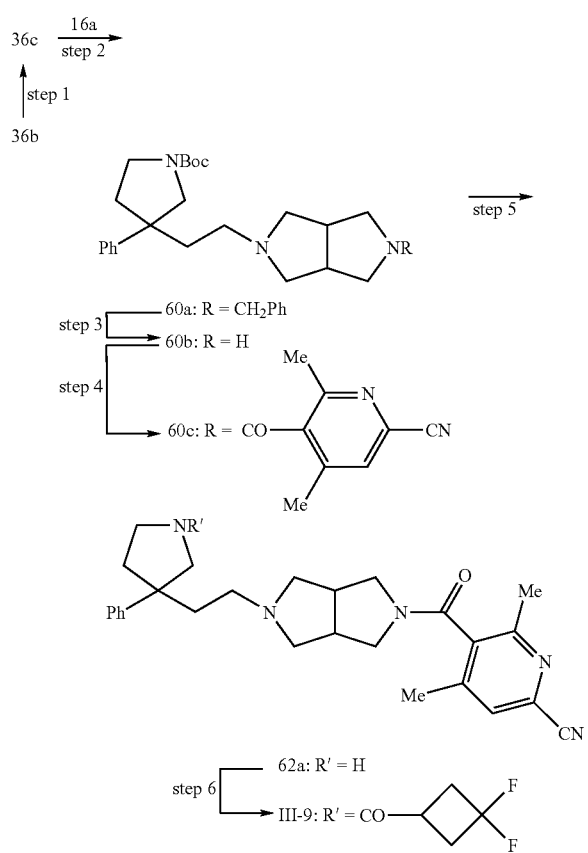

step 1—To a solution of 36b (Ar$^1$=Ph, 0.5 g, 1.716 mmol), DCM (15 mL) and H$_2$O (15 mL) was added NaHCO$_3$ (0.058 g, 0.686 mmol) and TEMPO (1.2 mg, 7.68 μmol). The mixture was cooled to 0° C. A solution of NaOCl (3 mL, 2.418 mmol, 6 wt %) was added dropwise and the resulting mixture was vigorously stirred at 0° C. then warmed to RT and stirred for 4 h. The organic layer was separated and the aqueous layer was back-extracted once with DCM. The combined organic layers were dried (Na$_2$SO$_4$), filtered and evaporated to 36c which was used in the next step without purification.

step 2—A mixture of 36c (theoretically 1.716 mmol) and 16a (0.38 g, 1.878 mmol) in DCM (10 mL) was stirred at 0° C. for 30 min then NaBH(OAc)$_3$ (0.44 g, 2.076 mmol) was added. The resulting mixture was stirred at 0° C. then warmed to RT and stirred overnight. The reaction mixture was partitioned between DCM and saturated aqueous NaHCO$_3$. The organic layer was dried (Na$_2$SO$_4$), filtered and evaporated. The residue was purified by SiO$_2$ chromatography eluting with a gradient of DCM/DCM-MeOH—NH$_4$OH [60/10/1] (100 to 50% DCM) to afford 0.476 g (58% for steps 1 & 2) of 60a.

step 3—Hydrogen (1 atm) was bubbled through a mixture of 60a (0.476 g, 1.001 mmol) and 20% Pd(OH)$_2$/C (0.3 g) and EtOH (25 mL) for 10 minutes. The resulting mixture was stirred at RT under H$_2$ (1 atm) for 48 h then filtered. The cake was rinsed with MeOH and the filtrate was evaporated. The residue was purified by SiO$_2$ chromatography eluting with a gradient of DCM/DCM-MeOH—NH$_4$OH (60/10/1) (100 to 0% DCM) to afford 0.24 g (62%) of 60b.

step 4—DIPEA (0.16 mL, 0.934 mmol) was added to a mixture of 60b (0.24 g, 0.623 mmol), 6-cyano-2,4-dimethyl-nicotinic acid (0.12 g, 0.611 mmol) and TBTU (0.26 g, 0.805 mmol) in DCM (5 mL) and DMF (0.5 mL). The resulting mixture was stirred at RT overnight before being partitioned between DCM and H$_2$O. The aqueous layer was back-extracted twice with DCM. The combined organic layers were dried (Na$_2$SO$_4$), filtered and evaporated. The residue was purified by SiO$_2$ chromatography eluting with a gradient of DCM/DCM-MeOH—NH$_4$OH (60/10/1) (100 to 50% DCM) to afford 0.157 g (46%) of 60c.

step 5—To a solution of 60c (0.157 g, 0.289 mmol) in DCM (2 mL) at RT was added 4M HCl solution in dioxane (2 mL). The reaction mixture was stirred for 2 h then evaporated to afford 0.19 g (100%) of 62a as a hexahydrochloride salt step 6—DIPEA (0.15 mL, 0.866 mmol) was added to a mixture of 62a (0.064 g, 96.26 μmol), 3,3-difluorocyclobutane-carboxylic acid (0.020 g, 0.144 mmol), EDCI (0.022 g, 0.116 mmol) and HOBt (0.018 g, 0.116 mmol) and DCM (0.4 mL). The resulting mixture was stirred at RT overnight then partitioned between DCM and H$_2$O. The aqueous layer was back-extracted twice with DCM. The combined organic layers were dried over (Na$_2$SO$_4$), filtered and evaporated. The residue was purified by SiO$_2$ chromatography eluting with a gradient of DCM/DCM-MeOH—NH$_4$OH (60/10/1) (100 to 50% DCM) to afford 0.02 g (37%) of III-9.

The following were prepared analogously from 4,6-dimethyl-5-{5-[2-(3-phenyl-pyrrolidin-3-yl)-ethyl]-hexahydro-pyrrolo[3,4-c]pyrrole-2-carbonyl}-pyridine-2-carbonitrile using the acylating agent in parenthesis in place of 3,3-difluorocyclobutane-carboxylic acid in the final step according to the procedure in step 8 of example 5: III-5 (cyclopentanecarbonyl chloride): III-6 (cyclopentyl-acetyl chloride), III-7 (acetic anhydride) and III-8 (pivaloyl chloride).

EXAMPLE 7

{5-[2-(1-Cyclopentanecarbonyl-3-phenyl-pyrrolidin-3-yl)-ethyl]-hexahydro-pyrrolo[3,4-c]pyrrol-2-yl}-[3,5-dimethyl-1-(5-trifluoromethyl-pyridin-2-yl)-1H-pyrazol-4-yl]-methanone (III-11)

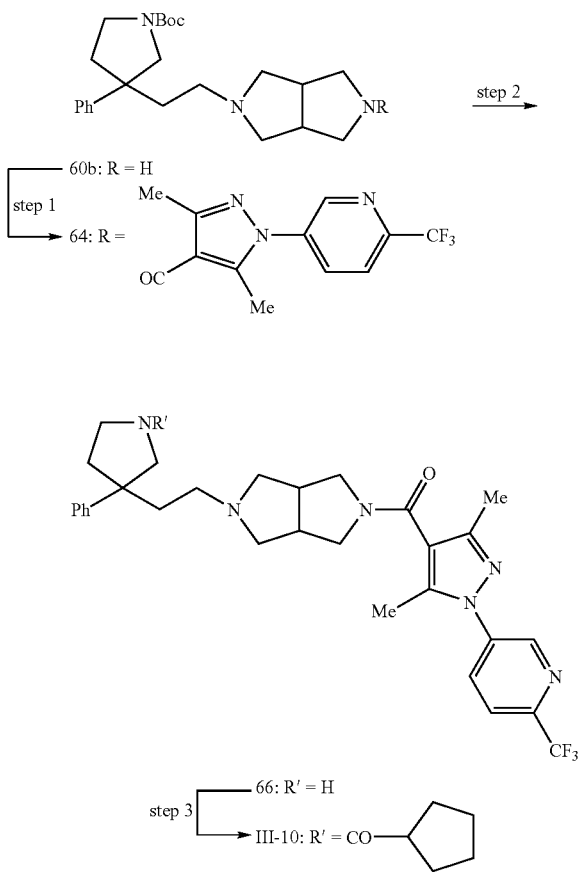

step 1—DIPEA (0.170 mL, 0.973 mmol) was added to a mixture of 60b (0.25 g, 0.648 mmol), 3,5-dimethyl-1-(5-trifluoromethyl-pyridin-2-yl)-1H-pyrazole-4-carboxylic acid (68, 0.2 g, 0.701 mmol), EDCI (0.15 g, 0.782 mmol), HOBt (0.120 g, 0.784 mmol) and DCM (5 mL). The resulting mixture was stirred at RT overnight then partitioned between DCM and $H_2O$. The aqueous layer was back-extracted twice with DCM. The combined organic layers were dried ($Na_2SO_4$), filtered and evaporated. The residue was purified by $SiO_2$ chromatography eluting with a gradient of DCM/DCM-MeOH—$NH_4OH$ (60/10/1) (100 to 50% DCM) to afford 0.285 g (78%) of 64.

step 2—To a solution of 64 (0.285 g, 0.437 mmol) in DCM (2 mL) was added a 4M HCl solution in dioxane (2 mL). The reaction mixture was stirred at RT for 3 h then evaporated. The residue was triturated twice with $Et_2O$ and the solvent was evaporated to give 0.288 g (100%) 66 as a trihydrochloride salt.

step 3—Cyclopentylcarbonyl chloride (41 µl, 0.340 mmol) was added to a solution of the trihydrochloride salt of 66 (0.075 g, 0.113 mmol) in DCM (0.75 mL) and pyridine (0.25 mL). The resulting mixture was stirred at RT overnight then quenched with MeOH (1 mL) and evaporated. The residue was purified by $SiO_2$ chromatography eluting with a gradient of DCM/DCM-MeOH—$NH_4OH$ (60/10/1) (100 to 50% DCM) to afford 0.041 g (55%) of III-11.

The following were prepared analogously from [3,5-dimethyl-1-(5-trifluoromethyl-pyridin-2-yl)-1H-pyrazol-4-yl]-{5-[2-(3-phenyl-pyrrolidin-3-yl)-ethyl]-hexahydro-pyrrolo[3,4-c]pyrrol-2-yl}-methanone using the acylating agent in parenthesis in place of cyclopentylcarbonyl chloride in the final step: III-10 (acetic anhydride) and III-12 (3,3-difluoro-cyclobutane-carboxylic acid using the EDCI coupling procedure in step 6 of example 6).

EXAMPLE 8

{5-[2-(1-Cyclopentanesulfonyl-3-phenyl-azetidin-3-yl)-ethyl]-hexahydro-pyrrolo[3,4-c]pyrrol-2-yl}-(4,6-dimethyl-pyrimidin-5-yl)-methanone (II-22)

SCHEME B ($Ar^1$=phenyl, $Ar^2$=4,6-dimethyl-pyrimidin-5-yl)

Preparation of (4,6-Dimethyl-pyrimidin-5-yl)-(hexahydro-pyrrolo[3,4-c]pyrrol-2-yl)-methanone (38 $Ar^2$=4,6-dimethyl-pyrimidin-5-yl)

To a mixture of 4,6-dimethyl-pyrimidine-5-carboxylic acid (0.85 g, 5.58 mmol, T. J. Kress et. al. *Heterocycles* 1994 38:1375) and 16a (1.13 g, 5.58 mmol, C. J. Ohnmacht et al. *J. Heterocycl. Chem.* 1983 20:321) in DCM (25 mL) at RT was added sequentially EDCI (1.43 g, 6.7 mmol), HOBt (0.9 g, 6.7 mmol) and DIPEA (3.9 mL, 22.34 mmol) and the mixture was stirred overnight at RT. The reaction mixture was washed with 5% $NaHCO_3$ solution, dried ($MgSO_4$) and concentrated in vacuo. The crude product was purified by flash chromatography on silica gel eluting with MeOH (containing 10% $NH_4OH$)/DCM (0 to 4%) to afford 1.5 g of (5-benzyl-hexahydro-pyrrolo[3,4-c]pyrrol-2-yl)-(4,6-dimethyl-pyrimidin-5-yl)-methanone: ms (ES+) m/z 337 (M+H)$^+$. To a solution of amide from the previous step (1.5 g, 4.45 mmol) in MeOH (50 mL) was added ammonium formate (2.81 g, 44.58 mmol). Palladium on charcoal previously wetted with MeOH was slowly added and the mixture heated to reflux for 8 h. The catalyst was filtered and solvent evaporated. The residue was purified by flash chromatography on silica gel eluting with MeOH (containing 10% $NH_4OH$)/DCM (0 to 4%) to afford 0.941 g of 38 ($Ar^2$=4,6-dimethyl-pyrimidin-5-yl): ms (ES+) m/z 247 (M+H)$^+$.

step B1—Ethyl phenylcyanoacetate (22, 18.3 mL, 0.1054 mol, $Ar^1$=Ph) was added dropwise to a suspension of NaH (4.85 g, 0.1213 mol, 60% dispersion in oil) in DMF (200 mL) cooled to 0° C. The resulting mixture was stirred at 0° C. for 30 min then benzyl 2-bromoethyl ether (20 mL, 0.1265 mmol) was added. The reaction mixture was then stirred at 60° C. overnight, cooled to RT and partitioned between EtOAc and a saturated aqueous $NH_4Cl$. The aqueous layer was thrice back-extracted with EtOAc. The combined organic extracts were dried ($Na_2SO_4$), filtered and evaporated. The residue was purified by $SiO_2$ chromatography eluting with a EtOAc/hexane gradient (5 to 95% EtOAc) to afford 20 g (60%) of 24a.

step B2—To a solution of 24a (20 g, 61.84 mmol), $CoCl_2.6H_2O$ (16.2 g, 68.09 mmol) and MeOH (150 mL) cooled to 0° C. was added portionwise $NaBH_4$ (5.85 g, 0.1546 mmol). Additional NaBH$_4$ was added when gas evolution ceased. When the addition was finished the reaction mixture was warmed to RT and stirred for 16 h then filtered through CELITE®. The cake was rinsed with MeOH and the filtrate was evaporated. The residue was partitioned between EtOAc (100 mL) and H$_2$O (100 mL). The insoluble material was removed by filtration through CELITE® and the cake rinsed with H$_2$O and EtOAc. The aqueous layer was acidified to pH 1 with 1M HCl. The aqueous layer was extracted once with EtOAc. The organic layer was back-extracted once with 1M hydrochloric acid. The combined aqueous layers were adjusted to pH 9 with 1M NaOH then thrice extracted with EtOAc. The combined organic layers were then dried (Na$_2$SO$_4$), filtered and evaporated to give 8.1 g (40%) of 24b which was used in the next reaction without purification.

step B3—To a to solution of 24b (8.1 g, 24.74 mmol) in Et$_2$O (150 mL) and THF (50 mL) cooled to 0° C. was added dropwise MeMgI (33 mL, 99 mmol, 3M in Et$_2$O) resulting in the formation of a grayish powder. The reaction mixture was stirred at RT for 3 h then quenched with saturated aqueous solution of NH$_4$Cl. The organic layer was separated and the aqueous layer was twice back-extracted EtOAc. The combined organic layers were dried (Na$_2$SO$_4$), filtered and evaporated. The residue was taken in EtOAc/hexane (1:1, 50 mL). The insoluble material was filtered and rinsed with EtOAc/hexane (1:1) to afford 2.8 g (40%) of 26.

step B4—To a solution of 26 (3.1 g, 11.02 mmol) in THF (50 mL) of THF cooled to 0° C. was added dropwise a 1M ethereal solution of LiAlH$_4$ (17 mL. 17 mmol). The resulting mixture was stirred at 60° C. for 6 h then cooled to 0° C. and quenched with H$_2$O (0.65 mL) followed by 15% aqueous NaOH (0.65 mL), H$_2$O (3.25 mL). The mixture was stirred at 0° C. for 30 min then filtered through CELITE®. The cake was rinsed with THF and the filtrate was evaporated to 28a which was used in the next step without purification.

step B5—Di-tert-butyl dicarbonate (4.81 g, 22.04 mmol) was added at 0° C. to a mixture of 28a (theoretically 11.02 mmol) and NaHCO$_3$ (1.9 g, 22.62 mmol) in THF (100 mL) and H$_2$O (15 mL). The resulting mixture was stirred at 0° C. then warmed to RT and stirred for 72 h. The solution was filtered through CELITE® and the cake was rinsed with THF and the filtrate was evaporated. The residue was purified by SiO$_2$ chromatography eluting with hexanes/EtOAc (9/1) to afford 2 g (49%) of 28b for the two steps.

step B6—A mixture of 28b (2 g, 5.442 mmol) and 20% Pd(OH)$_2$/C (0.25 g) in EtOH (50 mL) was stirred at RT under H$_2$ (1 atm) for 24 h. The reaction was filtered and the filter cake rinsed with EtOH and the filtrate was evaporated to afford 1.5 g (100%) of 28c.

step B7—To a solution of 28c (1.5 g, 5.408 mmol) and DCM (50 mL) was added H$_2$O (20 mL), NaHCO$_3$ (0.23 g, 2.738 mmol) and TEMPO (8.5 mg, 54.08 μmol). The mixture was cooled to 0° C. and NaOCl (10.1 mL, equivalent to 0.604 g, 8.112 mmol, 6 wt %) was added dropwise and the resulting mixture was vigorously stirred and allowed to warm from 0° C. to RT over 4 h. The organic layer was separated and the aqueous layer was back-extracted once with DCM. The combined organic layers were dried (Na$_2$SO$_4$), filtered and evaporated to afford 28d which was used in the next step without purification.

step B8—Sodium triacetoxyborohydride (1.47 g, 5.445 mmol) was added to a mixture of 28d (1.25 g, 4.54 mmol), 38 (Ar$^2$=4,6-dimethyl-pyrimidin-5-yl, 1.23 g, 4.994 mmol) and HOAc (0.39 ml, 6.827 mmol) in DCM (25 mL). The resulting mixture was stirred at RT for 1 h then partitioned between DCM and a saturated aqueous solution of NaHCO$_3$. The aqueous layer was back-extracted twice with DCM. The combined organic layers were dried (Na$_2$SO$_4$), filtered and evaporated. The residue was purified by SiO$_2$ chromatography eluting with a gradient of DCM/DCM-MeOH—NH$_4$OH (60/10/1) (100 to 50% DCM) to afford 1.78 (65% yield over two steps) of 30a.

step B9—To a solution of 30a (1.78 g, 3.52 mmol) in DCM (25 mL) at RT was added 4M HCl in dioxane (25 mL). The reaction mixture was left at RT for 1 h then evaporated. The white powdery residue was dried under vacuum for 24 h to afford 1.94 g (100%) of 30b as a tetrahydrochloride salt.

step B10—To a mixture of the tetrahydrochloride salt of 30b (0.055 g, 0.1 mmol) and TEA (83 mL, 0.6 mmol), THF (0.8 mL) and DMF (0.2 mL) cooled to 0° C. was added cyclopentanesulfonyl chloride (0.019 g, 0.11 mmol). The resulting suspension was stirred at 0° C. then allowed to warm to RT over 1.5 h then stirred at RT overnight. The residue was purified by SiO$_2$ chromatography eluting with a DCM/MeOH gradient (10/0.2 to 10/0.8). The recovered material was partitioned between DCM and H$_2$O. The aqueous layer was back-extracted with DCM. The combined organic layers were dried (Na$_2$SO$_4$), filtered and evaporated to give 0.024 g (45%) of II-22.

The following were prepared analogously from (4,6-dimethyl-pyrimidin-5-yl)-{5-[2-(3-phenyl-azetidin-3-yl)-ethyl]-hexahydro-pyrrolo[3,4-c]pyrrol-2-yl}-methanone using the sulfonyl chloride in parenthesis in place of cyclopentanesulfonyl chloride in the final step: II-2 (m-fluoro-phenylsulfonyl chloride), II-19 (iso-propylsulfonyl chloride) and II-20 (cyclopropyl sulfonyl chloride).

EXAMPLE 9

1-(3-{2-[5-(4,6-Dimethyl-pyrimidine-5-carbonyl)-hexahydro-pyrrolo[3,4-c]pyrrol-2-yl]-ethyl}-3-phenyl-azetidin-1-yl)-2,2-dimethyl-propan-1-one (II-7)

To a mixture of the tetrahydrochloride salt of 30b (0.055 g, 0.1 mmol), pyridine (81 μL, 1 mmol), DCM (0.5 mL) and DMF (0.2 mL) was added pivaloyl chloride (49 μL, 0.4 mmol). The resulting suspension was stirred RT for 72 h then with MeOH. The mixture was stirred at RT for 1 h then evaporated. The residue was purified by HPLC (7-10 SB-Phenyl column, 1% TFA/acetonitrile 90/10 to 10/90 in 5 minutes, 1 ml/min) to afford a material that was taken up in DCM and extracted with 0.1 M aqueous NaOH (0.2 mL). The biphasic mixture was filtered through a 0.3 mL Varian Chem Elute cartridge (CE1000M). The cartridge was rinsed three times with DCM. The filtrate was evaporated to afford 0.018 g (37%) of II-7.

The following were prepared analogously from (4,6-dimethyl-pyrimidin-5-yl)-{5-[2-(3-phenyl-azetidin-3-yl)-ethyl]-hexahydro-pyrrolo[3,4-c]pyrrol-2-yl}-methanone using the acylating agent in parenthesis in place of pivaloyl chloride in the final step: II-1 (cyclopentane carbonyl chloride), II-3 (m-fluoro-benzoyl chloride), II-4 (4-tetrahydropyranylcarbonyl chloride), II-5 (3-tetrahydrofuranylcarbonyl chloride), II-6 (cyclopentylacetyl chloride) and II-8 (3,3,3-trifluoropropionyl chloride).

II-37 was prepared analogously using [5-(3-azetidin-3-yl-3-phenyl-propyl)-hexahydro-pyrrolo[3,4-c]pyrrol-2-yl]-(2, 4-dimethyl-pyridin-3-yl)-methanone in place of (4,6-dimethyl-pyrimidin-5-yl)-{5-[2-(3-phenyl-azetidin-3-yl)-ethyl]-hexahydro-pyrrolo[3,4-c]pyrrol-2-yl}-methanone and using 3-tetrahydrofuranylcarbonyl chloride respectively in the acylation step.

EXAMPLE 10

(5-{2-[1-(3,3-Difluoro-cyclobutanecarbonyl)-3-phenyl-azetidin-3-yl]-ethyl}-hexahydro-pyrrolo[3,4-c]pyrrol-2-yl)-(4,6-dimethyl-pyrimidin-5-yl)-methanone (II-9)

To a mixture of the tetrahydrochloride salt of 30b (Ar¹=Ph, Ar²=4,6-dimethyl-pyrimidin-5-yl, 0.055 g, 0.1 mmol), 3,3-difluoro-cyclobutane-carboxylic acid (0.027 g, 0.2 mmol), EDCI (0.029 g, 0.15 mmol) and HOBt (0.02 g, 0.15 mmol) in DCM (1 mL) was added DIPEA (0.104 mL, 0.6 mmol). The resulting mixture was stirred at RT for 72 h then partitioned between DCM and water. The aqueous layer was back-extracted twice with DCM. The combined organic layers were dried (Na₂SO₄), filtered and evaporated. The residue was purified by HPLC (7-10 SB-Phenyl column, 1% TFA/acetonitrile 90/10 to 10/90 in 5 minutes, 1 ml/min) to afford a material that was dissolved in DCM and extracted with of 0.1 M NaOH (0.2 mL). The biphasic mixture was filtered through a 0.3 mL Varian Chem Elute cartridge (CE1000M). The cartridge was rinsed three times with DCM. The filtrate was evaporated to give 0.024 g (46%) of II-9.

The following were prepared analogously from (4,6-dimethyl-pyrimidin-5-yl)-{5-[2-(3-phenyl-azetidin-3-yl)-ethyl]-hexahydro-pyrrolo[3,4-c]pyrrol-2-yl}-methanone using the carboxylic acid in parenthesis in place of 3,3-difluoro-cyclobutane-carboxylic acid: II-10 (4-hydroxy-cyclohexane carboxylic acid), II-11 (4-tetrahydropyranyl-acetic acid), II-12 (2-tetrahydrofuranyl carboxylic acid), II-13 (1-methylcyclopropanylcarboxylic acid), II-14 (1-cyano-cyclopropanylcarboxylic acid), II-15 (1-trifluoromethyl-cyclopropanyl-carboxylic acid), II-16 (2,2-dimethyl-3-hydroxy-propionic acid), II-17 (1-hydroxy-cyclopropanylcarboxylic acid), II-18 (3-oxo-cyclopentanecarboxylic acid) and II-39 (4,4-difluoro-cyclohexane carboxylic acid).

II-30, II-38 and II-40 were prepared analogously using 5-[5-(3-azetidin-3-yl-3-phenyl-propyl)-hexahydro-pyrrolo[3,4-c]pyrrole-2-carbonyl]-4,6-dimethyl-pyridine-2-carbonitrile in place of (4,6-dimethyl-pyrimidin-5-yl)-{5-[2-(3-phenyl-azetidin-3-yl)-ethyl]-hexahydro-pyrrolo[3,4-c]pyrrol-2-yl}-methanone and using 3,3-difluoro-cyclobutane-carboxylic acid, tetrahydro-furan-3-carboxylic acid and 4,4-difluoro-cyclohexane-carboxylic acid, respectively in the coupling step.

(4,6-Dimethyl-pyrimidin-5-yl)-(5-{2-[1-(3-hydroxy-cyclopentanecarbonyl)-3-phenyl-azetidin-3-yl]-ethyl}-hexahydro-pyrrolo[3,4-c]pyrrol-2-yl)-methanone (II-21) was prepared by careful addition of NaBH₄ (0.01 g, 0.264 mmol) to a solution of II-18 (0.045 g, 87.27 μM) in absolute EtOH (1 mL). The resulting mixture was stirred at RT for 1 h before being evaporated. The residue was partitioned between DCM and H₂O. The aqueous layer was back extracted twice with DCM and the combined organic layers were dried (Na₂SO₄), filtered and evaporated. The residue was purified by SiO₂ chromatography eluting with DCM/MeOH (9.5/0.5) to afford 0.014 g of II-21.

EXAMPLE 11

5-{2-[1-(3,3-Difluoro-cyclobutanecarbonyl)-3-phenyl-azetidin-3-yl]-ethyl}-hexahydro-pyrrolo[3,4-c]pyrrol-2-yl)-(4,6-dimethyl-2-trifluoromethyl-pyrimidin-5-yl)-methanone (II-27)

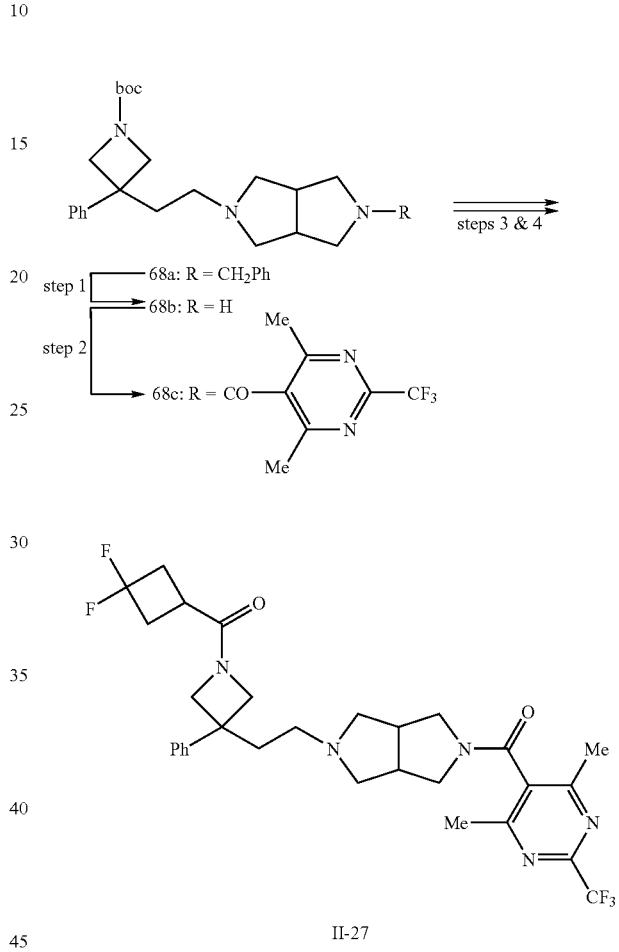

II-27

Preparation of 4,6-dimethyl-2-trifluoromethyl-pyrimidine-5-carboxylic acid step A—2-Acetyl-3-methoxy-but-2-enoic acid methyl ester (4 g, 23.23 mmol) in acetone (16 mL) was added to a solution of trifluoroacetamidine (3.47 g, 30.97 mmol) and MeOH (12 mL) cooled to 0° C. The resulting mixture was stirred RT overnight then evaporated to almost dryness. The residue was partitioned between DCM and H₂O. The aqueous layer was back extracted with DCM. The combined organic layers were washed with brine, dried (Na₂SO₄), filtered and evaporated. The residue was purified by SiO₂ chromatography eluting with an EtOAc/hexane gradient (0 to 10% EtOAc) to afford 2.42 g (44%) of 4,6-dimethyl-2-trifluoromethyl-pyrimidine-5-carboxylic acid methyl ester.

step B—A solution of KOH (1.74 g, 31.01 mmol) and water (10 mL) was added at RT to a solution of 4,6-dimethyl-2-trifluoromethyl-pyrimidine-5-carboxylic acid methyl ester (2.42 g, 10.33 mmol) in EtOH (20 mL). The resulting mixture was stirred at 40° C. overnight then cooled to RT and evaporated. The residue was partitioned between EtOAc and water. The aqueous layer was evaporated and the residue was taken up in H₂O (1 mL). Concentrated HCl was added dropwise until crystals started to form. The mixture was diluted with H₂O (5 mL) and stored in a refrigerator overnight. The crystals were filtered, rinsed with ice-cold water then ice-cold Et₂O, and dried to afford 1.5 g (66%) of 4,6-dimethyl-2-trifluoromethyl-pyrimidine-5-carboxylic acid.

The N-Boc-azetidine 68a was prepared as described in step B8 of example 8 except 38 was replaced with 16a. Hydrogenolysis of the benzyl protecting group was carried out as described in step A6 of example 1. Formation of the amide 68c was carried out as described in step A7 of example 1 except 3,5-dimethyl-pyrimidine-5-carboxylic acid was replaced by 3,5-dimethyl-2-trifluoromethyl-pyrimidine-5-carboxylic acid. Removal of the Boc protecting group was carried out as described in step B9 of example 8. Formation of the II-27 was carried out with 3,3-difluoro-cyclobutane carboxylic acid as described in example 10.

II-25 and II-26 were prepared analogously except in the final step 3,3-difluoro-cyclobutane carboxylic acid was replaced with tetrahydrofuran-3-carboxylic acid and 4,4-difluoro-cyclohexane carboxylic acid respectively.

II-34 and II-35 were prepared analogously except 3,5-dimethyl-2-trifluoromethyl-pyrimidine-5-carboxylic acid was replaced with 2,4-dimethyl-nicotinic acid (CAS Reg. No. 871492-97-6) to afford 3-{2-[5-(2,4-dimethyl-pyridine-3-carbonyl)-hexahydro-pyrrolo[3,4-c]pyrrol-2-yl]-ethyl}-3-phenyl-azetidine-1-carboxylic acid tert-butyl ester which was deprotected and acylated using 4,4-difluoro-cyclohexane-carboxylic acid and 3,3-difluoro-cyclobutane-carboxylic acid respectively in the coupling step as described above.

II-33 was prepared analogously except 3,5-dimethyl-2-trifluoromethyl-pyrimidine-5-carboxylic acid was replaced with 2,4-dimethyl-6-oxo-6H-pyran-3-carboxylic acid to afford 3-{2-[5-(2,4-dimethyl-6-oxo-6H-pyran-3-carbonyl)-hexahydro-pyrrolo[3,4-c]pyrrol-2-yl]-ethyl}-3-phenyl-azetidine-1-carboxylic acid tert-butyl ester was deprotected and acylated using 4,4-difluoro-cyclohexane-carboxylic acid in the coupling step as described above.

EXAMPLE 12

5-{2-[3-(3-Chloro-phenyl)-1-(3,3-difluoro-cyclobutanecarbonyl)-azetidin-3-yl]-ethyl}-hexahydro-pyrrolo[3,4-c]pyrrol-2-yl)-(4,6-dimethyl-pyrimidin-5-yl)-methanone (II-29)

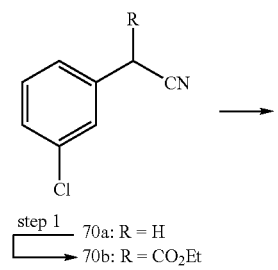

step 1— 70a: R = H
70b: R = CO₂Et

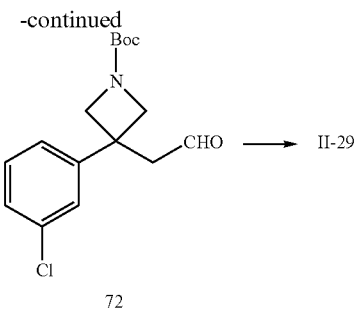

72 step 1—A solution 3-chlorobenzyl cyanide (10 g, 66 mmol) dissolved in diethyl carbonate (80 mL) was added over 15 min to a suspension of NaH (8.7 g, 0.218 mol, 60% dispersion in oil) in THF (70 mL) cooled to 0° C. The resulting mixture was stirred at RT for 12 h, heated at reflux for 14 h then cooled to RT and quenched with H₂O. The reaction mixture was partitioned between Et₂O and H₂O and the aqueous layer was adjusted to pH 3 with 2M aqueous HCl and thrice back-extracted with Et₂O. The combined organic layers were washed with water, brine, dried (Na₂SO₄), filtered and evaporated to afford 10.1 g (68% yield) of (3-chlorophenyl)-cyano-acetic acid ethyl ester which was used in the next step without purification.

3-(3-Chloro-phenyl)-3-(2-oxo-ethyl)-azetidine-1-carboxylic acid tert-butyl ester (72) was prepared from 70b according to the same procedures used for the synthesis of 28d in steps 1-7 of example 8. Reductive amination of 72 and 38 (Ar²=4,6-dimethyl-pyrimidin-5-yl) as described in step B8 followed by removal of the Boc protecting group as described in step B9 of example 8 afforded the requisite azetidine which was converted to II-29 with 3,3-difluoro-cyclobutane carboxylic acid as described in Example 10.

II-28 was prepared analogously except in the final step 3,3-difluoro-cyclobutane carboxylic acid was replaced with 4,4-difluoro-cyclohexane carboxylic acid.

EXAMPLE 13

(4,6-Dimethyl-pyrimidin-5-yl)-{5-[3-(3-fluoro-phenyl)-3-(1-methanesulfonyl-piperidin-4-yl)propyl]-hexahydro-pyrrolo[3,4-c]pyrrol-2-yl}-methanone (V-26)

SCHEME E (Ar¹=3-fluoro-phenyl, Ar²=4,6-dimethyl-pyrimidin-5-yl)

step E1—A dioxane solution of HCl (100 mL, 4.0 M) and 50a was (7.7 g, 37 mmol) was stirred for 90 min at RT. The solvent was removed in vacuo to afford 50b [R═H, ms (LCMS) m/z 111 (M+H−Boc)] which was dried under high vacuum, and used without further purification in the next reaction. TEA (21 mL, 149 mmol) and benzyl bromide (5.4 mL, 45 mmol) were added to a slurry of the white solid in MeCN (120 mL) maintained at 0° C. The reaction mixture was stirred for 12 h and allowed to warm to RT. The reaction mixture was quenched by the addition of water at 0° C. and extracted with EtOAc. The combined organic extracts were dried (Na₂SO₄) and concentrated. The crude product was purified by SiO₂ chromatography eluting with a gradient of DCM and DCM/MeOH/NH₄OH (60/10/1) (98 to 85% DCM over 60 min) to afford 5 g (68%) of 50b: ms (LCMS) m/z 201 (M+H).

step E2—A solution of 50b (5 g, 25 mmol) in THF (80 mL) was added dropwise to a solution of 3-fluoro-phenylmagnesium bromide (34 mL, 1.0 M, 34 mmol) in THF (20 mL) maintained at 0° C. The reaction mixture was stirred for 72 h and allowed to warm to RT. The reaction was quenched by the addition of saturated aqueous $NH_4Cl$, extracted with EtOAc, dried ($Na_2SO_4$) and concentrated. EtOH (50 mL) was added and the pH was adjusted to pH 11-14 with aqueous NaOH. The mixture was heated to 60° C. for 3 h, brine was added and the mixture was extracted with EtOAc. The combined organic extracts were dried ($Na_2SO_4$) and concentrated. The crude product was purified by $SiO_2$ chromatography eluting with a gradient of DCM and DCM/MeOH/$NH_4OH$ (60/10/1) (95 to 85% DCM over 60 min) to afford 4.4 g (59%) of 52: ms (LCMS) m/z 298 (M+H).

step E3—(Diethoxy-phosphoryl)-acetic acid ethyl ester (6.5 mL, 32 mmol) was added dropwise to a slurry of NaH (1.24 g, 31 mmol, 60% dispersion in mineral oil) in THF (10 mL) maintained at 0° C. After the addition was complete, the ice bath was removed and the solution was stirred at RT for 20 min. To this solution was added 52 (4.4 g, 15 mmol) in THF (40 mL) and the reaction mixture was stirred at 50-60° C. for 12 h. The reaction mixture was cooled to RT, aqueous $NH_4Cl$ was added and the mixture was extracted with EtOAc. The combined organic extracts were dried ($Na_2SO_4$) and concentrated. The crude product was purified by $SiO_2$ chromatography eluting with an EtOAc/hexane gradient (5% to 15% EtOAc over 60 min) to afford and 4.9 g (90%) of an E/Z mixture of 54: m/z 368 (M+H).

step E4—To a solution of 54 (3, 4.9 g, 13 mmol) in EtOH (40 mL) was added Pd(OH)$_2$/C (1 g, 20 wt % Pd/C, wet) and the reaction mixture was stirred under an $H_2$ atmosphere for 36 h, filtered through CELITE®, concentrated, and dried under high vacuum. Aqueous NaOH (20 mL, 2M, 40 mmol) and a solution of (BOC)$_2$O (4.5 g, 21 mmol) in THF (20 mL) were added to a solution of the above residue in THF (80 mL) maintained at 0° C. The mixture was stirred for 12 h at 0° C. and then warmed to RT. The mixture was extracted with EtOAc, and the combined organic extracts were dried ($Na_2SO_4$), concentrated and purified by $SiO_2$ chromatography eluting with an EtOAc/hexane gradient (5% to 95% EtOAc over 50 min) to afford 4.2 g (85%) of 56a.

step E5—DIBAL-H (1.4 mL, 1.0 M in DCM, 1.4 mmol) was added dropwise to a solution of 56a (260 mg, 0.69 mmol) in DCM (6 mL) maintained at −78° C. The reaction mixture was stirred for 1 h then quenched by the addition of MeOH. The pH was adjusted to pH 3 by the addition of 1N HCl. The mixture was extracted with DCM. The combined organic extracts were dried ($Na_2SO_4$) and concentrated to afford 56b which was used without further purification in the next step.

step E6—NaHB(OAc)$_3$ (166 mg, 0.78 mmol) was added to a solution of 56b from the previous step, 38 (Ar$^2$=4,6-dimethyl-pyrimidin-5-yl, 205 mg, 0.83 mmol) and HOAc (0.2 mL, 3.5 mmol) in DCM (6 mL) maintained at 0° C. The reaction mixture was stirred and warmed to RT. The mixture was quenched at 0° C. by the addition of NaOH (2N, until pH 11), extracted with DCM, dried ($Na_2SO_4$) and concentrated. The crude product was purified by $SiO_2$ column chromatography eluting with a gradient of DCM and DCM/MeOH/$NH_4OH$ (60/10/1) (98 to 75% DCM over 60 min) to afford 0.258 g (67%) of 58a: ms (LCMS) m/z 566 (M+H).

step E7—TFA (1 mL) was added to 58a (38 mg, 0.067 mmol) and the mixture was stirred at RT for 1 h. The solvent was removed, and the residue was dried under high vacuum. To the residue from the TFA treatment, Et$_3$N (13 μL, 0.092 mmol) in THF (1 mL) maintained at 0° C. was added methanesulfonyl chloride (7 μL, 0.090 mmol). The reaction mixture was stirred and allowed to warm to RT. The crude product was purified by $SiO_2$ preparative TLC developing with a mixture of DCM and DCM/MeOH/$NH_4OH$ (60/10/1) (45% DCM) to afford 0.016 g (44%) of V-26.

The following were prepared analogously using the sulfonyl chloride in parenthesis: V-27 (2-pyridinylsulfonyl chloride, V-28 (N,N-dimethylaminosulfamoyl chloride) and V-29 and V-30 (methansulfonyl chloride, the enantiomers were separated by with a chiral HPLC column).

The following were prepared analogously using (4,6-dimethyl-pyrimidin-5-yl)-[5-(3-phenyl-3-piperidin-4-yl-propyl)-hexahydro-pyrrolo[3,4-c]pyrrol-2-yl]-methanone in place of (4,6-dimethyl-pyrimidin-5-yl)-{5-[3-(3-fluoro-phenyl)-3-piperidin-4-yl-propyl]-hexahydro-pyrrolo[3,4-c]pyrrol-2-yl}-methanone and using the sulfonyl chloride in parenthesis in place of methansulfonyl chloride: V-8 (phenylsulfonyl chloride), V-9 (iso-propyl sulfonyl chloride), V-10 (phenylmethanesulfonyl chloride), V-11 (ethylsulfonyl chloride), V-12 (methanesulfonyl chloride). V-18 (cyclopentanesulfonyl chloride), V-20 (cyclopropanesulfonyl chloride) and V-23 (3,3,3-trifluoroethylsulfonyl chloride).

EXAMPLE 14

5-{5-[3-(1-Methanesulfonyl-piperidin-4-yl)-3-phenyl-propyl]-hexahydro-pyrrolo[3,4-c]pyrrole-2-carbonyl}-4,6-dimethyl-pyridine-2-carbonitrile (V-24)

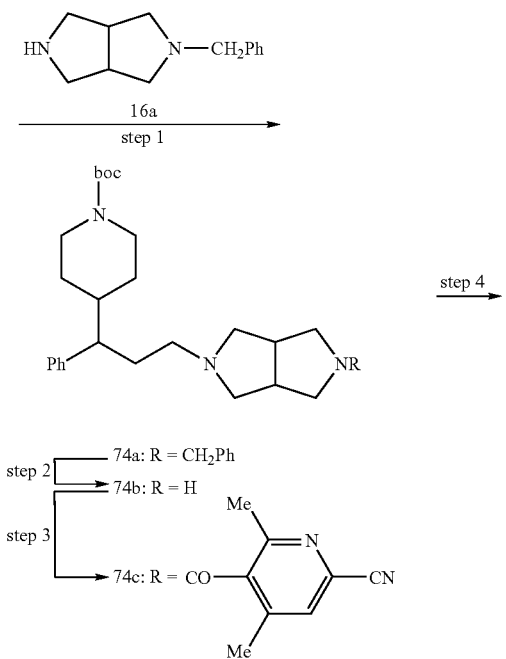

-continued

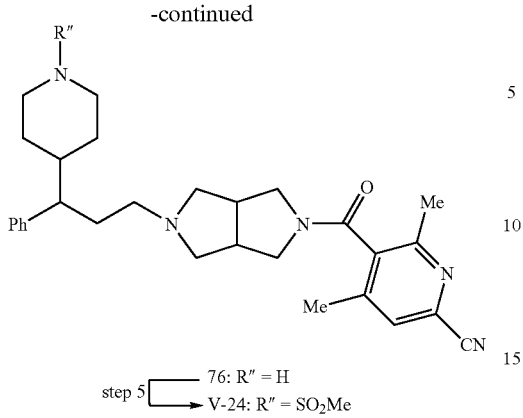

step 5 ⎡ 76: R″ = H
        ⎣ V-24: R″ = SO₂Me

Compound 56b (Ar¹=Ph) was obtained by a sequence similar to the one outlined in Scheme E starting from the commercially available hydrochloride salt of phenyl-piperidin-4-yl-methanone (73). The secondary amine was protected with a Boc group, homologation of the ketone with (diethoxy-phosphoryl)-acetic acid ethyl ester, reduction of the olefin and reduction of the ester to the aldehyde affords 56b step 1—To a solution of 56b (Ar¹=Ph, 537 mg, 1.69 mmol), 2-benzyl-octahydro-pyrrolo[3,4-c]pyrrole (16a, 380 mg, 1.88 mmol), HOAc (0.4 mL, 6.99 mmol) and DCM (10 mL) maintained at 0° C. was added NaHB(OAc)₃ (380 mg, 1.79 mmol). The reaction mixture was stirred and allowed to warm to RT. The mixture was quenched at 0° C. by the addition of NaOH (2N, until the pH was approximately 11), extracted with DCM, dried (Na₂SO₄) and concentrated. The crude product was purified by SiO₂ chromatography eluting with a gradient of DCM and DCM/MeOH/NH₄OH (60/10/1) (95 to 70% DCM over 50 min) to afford 0.400 g (47%) of 74a: ms (LCMS) m/z 504 (M+H).

steps 2 & 3—Pd(OH)₂/C (100 mg, 20 wt % Pd/C, wet) was added to a solution of 74a (230 mg, 0.46 mmol) in EtOH (6 mL). The reaction mixture was stirred under an H₂ atmosphere for 24 h, filtered through CELITE®, concentrated, and dried in vacuo. The crude product [ms (LCMS) m/z 414 (M+H)] was used without further purification in the next reaction. To a solution of 74b (85 mg, 0.21 mmol), 6-cyano-2,4-dimethyl-nicotinic acid (37 mg, 0.21 mmol), HOBt (40 mg, 0.30 mmol) and EDCI (47 mg, 0.25 mmol) in CH₂Cl₂ (1 mL) maintained at 0° C. was added TEA (0.06 mL, 0.43 mmol). The reaction mixture was stirred for 36 h and warmed to RT. The reaction mixture was quenched by the addition of saturated aqueous NaHCO₃, extracted with DCM, dried (Na₂SO₄) and concentrated. The crude product was purified by SiO₂ chromatography eluting with a gradient of DCM and DCM/MeOH/NH₄OH (60/10/1) (95 to 75% DCM over 50 min) to afford 0.035 g (30%) of 74c: ms (LCMS) m/z 572 (M+H).

steps 4 & 5—TFA (1 mL) was added to 74c (30 mg, 0.053 mmol). The mixture was stirred at RT for 1 h. The solvent was removed and residual TFA was removed by coevaporation with toluene. Methanesulfonyl chloride (5 μL, 0.064 mmol) was added to a solution of the residue and TEA (9 μL, 0.065 mmol) in THF (1 mL) maintained at 0° C. The reaction mixture was stirred and warmed to RT. The crude product was purified by prep TLC and developed with a mixture of 45% DCM and 55% of DCM/MeOH/NH₄OH (60/10/1) to afford 0.019 g (66%) of V-24.

EXAMPLE 15

(5-{3-[1-(2,2-Difluoro-ethyl)-piperidin-4-yl]-3-phenyl-propyl}-hexahydro-pyrrolo[3,4-c]pyrrol-2-yl)-(4,6-dimethyl-pyrimidin-5-yl)-methanone (V-1)

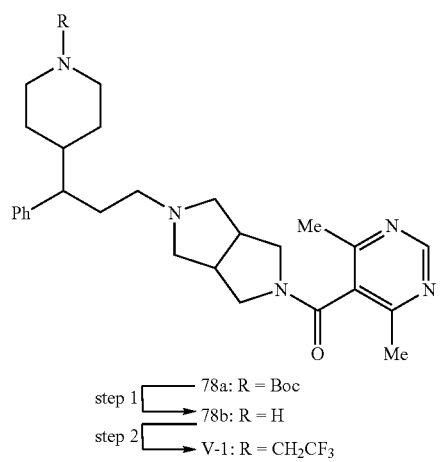

step 1 ⎡ 78a: R = Boc
       ⎣ 78b: R = H
step 2 ⎣ V-1: R = CH₂CF₃

4-{3-[5-(4,6-Dimethyl-pyrimidine-5-carbonyl)-hexahydro-pyrrolo[3,4-c]pyrrol-2-yl]-1-phenyl-propyl}-piperidine-1-carboxylic acid tert-butyl ester (78a) was prepared from commercially available hydrochloride salt of phenyl-piperidin-4-yl-methanone by a sequence outlined in example 14 except 38 (Ar²=4,6-dimethyl-pyrimidin-5-yl) was used in place of 16a in the reductive amination.

steps 1 & 2—TFA (1 mL) was added to 78a (40 mg, 0.073 mmol) and the mixture was stirred at RT for 45 min. The solvent was removed, and the residue was dried under high vacuum. 2,2,2-Trifluoro-ethyl trifluoro-methanesulfonate (23 mg, 0.11 mmol) was added to a solution of the residue, TEA (19 μL, 0.14 mmol) and THF (1 mL) maintained at 0° C. The reaction mixture was stirred and warmed RT. The crude product was purified on a preparative TLC plate developed with a mixture of 45% DCM and 55% of DCM/MeOH/NH₄OH (60/10/1) to afford 0.015 g (40%) of V-1.

V-21 and V-31 were prepared analogously using 2,2-difluoro-ethyl trifluoromethansulfonate and bromoacetonitrile respectively in the final step.

V-25 was prepared analogously using (4,6-dimethyl-pyrimidin-5-yl)-{5-[3-(3-fluoro-phenyl)-3-piperidin-4-yl-propyl]-hexahydro-pyrrolo[3,4-c]pyrrol-2-yl}-methanone in place of (4,6-dimethyl-pyrimidin-5-yl)-[5-(3-phenyl-3-piperidin-4-yl-propyl)-hexahydro-pyrrolo[3,4-c]pyrrol-2-yl]-methanone.

II-23 and II-24 were prepared analogously by alkylation of 30b (Ar¹=Ph and Ar²=4,6-dimethyl-pyrimidin-5-yl with 2,2,2-trifluoro-ethyl trifluoro-methanesulfonate and 2,2-difluoro-ethyl trifluoromethansulfonate, respectively.

EXAMPLE 16

4-{3-[5-(4,6-Dimethyl-pyrimidine-5-carbonyl)-hexahydro-pyrrolo[3,4-c]pyrrol-2-yl]-1-phenyl-propyl}-piperidine-1-carboxylic acid 3-hydroxy-cyclopentyl ester (V-6)

A solution of HCl-dioxane (1 mL, 4.0 M) and 78a (35 mg, 0.064 mmol) was stirred at RT for 90 min. The solvent was removed, and the residue was dried in vacuo. Cyclopentane-1,3-diol (cis/trans, 9 μL, 0.096 mmol) was added to a solution of N,N'-disuccimidylcarbonate (30 mg, 0.12 mmol) and TEA (44 μL, 0.32 mmol) in MeCN (0.47 mL) and the solution was stirred for 4 h. A solution of the above residue from the Boc deprotection in MeCN was added and the reaction mixture was stirred for 3 h. The solvent was evaporated and the crude product was purified on a preparative TLC plate developed with a mixture of 45% DCM and 55% of DCM/MeOH/NH$_4$OH (60/10/1) to afford 0.011 g (30%) of V-6.

EXAMPLE 17

1-(4-{3-[5-(4,6-Dimethyl-pyrimidine-5-carbonyl)-hexahydro-pyrrolo[3,4-c]pyrrol-2-yl]-1-phenyl-propyl}-piperidin-1-yl)-2-methyl-propan-1-one (V-15)

A solution of HCl-dioxane (1 mL, 4.0 M) and 78a (39 mg, 0.071 mmol) and the mixture was stirred at RT for 1 h. The solvent was removed, and the residue was dried in vacuo. Pivaloyl chloride (13 mg, 0.11 mmol) was added to a solution of the residue and Et$_3$N (15 μL, 0.11 mmol) in DCM (0.5 mL) maintained at 0° C. The reaction mixture was stirred for 36 h and then warmed RT. The mixture was quenched by the addition of saturated aqueous Na$_2$CO$_3$, filtered, extracted with DCM, and the extracts were concentrated. The crude product was purified by HPLC (7-10 SB-Phenyl column, water/acetonitrile 90/10 to 10/90 in 5 minutes, 1 ml/min) to afford V-15.

The following were prepared analogously from (4,6-dimethyl-pyrimidin-5-yl)-[5-(3-phenyl-3-piperidin-4-yl-propyl)-hexahydro-pyrrolo[3,4-c]pyrrol-2-yl]-methanone using the acylating agent in parenthesis in place of pivaloyl chloride: V-13 (propionyl chloride), V-14 (3-methyl-butyryl chloride), V-19 (isobutyryl chloride), V-16 (methoxyacetyl chloride), V-17 (cyclopentylacetyl chloride) and V-22 (TFAA).

EXAMPLE 18

(4,6-Dimethyl-pyrimidin-5-yl)-{5-[3-(1-methanesulfonyl-azetidin-3-yl)-3-phenyl-propyl]-hexahydro-pyrrolo[3,4-c]pyrrol-2-yl}-methanone (IV-7)

SCHEME D (Ar$^1$=phenyl, Ar$^2$=4,6-dimethyl-pyrimidin-5-yl)

step 1—A solution of nitrile 42a (19 g, 77 mmol) in PhH (300 mL) was added dropwise to a solution of phenylmagnesium bromide (100 mL, 1.0 M in THF, 100 mmol) in PhH (100 mL) maintained at 0° C. The reaction mixture was stirred for 12 h and warmed to RT. The reaction was quenched by the addition of saturated aqueous NH$_4$Cl at 0° C., extracted with EtOAc, dried (Na$_2$SO$_4$) and concentrated. EtOH (400 mL) was added and the pH was adjusted to pH 11-14 with aqueous NaOH. The mixture was heated to 60° C. for 3 h, and then stirred at RT overnight. Brine was added and the mixture was extracted with EtOAc. The combined organic extracts were dried (Na$_2$SO$_4$) and concentrated. The crude product was purified by SiO$_2$ chromatography eluting with an EtOAc/hexane gradient (5 to 15% EtOAc over 50 min) to afford 14.6 g (58%) of 42b: ms (LCMS) m/z 328 (M+H).

step 2—(Diethoxy-phosphoryl)-acetic acid ethyl ester (19 mL, 95 mmol) was added dropwise to a slurry of NaH (3.29 g, 82 mmol, 60% dispersion in mineral oil) in THF (70 mL) maintained at 0° C. After the addition was complete, the ice bath was removed and the solution was stirred at RT for 20 min. A solution of 42b (14.6 g, 45 mmol) in THF (100 mL) was added, and the reaction mixture was stirred at 50-60° C. for 72 h. The reaction mixture was cooled to RT, brine was added and the mixture was extracted with EtOAc. The combined organic extracts were dried (Na$_2$SO$_4$) and concentrated. The crude product was purified by SiO$_2$ chromatography eluting with an EtOAc/hexane gradient (5 to 15% EtOAc over 50 min) to afford 17.4 g (98%) of 44 as an E/Z mixture: ms (LCMS) m/z 398 (M+H).

step 3—To a solution of 44 (17.4 g, 44 mmol) in EtOH (400 mL) was added Pd(OH)$_2$/C (2 g, 20 wt % Pd/C, wet). The reaction mixture was stirred under an H$_2$ atmosphere for 12 h, filtered through CELITE®, concentrated, and dried in vacuo. Aqueous NaOH (70 mL, 2M, 140 mmol) and a solution of BOC$_2$O (18.4 g, 84 mmol) in THF (100 mL) were added to a solution of the above residue from the hydrogenation and THF (300 mL) maintained at 0° C. The mixture was stirred for 12 h and warmed to RT. The mixture was extracted with EtOAc, and the combined organic extracts were dried (Na$_2$SO$_4$), concentrated and purified by SiO$_2$ chromatography eluting with an EtOAc/hexane gradient (5 to 15% EtOAc over 50 min) to afford 6.9 g (47%) of 46a.

step 4—To a solution of 46a (2.05 g, 6.2 mmol) in DCM (60 mL) maintained at −78° C. was added dropwise a solution of DIBAL-H (29 mL, 1.0 M in DCM, 29 mmol). The reaction mixture was stirred for 12 h at RT. The reaction mixture was quenched by the addition of Rochelle's salt and extracted with DCM. The combined organic extracts were dried (Na$_2$SO$_4$), concentrated, and purified by SiO$_2$ chromatography eluting with an EtOAc/hexane gradient (1 to 5% EtOAc over 40 min) to afford 0.200 g (11%) of 46b.

steps 5 & 6—Commercial bleach (1.2 mL) was added to a vigorously stirred mixture of 46b (200 mg, 0.69 mmol), NaHCO$_3$ (30 mg, 0.36 mmol), TEMPO (2,2,6,6-tetramethylpiperidine-N-oxyl, 6 mg, 0.04 mmol), DCM (4 mL) and H$_2$O (4 mL) maintained at 0° C. The reaction mixture was stirred for 4 h and allowed to warm to RT. Brine was added and the mixture was extracted with DCM. The combined organic extracts were dried (Na$_2$SO$_4$) and concentrated. The aldehyde 46c was used without further purification. NaHB(OAc)$_3$ (155 mg, 0.73 mmol) was added to a solution of the 46c, 38 (Ar$^2$=4,6-dimethyl-pyrimidin-5-yl, 200 mg, 0.81 mmol) and HOAc (0.2 mL, 3.5 mmol) in DCM (3 mL) maintained at 0° C. The reaction mixture was stirred for 12 h and warmed to RT. The mixture was quenched at 0° C. by the addition of NaOH (2N, until pH 13), extracted with DCM, dried (Na$_2$SO$_4$) and concentrated. The crude product was purified by SiO$_2$ chromatography eluting with a gradient of DCM and DCM/MeOH/NH$_4$OH (60/10/1) (95 to 70% DCM over 50 min) to afford 0.260 g (73%) of 48a (Ar$^1$=Ph and Ar$^2$=4,6-dimethyl-pyrimidin-5-yl): ms (LCMS) m/z 520 (M+H).

steps 7 & 8—TFA (1 mL) was added to 48a (30 mg, 0.058 mmol) and the mixture was stirred at RT for 30 min. The solvent was removed, and the residue was dried in vacuo. Methanesulfonyl chloride (0.01 mL, 0.13 mmol) was added to a solution of the residue from the deprotection and Et$_3$N (0.03 mL, 0.21 mmol) in DCM (0.8 mL) maintained at 0° C. The reaction mixture was stirred for 12 h and warmed to RT. The mixture was quenched at 0° C. by the addition of saturated aqueous NaHCO$_3$, extracted with DCM, dried (Na$_2$SO$_4$) and concentrated. The crude product was purified by HPLC (7-10 SB-Phenyl column, water/acetonitrile 90/10 to 10/90 in 5 minutes, 1 ml/min) to afford 0.017 g (60%) of IV-7 as TFA salt: ms (LCMS) m/z 498 (M+H).

The following were prepared analogously using the sulfonyl chloride in parenthesis in place of methansulfonyl chloride: IV-6 (iso-propyl sulfonyl chloride), IV-8 (cyclopentanesulfonyl chloride), IV-9 (cyclopropanesulfonyl chloride) and IV-11 (2-methyl-propane-1-sulfonyl chloride).

The following were prepared analogously using (4,6-dimethyl-pyrimidin-5-yl)-(5-{2-[3-(3-fluoro-phenyl)-azetidin-3-yl]-ethyl}-hexahydro-pyrrolo[3,4-c]pyrrol-2-yl)-methanone in place of (4,6-dimethyl-pyrimidin-5-yl)-{5-[2-(3-phenyl-azetidin-3-yl)-ethyl]-hexahydro-pyrrolo[3,4-c]pyrrol-2-yl}-methanone and using the sulfonyl chloride in parenthesis: IV-14 (m-fluoro-benzenesulfonyl chloride), IV-15 (cyclopentanesulfonyl chloride), IV-16 (cyclopropanesulfonyl chloride), IV-17 (2-pyridinylsulfonyl chloride) and IV-18 (ClS(O)$_2$NMe$_2$).

The following were prepared analogously using 4,6-dimethyl-5-{5-[2-(3-phenyl-azetidin-3-yl)-ethyl]-hexahydro-pyrrolo[3,4-c]pyrrole-2-carbonyl}-pyridine-2-carbonitrile and the sulfonyl chloride in parenthesis in place of methansulfonyl chloride in the final step: IV-12 (cyclopropanesulfonyl chloride) and IV-13 (cyclopentanesulfonyl chloride).

EXAMPLE 19

(4,6-Dimethyl-pyrimidin-5-yl)-(5-{3-phenyl-3-[1-(2,2,2-trifluoro-ethyl)-azetidin-3-yl]-propyl}hexahydro-pyrrolo[3,4-c]pyrrol-2-yl)-methanone (IV-3)

TFA (1 mL) was added to 48a (30 mg, 0.058 mmol, Ar$^1$=Ph, Ar$^2$=4,6-dimethyl-pyrimidin-5-yl). The mixture was stirred at RT for 30 minutes. The solvent was removed, and the residue was dried in vacuo. 2,2,2-Trifluoro-ethyl trifluoromethanesulfonate (0.02 mL, 0.14 mmol) was added to a solution of the residue from the deprotection, TEA (0.03 mL, 0.21 mmol) and MeCN (0.8 mL) maintained at 0° C. The reaction mixture was stirred for 12 h and warmed to RT. The mixture was quenched at 0° C. by the addition of saturated aqueous NaHCO$_3$, extracted with DCM, dried (Na$_2$SO$_4$) and concentrated. The crude product was purified by SiO$_2$ chromatography eluting with a gradient of DCM and DCM/MeOH/NH$_4$OH (60/10/1) (99 to 95% DCM over 50 min) to afford 0.009 g (30%) of IV-3: ms (LCMS) m/z 502 (M+H).

IV-20 was prepared analogously but bromoacetonitrile was used in place of 2,2,2-trifluoro-ethyl trifluoromethanesulfonate

EXAMPLE 20

{5-[3-(1-Cyclopentanecarbonyl-azetidin-3-yl)-3-phenyl-propyl]-hexahydro-pyrrolo[3,4-c]pyrrol-2-yl}-(4,6-dimethyl-pyridin-5-yl)-methanone (IV-2)

TFA (1 mL) was added to 48a (30 mg, 0.058 mmol). The mixture was stirred at RT for 30 minutes. The solvent was removed, and the residue was concentrated in vacuo. Cyclopentanecarbonyl chloride (0.01 mL, 0.082 mmol) was added to a solution of the residue from the deprotection, TEA (0.03 mL, 0.21 mmol) and DCM (0.8 mL) maintained at 0° C. The reaction mixture was stirred for 12 h at RT. The mixture was quenched at 0° C. by the addition of saturated aqueous NaHCO$_3$, extracted with DCM, dried (Na$_2$SO$_4$) and concentrated. The crude product was purified by SiO$_2$ chromatography eluting with a gradient of DCM and DCM/MeOH/NH$_4$OH (60/10/1) (99 to 95% DCM over 50 min) to afford 0.022 g (74%) of IV-2: ms (LCMS) m/z 516 (M+H).

IV-4, IV-10 and IV-19 were prepared analogously using 3-methyl-butyryl chloride, isobutyryl chloride and acetic anhydride respectively in place of cyclopentanecarbonyl chloride.

EXAMPLE 21

(5-{3-[1-(3,3-Difluoro-cyclobutanecarbonyl)-azetidin-3-yl]-3-phenyl-propyl}-hexahydro-pyrrolo[3,4-c]pyrrol-2-yl)-(4,6-dimethyl-pyrimidin-5-yl)-methanone (IV-5)

TFA (1 mL) was added to 48a (30 mg, 0.058 mmol) and the resulting solution was stirred at RT for 30 min. The solvent was removed, and the residue was dried in vacuo. TEA (0.03 mL, 0.21 mmol) was added to a solution of the residue, 3,3-difluoro-cyclobutanecarboxylic acid (14 mg, 0.10 mmol), HOBt (14 mg, 0.10 mmol), EDCI (13 mg, 0.067 mmol) and DCM (0.8 mL) maintained at 0° C. The reaction mixture was stirred for 12 h at RT. The mixture was quenched at 0° C. by the addition of saturated aqueous NaHCO$_3$, extracted with DCM, dried (Na$_2$SO$_4$) and concentrated. The crude product was purified on a preparative TLC plate developed with a 1:1 mixture of DCM and DCM/MeOH/NH$_4$OH (60/10/1) to afford 0.018 g (58%) of IV-5: ms (LCMS) m/z 538 (M+H).

EXAMPLE 22

4-{3-[5-(4,6-Dimethyl-pyrimidine-5-carbonyl)-hexahydro-pyrrolo[3,4-c]pyrrol-2-yl]-1-phenyl-propyl}-piperidine-1-carboxylic acid methyl ester (V-7)

HCl-dioxane (1 mL, 4.0 M) was added to 78a (Ar$^1$=Ph, Ar$^2$=4,6-dimethyl-pyrimidin-5-yl, 40 mg, 0.073 mmol). The mixture was stirred at RT for 90 min. The solvent was removed, and the residue was dried in vacuo. Methyl chloroformate (8 μL, 0.10 mmol) was added to a solution of the residue from the deprotection, TEA (16 μL, 0.11 mmol) in DCM (0.5 mL) maintained at 0° C. The reaction mixture was stirred and warmed to RT. The crude product was purified on a preparative TLC plate developed with a 45:55 mixture of DCM and DCM/MeOH/NH$_4$OH (60/10/1) to afford 0.004 g (11%) of V-7.

EXAMPLE 23

4-{3-[5-(4,6-Dimethyl-pyrimidine-5-carbonyl)-hexahydro-pyrrolo[3,4-c]pyrrol-2-yl]-1-phenyl-propyl}-piperidine-1-carboxylic acid isopropylamide (V-3)

HCl-dioxane (1 mL) was added to 78a (Ar$^1$=Ph, Ar$^2$=4,6-dimethyl-pyrimidin-5-yl, 40 mg, 0.073 mmol). The mixture was stirred at RT for 1 h. The solvent was removed, and the residue was dried in vacuo. 2-Isocyanato-propane (34 μL, 0.35 mmol) was added to a solution of the residue from the deprotection, TEA (36 μL, 0.26 mmol) and DCM (0.5 mL) maintained at 0° C. The reaction mixture was stirred and warmed to RT. The mixture was quenched by the addition of water (1 mL), filtered, rinsed with CH$_2$Cl$_2$, and concentrated. The crude product was purified on a preparative TLC plate developed with a 45:55 mixture of DCM and DCM/MeOH/NH$_4$OH (60/10/1) to afford 0.010 g (26%) of V-3.

V-2, V4 and V5 were prepared analogously from (4,6-dimethyl-pyrimidin-5-yl)-[5-(3-phenyl-3-piperidin-4-yl-propyl)-hexahydro-pyrrolo[3,4-c]pyrrol-2-yl]-methanone using 2-isocyanato-2-methyl-propane, isocyanato ethane and isocyanato cyclopentane respectively.

EXAMPLE 24

(5-{2-[1-(4,4-Difluoro-cyclohexanecarbonyl)-3-phenyl-azetidin-3-yl]-ethyl}-hexahydro-pyrrolo[3,4-c]pyrrol-2-yl)-(2,4-dimethyl-6-trifluoromethyl-pyridin-3-yl)-methanone (II-31)

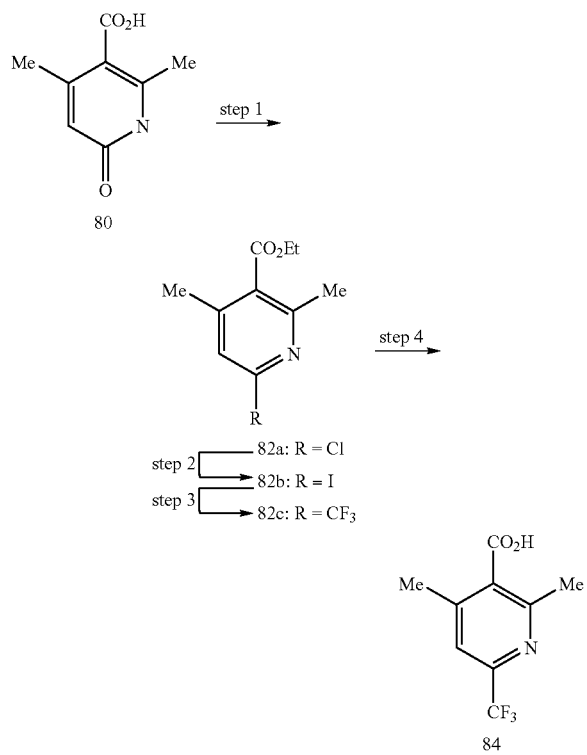

step 1—A suspension of 80 (5 g, 29.9 mmol) in 50 ml of POCl$_3$ was stirred at 80° C. overnight, cooled to RT and carefully evaporated. The residue was cooled to 0° C. and EtOH (20 mL) was dropwise. The mixture was stirred at RT for 30 min then partitioned between EtOAc and H$_2$O. The aqueous layer was back extracted with EtOAc. Combined organic layers were washed with brine, dried (Na$_2$SO$_4$), filtered and evaporated. The residue was purified by SiO$_2$ chromatography eluting with an EtOAc/hexane gradient (0 to 10% EtOAc) to afford 82a.

step 2—A mixture of 82a (1 g, 4.68 mmol), NaI (2.09, 13.94 mmol), TMSCl (0.59 ml, 4.67 mmol) in propionitrile (10 mL) was stirred at 60° C. for 1 h and then at 75° C. for 3.5 h before being cooled to RT and partitioned between EtOAc and saturated aqueous NaHCO$_3$. The aqueous layer was back extracted with EtOAc and the combined organic layers were dried (Na$_2$SO$_4$), filtered and evaporated. The residue was purified by SiO$_2$ chromatography eluting with an EtOAc/hexane gradient (0 to 5% EtOAc) to afford 1.26 g of 6-iodo-2,4-dimethyl-nicotinic acid ethyl ester (coeluting with about 15% of 82a).

step 3—A mixture of Cu(I)I (0.774 g, 4.06 mmol) and previously dried and ground-up KF (0.236 g, 4.06 mmol) was heated with a heat gun under high vacuum until it became an evenly green powder. The powder was cooled to RT before adding 6-iodo-2,4-dimethyl-nicotinic acid ethyl ester (1.26 g, 4.13 mmol, not corrected for impurity vide supra) in NMP (10 mL) and TMSCF$_3$ (0.61 ml, 4.12 mmol). The resulting mixture was stirred at 70° C. overnight, cooled to RT and poured into a 12% aqueous NH$_4$OH solution. The solution was back extracted with Et$_2$O. The combined organic layers were washed twice with the 12% aqueous NH$_4$OH solution and with brine, dried (Na$_2$SO$_4$), filtered and evaporated. The product could only be isolated from the unreacted halopyridines after hydrogenolysis (190 mg 10% Pd/C, HOAc (0.5 mL), EtOH (10 mL), 40 psi H$_2$, 48 h). The mixture was filtered and the cake was rinsed with MeOH and the filtrate was evaporated. The residue was purified by SiO$_2$ chromatography eluting with an EtOAc/hexane gradient (0 to 5% EtOAc) to afford 0.405 g (44% yield over two steps) of 82c.

step 4—A solution of KOH (0.272 g, 4.85 mmol) in H$_2$O (4 mL) was added at RT to a solution of 82c (0.4 g, 1.62 mmol) in EtOH (8 mL). The resulting mixture was stirred at 40° C. for 24 h, cooled to RT and evaporated. The residue was partitioned between EtOAc and H$_2$O. The aqueous layer was acidified to pH 3 by addition of concentrated HCl and extracted with EtOAc. The organic layer was washed with brine, dried (Na$_2$SO$_4$), filtered and evaporated to afford 0.26 (73%) g of 84.

II-31 and II-32 were prepared as described in example 11 from 68b and 84 which afforded 3-{2-[5-(2,4-dimethyl-6-trifluoromethyl-pyridine-3-carbonyl)-hexahydro-pyrrolo[3,4-c]pyrrol-2-yl]-ethyl}-3-phenyl-azetidine-1-carboxylic acid tert-butyl ester which was deprotected and acylated using 4,4-difluoro-cyclohexane-carboxylic acid and 3,3-difluoro-cyclobutane-carboxylic acid respectively in the coupling step as described above.

EXAMPLE 25

(5-{2-[1-(3,3-Difluoro-cyclobutanecarbonyl)-3-phenyl-azetidin-3-yl]-1-methyl-ethyl}-hexahydro-pyrrolo[3,4-c]pyrrol-2-yl)-(4,6-dimethyl-pyrimidin-5-yl)-methanone (88c)

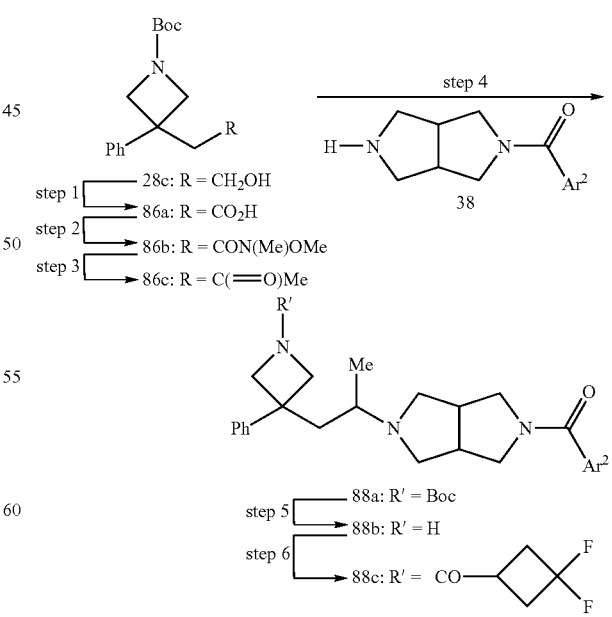

Ar$^2$ = 4,6-dimethyl-pyrimidin-5-yl step 1—The alcohol 28c (1.5 g, 5.408 mmol, Ar$^1$=Ph) was dissolved DCM (50 mL) and H$_2$O (20 mL) was added, followed by Na$_2$CO$_3$ (0.23 g, 2.738 mmol) and TEMPO (8.5 mg, 0.054 mmol). Sodium hypochlorite (10.1 ml, 6 wt %, equivalent to 0.604 g, 8.112 mmol) was added dropwise and the resulting mixture was vigorously stirred at RT overnight. The mixture was partitioned between DCM and 1M HCl. The aqueous layer was back extracted twice with DCM. Combined organic layers were dried (Na$_2$SO$_4$), filtered and evaporated to afford 86a which was used in the next step without purification.

step 2—N,O-Dimethylhydroxylamine hydrochloride (0.844 g, 8.65 mmol), HATU (3.29 g, 8.65 mmol) and DIPEA (5 mL, 28.8 mmol) were added to a solution of 86a (theoretically 5.408 mmol) in DCM (80 mL). The reaction was stirred overnight at RT, poured into 1N NaOH solution and stirred for 10 minutes. The organic layer was washed with H$_2$O, 2N HCl and brine, dried (Na$_2$SO$_4$), filtered and evaporated. The residue was purified by SiO$_2$ column chromatography eluting with hexanes:EtOAc (1:2) to give 1.43 (79%) of 86b.

step 3—MeLi (0.07 mL, 1.6 M in Et$_2$O, 0.1 mmol) is added to a solution of 86b (0.10 mmol) in THF (1 mL) maintained at −78° C. The reaction mixture is stirred at −78° C. until all starting material is consumed then quenched by the addition of aqueous NH$_4$Cl. The mixture is extracted with EtOAc, and the combined organic extracts are dried (Na$_2$SO$_4$) and concentrated. The crude product is purified by SiO$_2$ column chromatography eluting with hexanes/EtOAc to afford 86c.

step 4—Titanium tetraisopropoxide (2.5 mL, 8.44 mmol) was added at RT to a mixture of 38 (Ar$^2$=4,6-dimethyl-pyrimidin-5-yl), 1 g, 4.06 mmol) and 86c (1.1 g, 3.8 mmol) in DCM (20 mL) and THF (20 mL). After stirring at RT for 10 min, NaBH(OAc)$_3$ (1.07 g, 5.05 mmol) was added and the reaction mixture was stirred at RT for 4 h then partitioned between DCM and saturated NaHCO$_3$. The aqueous layer was back-extracted once with DCM. The combined organic layers were dried (Na$_2$SO$_4$), filtered and evaporated. The residue was purified by SiO$_2$ column chromatography eluting with a gradient of DCM/DCM-MeOH—NH$_4$OH [60/10/1] (100% to 50% DCM) to afford 1.71 (87%) of 88a.

steps 5 & 6—To a solution of 88a (31 mg, 0.06 mmol) in DCM (1 mL) at 0° C. was added TFA (0.5 mL). The resulting mixture was stirred at RT for 2 h before being evaporated and coevaporated with toluene to afford 88b. The residue was taken up into DCM (1 mL) and 3,3-difluorocyclobutanecarboxylic acid (0.01 g, 0.073 mmol), EDCI (0.013 g, 0.07 mmol) and HOBt (0.011 g, 0.07 mmol) were added followed by DIPEA (0.017 ml, 0.1 mmol). The resulting mixture was stirred at RT over the weekend then partitioned between DCM and H$_2$O. The aqueous layer was back extracted twice with DCM. The combined organic layers were dried (Na$_2$SO$_4$), filtered and evaporated. The residue was purified by HPLC (7-10 SB-Phenyl column, 1% TFA/acetonitrile 90/10 to 10/90 in 5 minutes, 1 ml/min) to give 17 mg (53%) of 88c.

(5-{2-[1-(4,4-Difluoro-cyclohexanecarbonyl)-3-phenyl-pyrrolidin-3-yl]-1-methyl-ethyl}-hexahydro-pyrrolo[3,4-c] pyrrol-2-yl)-(4,6-dimethyl-pyrimidin-5-yl)-methanone (90a) was prepared analogously except in the final step 4,4-difluoro-cyclohexane carboxylic acid is used in place of 3,3-difluoro-cyclobutane carboxylic acid.

EXAMPLE 26

4,6-Dimethyl-pyrimidin-5-yl)-(5-{2-[4-(3-fluorophenyl)-1-methanesulfonyl-piperidin-4-yl]-1-methyl-ethyl}-hexahydro-pyrrolo[3,4-c]pyrrol-2-yl)-methanone (92c)

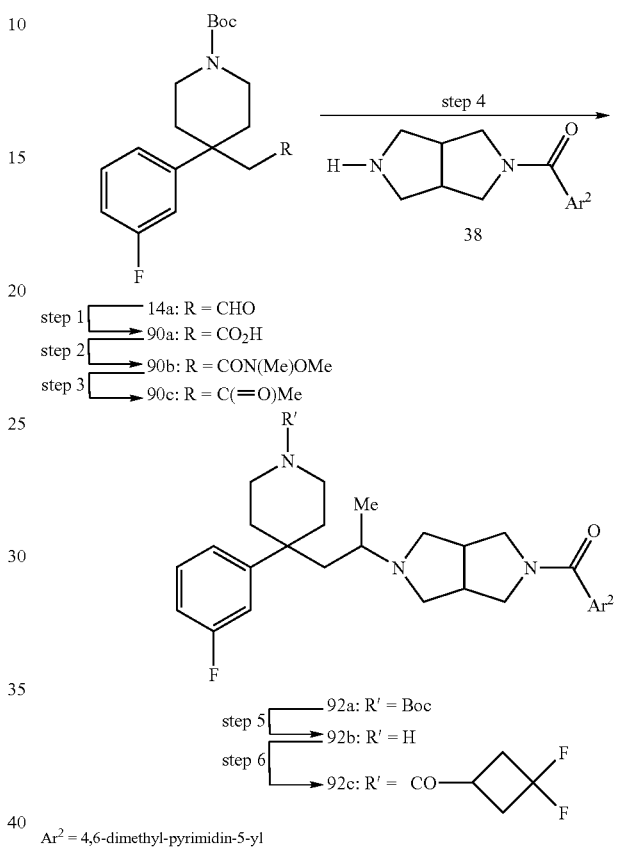

Ar$^2$ = 4,6-dimethyl-pyrimidin-5-yl step 1—Sodium hypochlorite (9.3 mL of 6 wt %, equivalent to 0.556 g, 7.468 mmol) is added drop-wise to a vigorously stirred mixture of 14a (0.6 g, 1.867 mmol), Na$_2$CO$_3$ (0.078 g, 0.933 mmol) and TEMPO (2.9 mg, 0.018 mmol) in DCM (25 mL) and H$_2$O (10 mL). The resulting mixture is vigorously stirred at RT overnight. The mixture then is partitioned between DCM and 1M HCl. The aqueous layer is back-extracted twice with DCM, the combined organic layers are dried (Na$_2$SO$_4$), filtered and evaporated. The residue 90a is used in the next step without purification.

step 2—N,O-Dimethylhydroxylamine hydrochloride (0.219 g, 2.24 mmol), HATU (0.852 g, 2.24 mmol) and DIPEA (1.3 mL, 7.468 mmol) is added to a solution of 90a (theoretically 1.867 mmol) in DCM (15 mL). The reaction is stirred overnight at RT, is poured into 1N NaOH solution and is stirred for 10 min. The organic layer is washed with H$_2$O, 2N HCl and brine, is dried (Na$_2$SO$_4$), is filtered and evaporated. The residue is purified by SiO$_2$ column chromatography eluting with hexanes:EtOAc to afford 90b.

step 3—A solution of MeMgBr (1.3 mL, 3M in THF) is added dropwise at −78° C. to a solution of 90b (0.5 g, 1.314 mmol) in THF (10 mL). The reaction mixture is warmed to RT over 4 h, is stirred at RT one additional h then is quenched by addition of 1M K$_2$HPO$_4$ and the resulting mixture is extracted with Et₂O. The organic layer is washed with saturated NaHCO₃ and brine, is dried (Na₂SO₄), filtered and then is evaporated. The residue is purified by SiO₂ column chromatography eluting with hexanes:EtOAc to afford 90c.

step 3—MeLi (0.07 mL, 1.6 M in Et₂O, 0.11 mmol) is added to a solution of 90b (0.10 mmol) in THF (1 mL) maintained at −78° C. The reaction mixture is stirred at −78° C. until all starting material is consumed then quenched by the addition of aqueous NH₄Cl. The mixture is extracted with EtOAc, and the combined organic extracts are dried (Na₂SO₄) and concentrated. The crude product is purified by SiO₂ column chromatography eluting with hexanes/EtOAc to afford 90c.

step 4—Titanium tetra-isopropoxide (0.763 mL, 2.578 mmol) is added at RT to a mixture of 38 (Ar²=4,6-dimethyl-pyrimidin-5-yl, 0.305 g, 1.237 mmol) and 90c (0.36 g, 1.289 mmol) in DCM (10 mL). The mixture is stirred at RT for 10 min, and NaBH(OAc)₃ (0.328 g, 1.547 mmol) is added and the reaction mixture is stirred at RT for 4 h then is partitioned between DCM and saturated NaHCO₃. The aqueous layer is back-extracted once with DCM. The combined organic extracts are dried (Na₂SO₄), filtered and evaporated. The residue is purified by SiO₂ column chromatography eluting with a gradient of DCM/DCM-MeOH—NH₄OH [60/10/1] (100% to 50% DCM) to afford 92a.

steps 5& 6—TFA (0.5 mL) is added at 0° C. to a solution of 92a (40 mg, 0.071 mmol) in DCM (1 mL) and the resulting mixture is stirred at RT for 1 h, then evaporated and co-evaporated with toluene which affords 92b. The resulting amine 92b is dissolved in DCM (0.75 mL), is cool to 0° C. and TEA (20 μL, 0.142 mmol) and methanesulfonyl chloride (8 μL, 0.01 mmol) are sequentially added. The reaction mixture is stirred at 0° C. for 1 h then is partitioned between DCM and saturated NaHCO₃. The aqueous layer is back-extracted once with DCM. The combined organic extracts are dried (Na₂SO₄), filtered and evaporated. The residue is purified by SiO₂ column chromatography which is eluted with a gradient of DCM/DCM-MeOH—NH₄OH [60/10/1] (100% to 50% DCM) to afford 92c.

EXAMPLE 27

4-[3-[5-(4,6-Dimethyl-pyrimidine-5-carbonyl)-hexahydro-pyrrolo[3,4-c]pyrrol-2-yl]-1-(3-fluoro-phenyl)-butyl]-piperidine-1-carboxylic acid tert-butyl ester (96c)

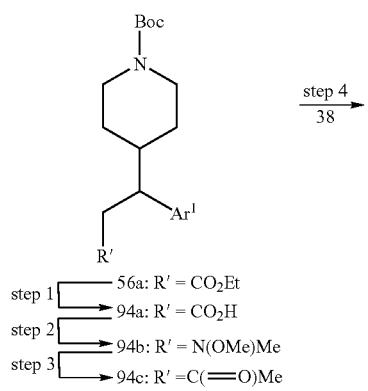

step 1 [ 56a: R' = CO₂Et
         94a: R' = CO₂H
step 2 [ 94b: R' = N(OMe)Me
step 3 [ 94c: R' =C(═O)Me -continued

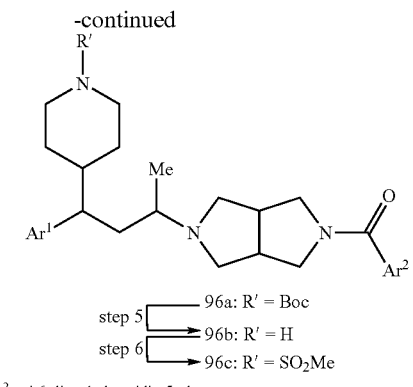

step 5 [ 96a: R' = Boc
         96b: R' = H
step 6 [ 96c: R' = SO₂Me

Ar¹ = 3-fluoro-phenyl; Ar² = 4,6-dimethyl-pyridin-5-yl step 1—NaOH (2 mL, 1N aqueous solution, 2 mmol) is added to a solution of 56a (200 mg, 0.52 mmol) in EtOH (5 mL). The resulting mixture is heated at 50° C. for 24 h. The reaction mixture is cooled to RT and the pH is adjusted to 2 with 1N HCl and then the solution is extracted with DCM. The combined organic extracts were dried (Na₂SO₄) and concentrated to afford 94a.

step 2—CDI (120 mg, 0.74 mmol) is added to a solution of 94a (180 mg, 0.51 mmol) in DCM (5 mL). The solution is stirred at RT for 1 h and N,O-dimethylhydroxylamine HCl (74 mg, 0.76 mmol) is added. The reaction mixture is stirred at RT over the weekend, then is quenched by the addition of H₂O and the mixture is extracted with DCM. The combined organic extracts are dried (Na₂SO₄), concentrated and purified by SiO₂ column chromatography eluting with hexanes/EtOAc to afford 94b.

step 3—A solution of MeMgCl (0.35 mL, 3M in THF) is added dropwise to a solution of 94b (130 mg, 0.33 mmol) in THF (3 mL) cooled −78° C. The reaction mixture is warmed to RT over 5 h, is stirred at RT one additional hour then is quenched by addition of 1M K₂HPO₄ and is extracted with Et₂O. The organic layer is washed with saturated NaHCO₃ and brine, is dried (Na₂SO₄), filtered and evaporated. The residue was purified by SiO₂ column chromatography eluting with hexanes/EtOAc to afford 94c.

step 3—MeLi (0.07 mL, 1.6 M in Et₂O, 0.11 mmol) was added to a solution of 86b (40 mg, 0.10 mmol) in THF (mL) maintained at −78° C. The reaction mixture was stirred at −78° C. until all starting material was consumed then quenched by the addition of aqueous NH₄Cl. The mixture was extracted with EtOAc, and the combined organic extracts were dried (Na₂SO₄) and concentrated. The crude product was purified by SiO₂ column chromatography eluting with hexanes/EtOAc to afford 94c.

step 4—Titanium tetraisopropoxide (0.23 mL, 0.78 mmol) is added at RT to a mixture of 38 (Ar²=4,6-dimethyl-pyrimidin-5-yl, 90 mg, 0.37 mmol) and 94c (115 mg, 0.33 mmol) in DCM (2 mL) and THF (2 mL). After stirring at RT for 10 minutes, NaBH(OAc)₃ (70 mg, 0.33 mmol) is added and the reaction mixture is stirred at RT for 4 h then is partitioned between DCM and saturated NaHCO₃. The aqueous layer is back-extracted once with DCM. The combined organic layers are dried (Na₂SO₄), filtered and evaporated. The residue is and the diastereomers are separated by SiO₂ column chromatography eluting with a gradient of DCM/DCM-MeOH—NH₄OH [60/10/1] (100% to 50% DCM) to afford 96a.

step 5 & 6—TFA (0.5 mL) is added at 0° C. to a solution of 96a (34 mg, 0.06 mmol) in DCM (1 mL). The resulting mixture is stirred at RT for 2 h then is evaporated and co-evaporated with toluene to afford 96b. The residue containing 96b is dissolved DCM (1 mL), is cooled to 0° C. and TEA (13 μL, 0.093 mmol) and methanesulfonyl chloride (7 μL, 0.09 mmol) are added sequentially. The reaction mixture was stirred at 0° C. for 1 hour before being partitioned between DCM and saturated NaHCO₃. The aqueous layer is back-extracted with DCM. The combined organic extracts is dried (Na₂SO₄), is filtered and evaporated. The residue is purified by SiO₂ column chromatography eluting with a gradient of DCM/DCM-MeOH—NH₄OH [60/10/1] (100% to 50% DCM) to afford 96c.

EXAMPLE 28

(5-{2-[1-(3,3-Difluoro-cyclobutanecarbonyl)-3-phenyl-pyrrolidin-3-yl]-ethyl}-hexahydro-pyrrolo[3,4-c]pyrrol-2-yl)-(3,5-dimethyl-1-pyrimidin-5-yl-1H-pyrazol-4-yl)-methanone (104b)

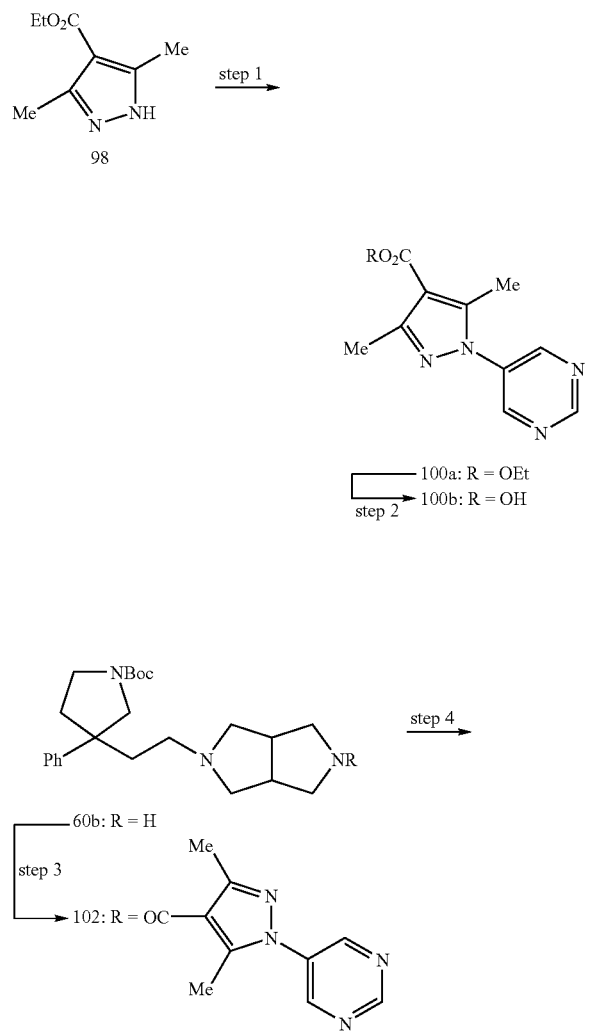

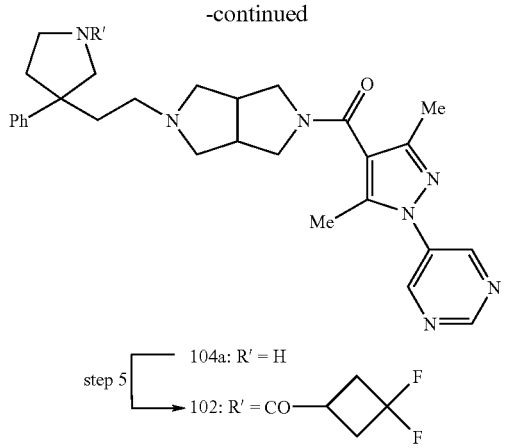

step 1—N,N'-Dimethylethylenediamine (90 μL, 0.832 mmol) was added to a mixture of 3,5-dimethyl-1H-pyrazole-4-carboxylic acid ethyl ester (98, 1.4 g, 8.324 mmol), 5-bromopyrimidine (1.32 g, 8.303 mmol), CuI (0.16 g, 0.84 mmol) and K₂CO₃ (2.3 g, 16.64 mmol) in 1,4-dioxane (8 mL) that was maintained under an Ar atmosphere. The resulting mixture was stirred at 110° C. under Ar for 16 h. The reaction mixture was cooled to RT, diluted with DCM (50 mL) and filtered through a CELITE® and SiO₂ pad. The filter cake was rinsed with EtOAc and the filtrate was evaporated in vacuo. The residue was purified via SiO₂ chromatography eluting with hexane/EtOAc to afford the 0.150 g (7%) of 100a.

step 2—A solution of KOH (77 mg, 1.38 mmol) in water (0.5 mL, plus 0.25 mL to rinse) was added to a solution of 100a (170 mg, 0.69 mmol) in EtOH (3 mL). The resulting mixture was stirred at 40° C. for 24 h, cooled to RT and evaporated in vacuo. The residue was partitioned between EtOAc and water and the resulting aqueous layer was separated and extracted with EtOAc. The aqueous layer was acidified to pH 4 with 3M HCl. The precipitate was filtered and rinsed with water to afford 0.086 g (57%) of 100b which was used for the next step without additional purification.

step 3—DIPEA (0.16 mL, 0.934 mmol) is added to a mixture of 60b (0.24 g, 0.623 mmol), 100b (0.611 mmol) and TBTU (0.26 g, 0.805 mmol) in DCM (5 mL) and DMF (0.5 mL). The resulting mixture is stirred at RT overnight then partitioned between DCM and H₂O. The aqueous layer is back-extracted twice with DCM. The combined organic layers are dried (Na₂SO₄), filtered and evaporated. The residue is purified by SiO₂ chromatography eluting with a gradient of DCM/DCM-MeOH—NH₄OH (60/10/1) (100 to 50% DCM) to afford 102.

step 4—To a solution of 102 (0.289 mmol) in DCM (2 mL) at RT is added a 4M HCl solution in dioxane (2 mL). The reaction mixture is stirred for 2 h then is evaporated to afford 104a.

step 5—DIPEA (0.15 mL, 0.866 mmol) is added to a mixture of 104a (96.26 μmol), 3,3-difluorocyclobutane-carboxylic acid (0.020 g, 0.144 mmol), EDCI (0.022 g, 0.116 mmol) and HOBt (0.018 g, 0.116 mmol) in DCM (0.4 mL). The resulting mixture is stirred at RT overnight then is partitioned between DCM and H₂O. The aqueous layer is back-extracted twice with DCM. The combined organic layers are dried over (Na₂SO₄), filtered and evaporated. The residue is purified by SiO₂ chromatography eluting with a gradient of DCM/DCM-MeOH—NH₄OH (60/10/1) (100 to 50% DCM) to afford 102b.

EXAMPLE 29

(5-{2-[1-(3,3-Difluoro-cyclobutanecarbonyl)-3-phenyl-pyrrolidin-3-yl]-ethyl}-hexahydro-pyrrolo[3,4-c]pyrrol-2-yl)-(3,5-dimethyl-1-pyridazin-3-yl-1H-pyrazol-4-yl)-methanone (110b)

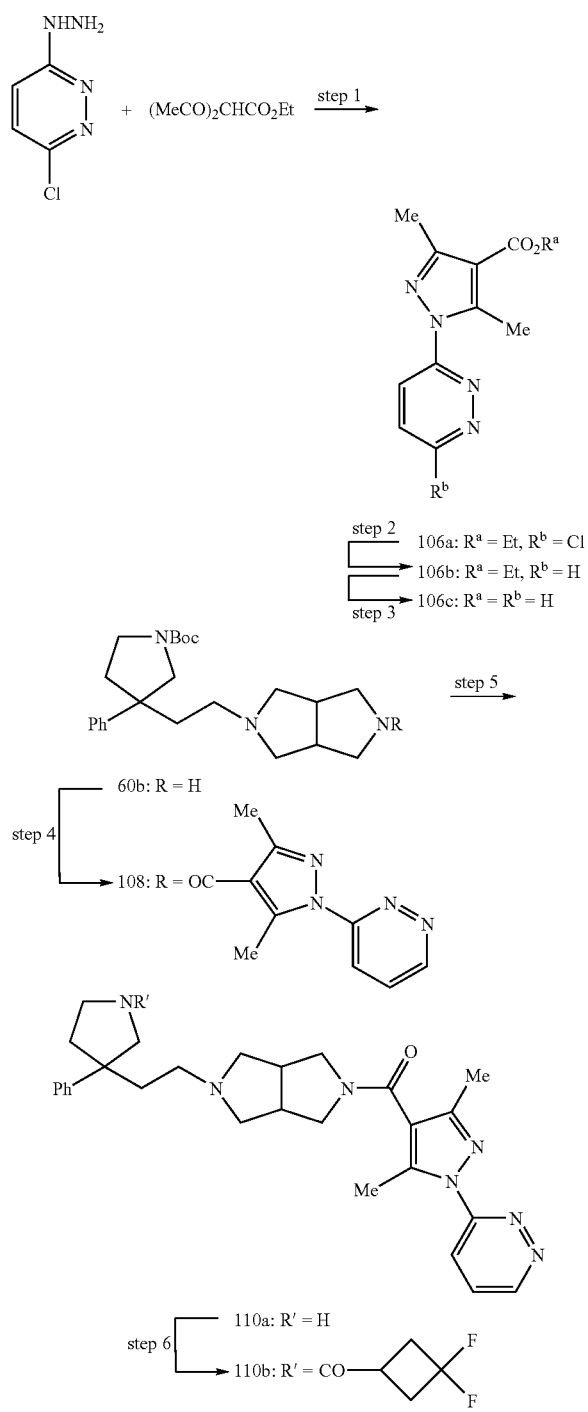

step 1—Ethyl diacetoacetate (2 mL, 12.8 mmol) was added at RT to a mixture of 3-chloro-6-hydrazinopyridazine (1.5 g, 10.4 mmol) and HOAc (1 mL) in MeOH (30 mL). The resulting mixture was stirred at RT for 1 h. The resulting precipitate was filtered and rinsed with EtOH. The process was repeated twice as more product precipitated form the filtrate. The combined solids afforded 1.75 g (60%) of 106a.

step 2—A suspension of 106a (1.75 g, 6.25 mmol) and Pd/C (10%, 250 mg) in 5:1 MeOH/1,4-dioxane (120 mL) was stirred under a $H_2$ atmosphere (balloon pressure) at RT for 72 h. The catalyst was filtered, and the filter cake was rinsed with MeOH. The filtrate was evaporated and the residue was purified via $SiO_2$ chromatography eluting with hexane/EtOAc to afford 0.340 g (22%) of 106b.

step 3—To a solution of 106b (0.34 g, 1.38 mmol) and 4 mL of $H_2O$ was added a solution of KOH (0.155 g, 2.76 mmol) and 0.5 mL of $H_2O$. The mixture was stirred at 40° C. for 24 h then evaporated. The residue was partitioned between water and EtOAc. The aqueous layer was separated and adjusted to pH 2 with con HCl. The resulting precipitate was washed with $H_2O$ and acetone and dried to afford 0.235 g (78%) of 106c.

The condensation of 106c and 60b is carried out with TBTU and DIPEA as described in step 3 of example 28. Deprotection and condensation with 3,3-difluoro-cuclobutanecarboxylic acid is carried out with HCl/dioxane and EDCI/HOBt as described in steps 4 and 5 of example 28 to afford 110b. The final product is purified by $SiO_2$ chromatography eluting with a gradient of DCM/DCM-MeOH—$NH_4OH$ (60/10/1) (100 to 50% DCM).

EXAMPLE 30

(1-Cyclohexyl-3,5-dimethyl-1H-pyrazol-4-yl)-(5-{2-[1-(3,3-difluoro-cyclobutanecarbonyl)-3-phenyl-pyrrolidin-3-yl]-ethyl}-hexahydro-pyrrolo[3,4-c]pyrrol-2-yl)-methanone (116b)

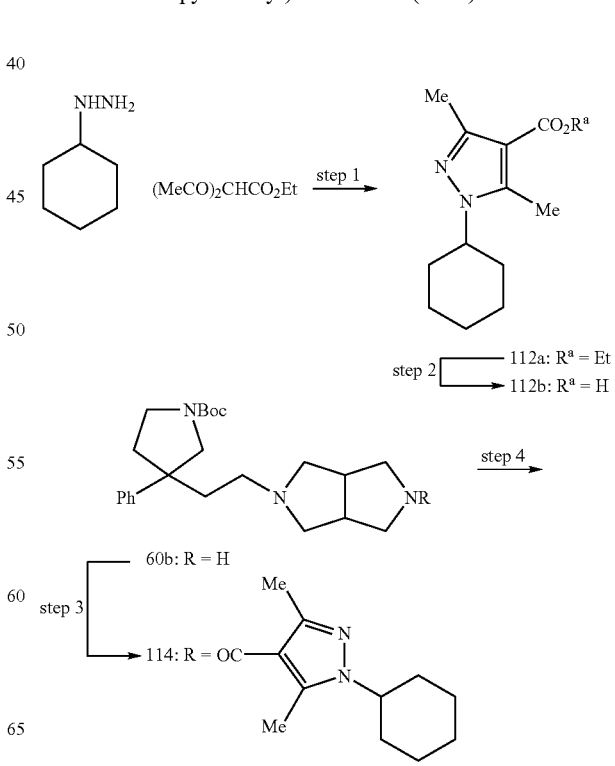

-continued

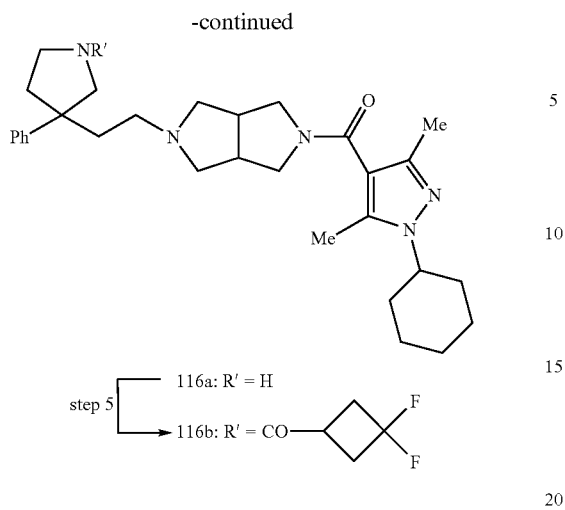

step 5 ⎡ 116a: R' = H
       ⎣ 116b: R' = CO—[3,3-difluorocyclobutyl]

step 1—Ethyl diacetoacetate (2.3 mL, 14.7 mmol) was added at RT to a solution of cyclohexylhydrazine hydrochloride (2.0 g, 13.3 mmol) in a 8:5 mixture of MeOH/water (65 mL). The resulting mixture was vigorously stirred at RT for 18 h and then evaporated. The residue was purified via $SiO_2$ chromatography (hexane/EtOAc) to afford 1.6 g (48%) of 112a.

step 2—To a solution of 112a (1.6 g, 6.391 mmol) and EtOH (12 mL) was added a solution of KOH (1.076 g, 19.17 mmol) and $H_2O$ (3 mL). The resulting solution was stirred at RT for 72 h then heated at 50° C. for an additional 24 h. The resulting solution was cooled to RT and evaporated. The residue was partitioned between $H_2O$ and EtOAc. The aqueous layer was adjusted to pH 2 with con HCl and the resulting precipitate filtered, rinsed with $H_2O$ and dried to afford 1.34 g (94.3%) of 112b.

The condensation of 112b and 60b is carried out with TBTU and DIPEA as described in step 3 of example 28. Deprotection and condensation of 116a with 3,3-difluoro-cyclobutane-carboxylic acid is carried our with HCl/dioxane and EDCI/HOBt as described in steps 4 and 5 of example 28 to afford 116b. The final product is purified by $SiO_2$ chromatography eluting with a gradient of DCM/DCM-MeOH—$NH_4OH$ (60/10/1) (100 to 50% DCM).

EXAMPLE 31

(5-{2-[1-(3,3-Difluoro-cyclobutanecarbonyl)-3-phenyl-pyrrolidin-3-yl]-ethyl}-hexahydro-pyrrolo[3,4-c]pyrrol-2-yl)-[3,5-dimethyl-1-(6-trifluoromethyl-pyridazin-3-yl)-1H-pyrazol-4-yl]-methanone (122b)

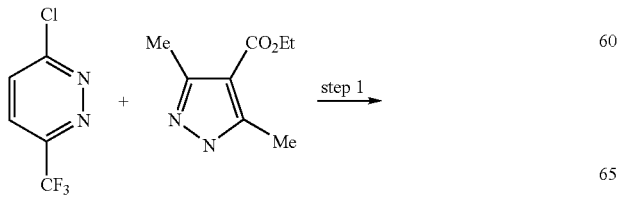

-continued

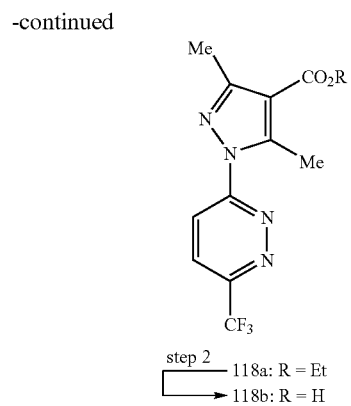

step 2 ⎡ 118a: R = Et
       ⎣ 118b: R = H

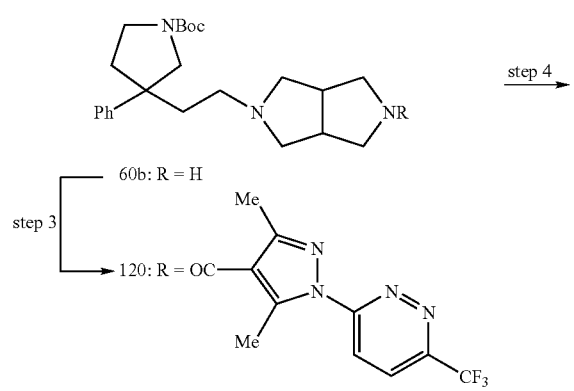

step 3 ⎡ 60b: R = H
       ⎣ 120: R = OC—[pyrazolyl-pyridazine]

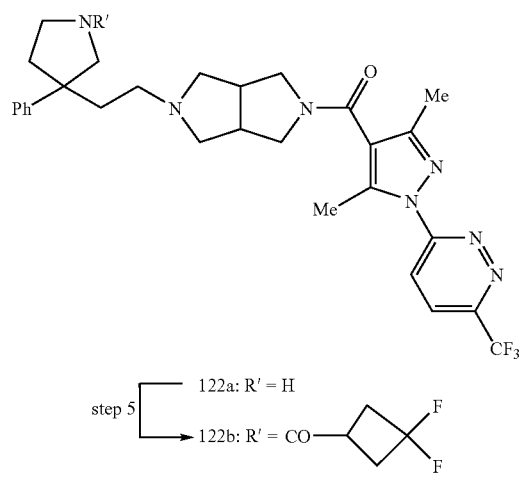

step 5 ⎡ 122a: R' = H
       ⎣ 122b: R' = CO—[3,3-difluorocyclobutyl]

step 1—To a solution of 3,5-dimethyl-1H-pyrazole-4-carboxylic acid ethyl ester (0.2 g, 1.19 mmol) in DMF (10 mL) cooled to 0° C. was added sequentially NaH (60% in mineral oil, 72 mg, 1.78 mmol) and 3-chloro-6-trifluoromethyl-pyridazine (0.22 g, 1.21 mmol; Tetrahedron 1999 55:15067-15070). The resulting mixture was stirred at RT for 3 h then partitioned between EtOAc and saturated aqueous NH₄Cl. The layers were separated and the aqueous layer was extracted twice with EtOAc. The combined extracts were dried (Na₂SO₄), filtered and evaporated. The residue was purified via SiO₂ chromatography eluting with hexane/EtOAc to afford 0.228 g (62%) of 118a.

step 2—To a solution of 118a and EtOH (12 mL) is added a solution of KOH (3 equivalents) and H₂O (3 mL). The resulting solution is stirred at RT for 72 h. then is heated at 50° C. for an additional 24 h. The resulting solution is cooled to RT and evaporated. The residue is partitioned between H₂O and EtOAc. The aqueous layer is adjusted to pH 2 with con HCl and the resulting precipitate filtered, rinsed with H₂O and dried to afford 118b.

The condensation of 118b and 60b is carried out with TBTU and DIPEA as described in step 3 of example 28. Deprotection and condensation of 122a with 3,3-difluoro-cyclobutanecarboxylic acid is carried our with HCl/dioxane and EDCI/HOBt as described in steps 4 and 5 of example 28 to afford 122b. The final product is purified by SiO₂ chromatography eluting with a gradient of DCM/DCM-MeOH—NH₄OH (60/10/1) (100 to 50% DCM).

EXAMPLE 32

(5-{2-[1-(3,3-Difluoro-cyclobutanecarbonyl)-3-phenyl-pyrrolidin-3-yl]-ethyl}-hexahydro-pyrrolo[3,4-c]pyrrol-2-yl)-(3,5-dimethyl-1-pyrazin-2-yl-1H-pyrazol-4-yl)-methanone (128b)

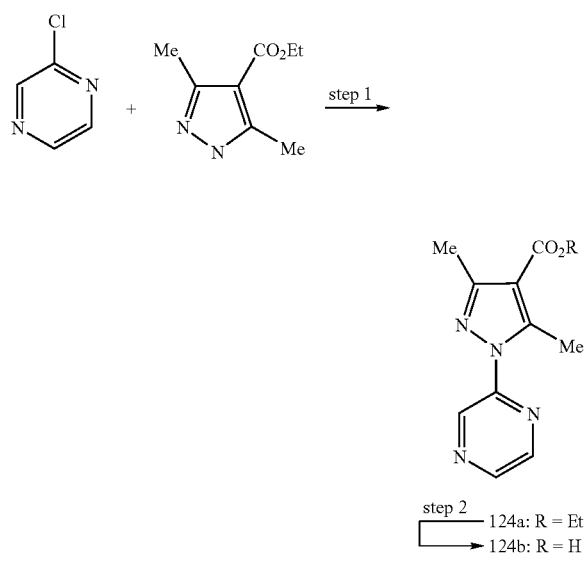

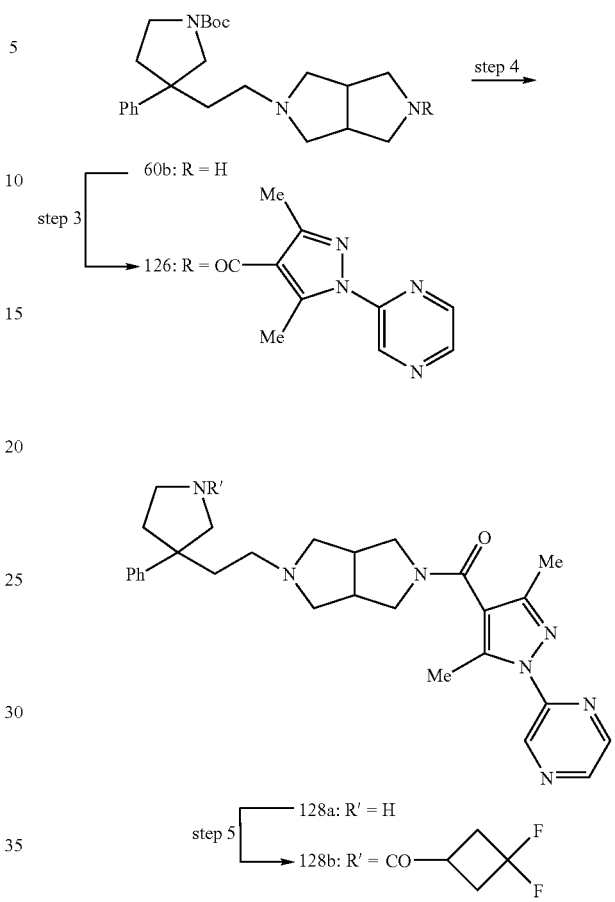

step 1—To a solution of 3,5-dimethyl-1H-pyrazole-4-carboxylic acid ethyl ester (1 g, 5.95 mmol) in DMF (20 mL) cooled to 0° C. was added portionwise NaH (60% in mineral oil, 171 mg, 7.13 mmol). After hydrogen evolution ceased, 2-chloro-pyrazine (0.64 mL, 7.13 mmol) was added and the reaction was stirred at 50° C. for 24 h. The reaction mixture was cooled to RT, partitioned between EtOAc and saturated NH₄Cl. The aqueous layer was extracted twice with EtOAc. The combined organic layers were dried (Na₂SO₄), filtered and evaporated. The residue was purified via SiO₂ chromatography eluting with hexane/EtOAc to afford 0.64 g (44%) of 3,5-dimethyl-1-pyrazin-2-yl-1H-pyrazole-4-carboxylic acid ethyl ester (124a). The ethyl ester was hydrolyzed to the corresponding acid with KOH in aqueous EtOH as described in step 2 of example 31.

The condensation of 124b and 60b is carried out with TBTU and DIPEA as described in step 3 of example 28. Deprotection and condensation of 128a with 3,3-difluoro-cyclobutanecarboxylic acid is carried our with HCl/dioxane and EDCI/HOBt as described in steps 4 and 5 of example 28 to afford 128b. The final product is purified by SiO₂ chromatography eluting with a gradient of DCM/DCM-MeOH—NH₄OH (60/10/1) (100 to 50% DCM).

EXAMPLE 33

N-(5-{5-[3-[1-(2,2-Difluoro-ethyl)-piperidin-4-yl]-3-(3,5-difluoro-phenyl)-propyl]-hexahydro-pyrrolo[3,4-c]pyrrole-2-carbonyl}-4,6-dimethyl-pyridin-2-yl)-methanesulfonamide (140c)

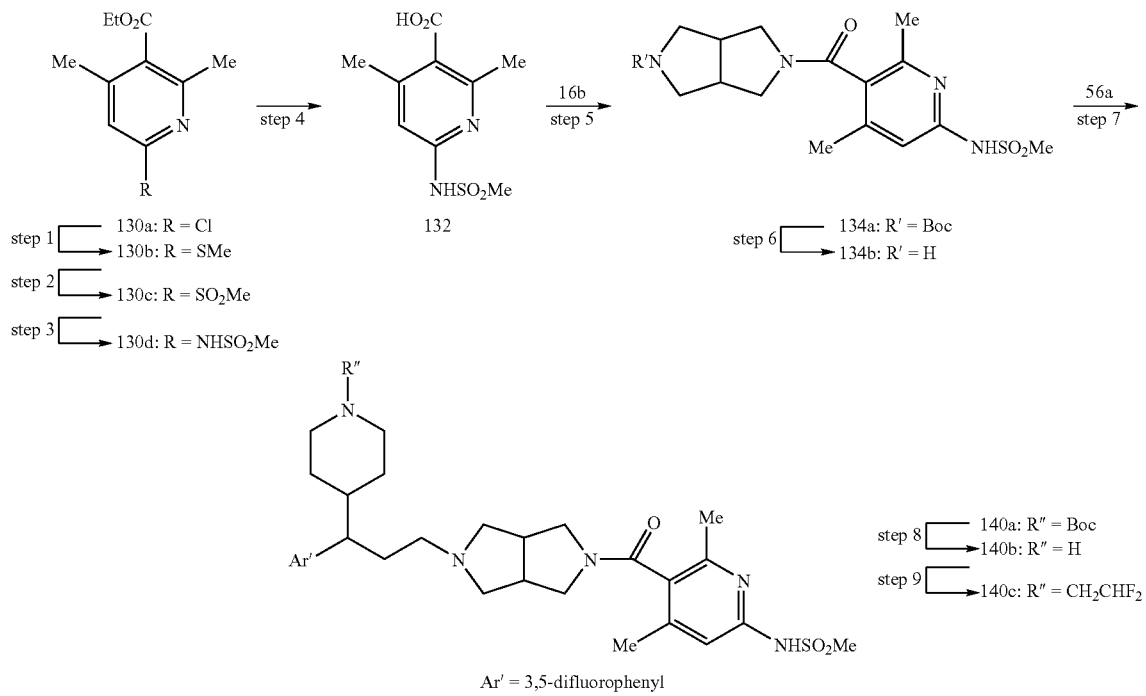

step 1—To a solution of 130a (163 mg, 0.77 mmol, CASRN 54453-94-0) in dioxane or DMF was added NaSMe (excess) and the reaction mixture was stirred at 50-70° C. until all starting material was consumed. The reaction mixture was allowed to cool to RT then diluted with aq. NaHCO$_3$ was added, and the resulting mixture was extracted with EtOAc, dried (Na$_2$SO$_4$) and concentrated. The crude product was purified by ISCO eluting with an EtOAc/hexane gradient (5-15% EtOAc over 60 min).

step 2: Oxone (680 mg, 1.1 mmol) in water (4 mL) was added to a solution of 130b (113 mg, 0.5 mmol) in MeOH (4 mL) maintained at 0° C. The reaction mixture was stirred overnight and warmed to RT. Water was added and the mixture was extracted with DCM The combined organic extracts were dried (Na$_2$SO$_4$) and concentrated. The resulting sulfone 130c was used in the next step without further purification.

step 3—To a solution of methanesulfonamide (33 mg, 0.35 mmol) in THF (1 mL) and DMF (0.5 mL) was added NaH (11 mg, 60% dispersion). The mixture was heated to 80° C. and a solution of 130c (55 mg, 0.21 mmol) and DMF (2 mL) was added. The reaction mixture was stirred at 80° C. until starting material was consumed (more NaH and methanesulfonamide were added, if needed). The reaction mixture was cooled to 0° C., water was added, and the aqueous layer was washed with EtOAc. The aqueous layer was adjusted to pH ca. 1) with 1N HCl, and extracted with DCM. The combined extracts were dried (Na$_2$SO$_4$), concentrated and purified by SiO$_2$ chromatography.

step 4—To a solution of 130d (10 mg, 0.037 mmol) and EtOH (1 mL) was added aqueous 2M NaOH and the solution was heated to 50° C. After the reaction was complete, the mixture was cooled to RT, acidified to a pH of about 2 with 1N HCl and extracted with EtOAc. The combined organic extracts were dried (Na$_2$SO$_4$), filtered and concentrated to afford 9.1 mg of 132.

The intermediate 140b was prepared from 132b and 16b as described in steps E2-E7 of example 13 except in step 2,3,5-difluorophenyl magnesium bromide was used in place of 3-fluorophenyl magnesium bromide. Conversion of 140b to the title compound was carried out as described in example 15 except 2,2-difluoroethyl triflate was used in place of 2,2,2-trifluoroethyl triflate.

EXAMPLE 34

Human CCR5 Receptor-ligand Binding (RANTES) Assay Protocol

Human CCR5 receptor (Genebank ID: 29169292) was cloned into mammalian expression vector, pTarget (Promega). The construct was transfected into CHO-G$_{\alpha 16}$ cells by using Fugene Reagent (Roche). Clones were selected under antibiotic pressure (G418 and Hygromycin) and sorted 4 times with a fluorescence activates cell sorter and a monoclonal antibody specific for CCR5 receptor (BD Biosciences Pharmigen, Mab 2D7, Cat. No. 555993). The clone with highest expression (100,000 copies per cell) was chosen for the binding assays.

Adherent cells in 225 mL tissue culture flask (~90% confluent) were harvested using 1 mM EDTA in PBS (phosphate-buffered saline) without $Ca^{2+}$ and $Mg^{2+}$. Cells were washed twice with PBS containing no $Ca^{2+}$ and $Mg^{2+}$. CHO-$G_{\alpha 16}$-hCCR5 cells were then resuspended ($1\times10^6$/ml) in ice cold binding buffer (50 mM HEPES, 1 mM $CaCl_2$, 5 mM $MgCl_2$, 0.5% BSA, 0.05% $NaN_3$, pH 7.24), pH 7.4), supplemented with freshly made 0.5% BSA and 0.05% $NaN_3$.

Eighty μl CHO-$G_{\alpha 16}$-hCCR5 ($1\times10^6$/ml) cells were added to 96 well plates. All dilutions were made in binding buffer (50 mM HEPES, 1 mM $CaCl_2$, 5 mM $MgCl_2$, 0.5% BSA, 0.05% $NaN_3$, pH 7.24).

The plates were incubated on a cell shaker at RT for 2 h with a final concentration of 0.1 nM $^{125}$I RANTES or $^{125}$I MIP-1α or $^{125}$I MIP-1β. The compound dilutions were made in PBS, 1% BSA. Total reaction volume was 100 μl per well. The test compounds were added to the cells prior to the addition of radioligand.

After incubation, the cells were harvested onto GF/C filter plates using Packard cell harvester. Filters were pretreated with 0.3% PEI/0.2% BSA for 30 min. The filter plate was washed rapidly 5 times with 25 mM HEPES, 500 mM NaCl, 1 mM $CaCl_2$ and 5 mM $MgCl_2$ adjusted to pH 7.1. Plates were dried in oven (70° C.) for 20 min, added with 40 μl scintillation fluid and sealed with Packard TopSeal-A. Packard Top Count was used to measure the radioactivity for 1 min per well.

Total binding was determined with control wells added with radioisotope and buffer and the non-specific binding was determined using an excess cold RANTES to some of the control wells. Specific binding was determined by subtracting the non-specific form total binding. Results are expressed as the percentage of specific $^{125}$I RANTES binding. $IC_{50}$ values were determined using varying concentrations of the test ligand in triplicates and the data was analyzed using GraphPad Prism (GraphPad, San Diego, Calif.). Exemplary results are tabulated in TABLE VI infra.

EXAMPLE 35

CCR5-Mediated CCF Assay

CCF assay was performed as described before (C. Ji, J. Zhang, N. Cammack and S. Sankuratri 2006 *J. Biomol. Screen* 2006 11(6):652-663). Hela-R5 cells (express gp160 from R5-tropic virus and HIV-1 Tat) were plated in 384 well white culture plates (BD Bioscience, Palo Alto, Calif.) at $7.5\times10^3$ cells per well in phenol red-free Dulbecco's Modified Eagle Medium (DMEM) supplemented with 10% FBS, 1× Pen-Strep, 300 μg/ml G418, 100 μg/ml hygromycin, and 1 μg/ml Doxycycline (Dox) (BD Bioscience, Palo Alto, Calif.), using Multimek (Beckman, Fullerton, Calif.) and incubated at 37° C. overnight to induce the expression of gp160. Ten μl diluted compounds in medium containing 5% DMSO were added to the cells, followed by the addition of CEM-NKr-CCR5-Luc (obtained from NIH AIDS Research & Reference Reagents Program) that expresses CD4 and CCR5 and carries a HIV-2 long terminal repeat (LTR)-driven luciferase reporter gene at $1.5\times10^4$ cells/15 μL/well and incubated for 24 hrs. At the end of co-culture, 15 μl of Steady-Glo luciferase substrate was added into each well, and the cultures were sealed and gently shaken for 45 min. The luciferase activity were measured for 10 sec per well as luminescence by using 16-channel TopCount NXT (PerkinElmer, Shelton, Conn.) with 10 min dark adaptation and the readout is count per second (CPS). For the drug interaction experiments, small molecule compounds or antibodies were serially diluted in serum-free and phenol red-free RPMI containing 5% dimethyl sulfoxide (DMSO) (CalBiochem, La Jolla, Calif.) and 1× Pen-Strep. Five μl each of the two diluted compound or mAb to be tested for drug-drug interactions were added to the Hela-R5 cells right before the addition of target cells. The checker board drug combinations at various concentrations were carried out as shown in FIG. 1A.

TABLE VI

| Cpd No. | RANTES Binding Assay $IC_{50}$ (μM) | Cell Fusion Assay $IC_{50}$ (μM) |
| --- | --- | --- |
| I-1 | 0.8349 | 0.8349 |
| I-3 | 0.0776 | 0.306 |
| I-9 | 0.5 | 2.5 |
| I-14 | 0.0484 | 1.202 |
| I-19 | 0.0509 | 0.3928 |
| I-25 | 0.1016 | 0.1595 |
| II-6 | 0.0277 | 0.1359 |
| II-15 | 0.0515 | 0.4857 |
| II-19 | 0.1051 | — |
| II-22 | 0.0271 | 0.4575 |
| II-33 | 0.0113 | 0.0026 |
| II-39 | 0.0188 | 0.0095 |
| III-8 | 0.0688 | 0.3596 |
| IV-10 | 0.244 | 0.4575 |
| IV-14 | 0.0386 | 0.0042 |
| V-7 | 0.1022 | 0.7441 |
| V-15 | 0.0082 | 0.202 |
| V-24 | 0.0313 | 0.0013 |

EXAMPLE 36

Chemotaxis Assay

L1.2hCCR5 cells are cultured in RPMI 1640 containing 10% fetal bovine serum, 10 μg/mL penicillin/streptomycin, 0.1 mM glutamine, 1M sodium pyruvate, 55 μM β-mercaptoethanol, and 250 μg/mL geneticin (all from Invitrogen). Just prior to the set up of the chemotaxis assay, the cells are spun down and resuspended in Chemotaxis Buffer (Hank's Balanced Salt Solution HBSS (Invitrogen) containing 0.1% BSA and 10 mM HEPES). The cells are used in the chemotaxis assay at a final concentration of $5\times10^6$ cells/mL.

CCR5 ligands hMIP1α, hMIP1β or hRANTES (R&D Systems) are diluted in Chemotaxis Buffer and are used at a final concentration of 10 nM. Test substances and the appropriate vehicle control are diluted in Chemotaxis Buffer.

The chemotaxis assay is set up in the 0.5 μm pore 96-well ChemoTx$^R$ system (Neuroprobe). Each test or control substance is mixed with one of the CCR5 ligands and 30 μL of this mixture is placed in the bottom well of the ChemoTx$^R$ system. The filter screen in placed on top of the bottom wells and forms the top wells. Each test or control substance is mixed with the L1.2hCCR5 cells and 20 μL of this mixture is placed on the top wells. The plates are then placed in a humidified chamber and incubated at 37° C. and 5% $CO_2$ for 3 h.

After the incubation period, the cells are scraped off the filter and the plates are spun in a table top centrifuge at 2,000 rpm for 10 min. The filter is then removed and the density of the cells that have migrated to the bottom wells is detected using CyQUANT$^R$ cell proliferation assay kit (Invitrogen) and the Spectra MAX GeminiXS plate reader (Molecular Devices) according to the manufacturers' instructions. Using the fluorescence measurements the percent migration is determined by % migration=$[1-(max-obs)/(max-min)] \times 100$. The observed value (obs) is the value observed in the test well. The maximum (max) is the average of ligand+control and the minimum (min) is the average of the no ligand+control. The IC$_{50}$ is defined at the midpoint between the minimum and maximum of the dose response curve. This is calculated with Excel Fit.

TABLE VII

| Cpd. No. | Chemotaxis Inhibition[1] IC$_{50}$ (µM) |
|---|---|
| V-12 | 0.765 |

[1]Inhibition of RANTES stimulated chemotaxis

EXAMPLE 37

Pharmaceutical compositions containing the subject compounds for administration via several routes are prepared as described in this Example.

Composition for Oral Administration (A)

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
|---|---|
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula I

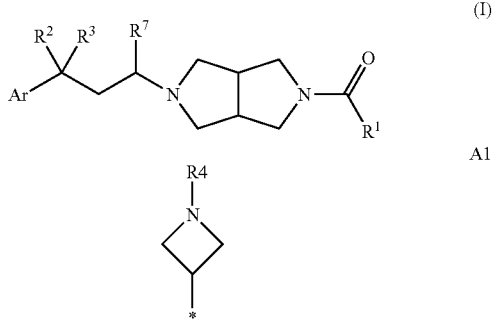

-continued

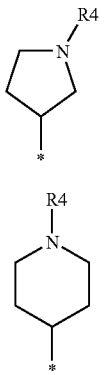

wherein
R¹ is selected from the group consisting of (a) phenyl, (b) pyridinyl, (c) pyrimidinyl, each optionally substituted with $C_{1-6}$ alkyl, $C_{1-6}$ haloalkyl, $C_{1-6}$ alkoxy, hydroxy, cyano, $NHSO_2C_{1-6}$ alkyl, $SO_2NR^{9a}R^{10a}$, $-NR^{9b}R^{10b}$, and halogen, and (d) B1

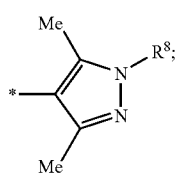

wherein $R^8$ is $C_{3-7}$ cycloalkyl, phenyl or heteroaryl selected from the group consisting of pyridine, pyrimidine, pyrazine and pyridazine said heteroaryl or said phenyl optionally substituted with $C_{1-3}$ alkyl or $C_{1-3}$ haloalkyl;

One of $R^2$ and $R^3$ is hydrogen and the other of $R^2$ and $R^3$ is A1, A2 or A3, or $R^2$ and $R^3$ together are $(CH_2)_mNR^4(CH_2)_n$ wherein m and n are independently one or two;

$R^4$ is $C_{1-6}$ alkyl, $C_{1-6}$ haloalkyl, $CH_2C≡N$, $-C(=O)R^5$ or $-SO_2R^5$;

$R^5$ is (a) $C_{1-6}$ alkyl, (b) $C_{3-6}$ cycloalkyl optionally independently substituted with one or two $C_{1-6}$ alkyl, halogen, hydroxy, cyano, oxo or $C_{1-6}$ haloalkyl, (c) $C_{1-6}$ haloalkyl, (d) $C_{1-6}$ hydroxyalkyl, (e) $C_{1-3}$ alkoxy-$C_{1-3}$ alkyl, (f) $C_{3-6}$ cycloalkyl-$C_{1-6}$ alkyl, (g) $C_{1-6}$ alkoxy, (h) amino, (i) $C_{1-6}$ alkylamino, (j) di-$C_{1-6}$ alkylamino (k) $C_{3-6}$ cycloalkylamino, (l) phenyl-$C_{1-3}$ alkyl (m) phenyl, wherein said phenyl is optionally substituted with one to three groups independently selected in each occurrence from the group consisting of $C_{1-6}$ alkyl, $C_{1-6}$ alkoxy, halogen, $-SO_2NR^{6a}R^{6b}$ and $-NHSO_2C_{1-6}$ alkyl, (n) tetrahydropyranyl, (o) tetrahydrofuranyl, (p) cycloalkoxy optionally independently substituted with one or two halogen, hydroxy or oxo, (q) $C_{4-6}$ cycloalkylamino, (r) tetrahydropyranyl-methyl, (s) pyridinyl or (t) cyanomethyl;

$R^{6a}$ and $R^{6b}$ are independently hydrogen, $C_{1-6}$ alkyl or $C_{1-6}$ acyl;

$R^7$ is hydrogen or $C_{1-3}$ alkyl;

$R^{9a}$ and $R^{10a}$ (i) taken independently, one of $R^{9a}$ and $R^{10a}$ is hydrogen or $C_{1-6}$ alkyl and the other of $R^{9a}$ and $R^{10a}$ is selected from the group consisting of hydrogen, $C_{1-6}$ alkyl and $-C(=O)R^7$;
(ii) taken together with the nitrogen atom to which they are attached form an azetidine, pyrrolidine, piperidine or azepine ring said azetidine, pyrrolidine, piperidine or azepine ring optionally substituted with hydroxy, amino, $C_{1-3}$ alkylamine or $C_{1-3}$ dialkylamine; or,
(iii) taken together are $(CH_2)_2-X-(CH_2)_2$;

$R^{9b}$ is defined as $R^{9a}$ and $R^{10b}$ is defined as $R^{10a}$;

$R^{11}$ is hydrogen, $C_{1-6}$ alkyl or $C_{1-6}$ acyl;

X is O, $S(O)_p$ or $NR^{11}$ wherein p is an integer from 0 to 2;

Ar is phenyl optionally substituted with one to three substituents independently selected in each occurrence from the group consisting of halogen, $C_{1-6}$ alkyl, $C_{1-6}$ alkoxy, cyano and nitro; or, pharmaceutically acceptable salts thereof.

2. A compound according to claim 1 wherein
$R^1$ is selected from the group consisting of phenyl, pyridinyl and pyrimidinyl optionally substituted with $C_{1-6}$ alkyl, $C_{1-6}$ haloalkyl, $C_{1-6}$ alkoxy, hydroxy, cyano and halogen; or, pharmaceutically acceptable salts thereof.

3. A compound according to claim 2 wherein:
$R^1$ is 2,6-dimethylphenyl, 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl;
$R^2$ is A3;
$R^3$ is hydrogen;
$R^4$ is $-C(=O)R^5$ or $-SO_2R^5$; and,
Ar is phenyl optionally substituted with one to three halogens.

4. A compound according to claim 3 wherein
$R^1$ is 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl;
$R^4$ is $-SO_2R^5$; and,
$R^5$ is (a) $C_{1-6}$ alkyl, (b) $C_{3-6}$ cycloalkyl optionally substituted with one or two groups independently selected in each occurrence from the group consisting of hydroxyl, halogen, $C_{1-6}$ alkyl, $C_{1-6}$ haloalkyl and oxo, (c) phenyl, wherein said phenyl is optionally substituted with one to three groups independently selected in each occurrence from the group consisting of $C_{1-6}$ alkyl, $C_{1-6}$ alkoxyl, halogen, $-SO_2NHR^{6a}R^{6b}$ and $-NHSO_2C_{1-6}$ alkyl, or (d) optionally substituted phenyl-$C_{1-3}$ alkyl.

5. A compound according to claim 3 wherein:
$R^1$ is 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl;
$R^4$ is $-CO_2R^5$; and,
$R^5$ is (a) $C_{1-6}$ alkyl, (b) $C_{1-6}$ alkoxy, (c) $C_{1-6}$ hydroxyalkyl, (d) $C_{3-6}$ cycloalkyl optionally substituted with one or two groups independently selected in each occurrence from the group consisting of hydroxyl, halogen, $C_{1-6}$ alkyl, $C_{1-6}$ haloalkyl and oxo, or (e) $C_{1-3}$ alkoxy-$C_{1-3}$ alkyl.

6. A compound according to claim 2 wherein:
$R^1$ is 2,6-dimethylphenyl, 2,4-dimethyl-pyridin-3-yl, 2,4-dimethyl-6-cyano-pyridin-3-yl; 4,6-dimethyl-pyrimidin-5-yl or 4,6-dimethyl-2-trifluoromethyl-pyrimidin-5-yl;
$R^2$ is A1 or A2;
$R^3$ is hydrogen;
$R^4$ is $-C(=O)R^5$ or $-SO_2R^5$; and, Ar is phenyl optionally substituted with one to three halogens.

7. A compound according to claim 2 wherein:
R$^1$ is 2,6-dimethylphenyl, 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl;
R$^2$ and R$^3$ together are (CH$_2$)$_m$NR$^4$(CH$_2$)$_n$;
m and n are independently one or two;
R$^4$ is —C(=O)R$^5$ or —SO$_2$R$^5$; and,
Ar is phenyl optionally substituted with one to three halogens.

8. A compound according to claim 7 wherein:
m and n are one;
R$^4$ is —C(=O)R$^5$ or —SO$_2$R$^5$; and,
R$^5$ is (a) C$_{1-6}$ alkyl, (b) C$_{1-6}$ haloalkyl, (c) C$_{3-6}$ cycloalkyl optionally independently substituted with one or two C$_{1-6}$ alkyl, halogen, hydroxy, cyano, oxo or C$_{1-6}$ haloalkyl, (d) tetrahydropyranyl, (c) tetrahydrofuranyl.

9. A compound according to claim 2 wherein:
R$^1$ is 2,6-dimethylphenyl, 2,4-dimethyl-pyridin-3-yl, 2,4-dimethyl-6-cyano-pyridin-3-yl, 4,6-dimethyl-pyrimidin-5-yl or 4,6-dimethyl-2-trifluoromethyl-pyrimidin-5-yl;
R$^2$ and R$^3$ together are (CH$_2$)$_m$NR$^4$(CH$_2$)$_n$;
m and n are independently one or two;
R$^4$ is C$_{1-6}$ alkyl or C$_{1-6}$ haloalkyl; and,
Ar is phenyl optionally substituted with one to three halogens.

10. A pharmaceutical composition comprising a therapeutically effective quantity of a compound according to claim 1 or claim 2 and at least one pharmaceutically acceptable carrier, excipient or diluent.

11. A compound according to claim 2, wherein said compound is either a free base or a pharmaceutically acceptable acid addition salt of a compound selected from group consisting of:
4-{2-[5(4,6-Dimethyl-pyrimidine-5-carbonyl)-hexahydro-pyrrolo[3,4-c]pyrrol-2-yl]-ethyl}-4-phenyl-piperidine-1-carboxylic acid tert-butyl ester;
4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidine-1-carboxylic acid tert-butyl ester;
(5-{2-[1-Benzoyl-4-(3-fluoro-phenyl)-piperidin-4-yl]-ethyl}-hexahydro-pyrrolo[3,4-c]pyrrol-2-yl)-(4,6-dimethyl-pyrimidin-5-yl)-methanone;
{5-[2-(1-Benzoyl-4-phenyl-piperidin-4-yl)-ethyl]-hexahydro-pyrrolo[3,4-c]pyrrol-2-yl}-(4,6-dimethyl-pyrimidin-5-yl)-methanone;
1-(4-{2-[5-(4,6-Dimethyl-pyrimidine-5-carbonyl)-hexahydro-pyrrolo[3,4-c]pyrrol-2-yl]-ethyl}-4-phenyl-piperidin-1-yl)-2,2-dimethyl-propan-1-one;
1-[4-{2-[5-(4,6-Dimethyl-pyrimidine-5-carbonyl)-hexahydro-pyrro[3,4-c]pyrrol-2-yl]-ethyl}-4-(3-fluoro-phenyl)-piperidin-1-yl]-2,2-dimethyl-propan-1-one;
(4,6-Dimethyl-pyrimidin-5-yl)-(5-{2-[1-(3-fluoro-benzenesulfonyl)-4-(3-fluoro-phenyl)-piperidin-4-yl]-ethyl}-hexahydro-pyrrolo[3,4-c]pyrrol-2-yl)-methanone;
(4,6-Dimethyl-pyrimidin-5-yl)-(5-{2-[1-(3-fluoro-benzenesulfonyl)-4-phenyl-piperidin-4-yl]-ethyl}-hexahydro-pyrrolo[3,4-c]pyrrol-2-yl)-methanone;
4-(4-{2-[5-(4,6-Dimethyl-pyrimidine-5-carbonyl)-hexahydro-pyrrolo[3,4-c]pyrrol-2-yl]-ethyl}-4-phenyl-piperidine-1-carbonyl)-benzenesulfonamide;
4-(4-{2-[5-(4,6-Dimethyl-pyrimidine-5-carbonyl)-hexahydro-pyrrolo[3,4-c]pyrrol-2-yl]-ethyl}-4-phenyl-piperidine-1-carbonyl)-N-methyl-benzenesulfonamide;
4-(4-{2-[5-(4,6-Dimethyl-pyrimidine-5-carbonyl)-hexahydro-pyrrolo[3,4-]pyrrol-2-yl]-ethyl}-4-phenyl-piperidine-1-carbonyl)-N,N-dimethyl-benzenesulfonamide;
3-(4-{2-[5-(4,6-Dimethyl-pyrimidine-5-carbonyl)-hexahydro-pyrrolo[3,4-c]pyrrol-2-yl]-ethyl}-4-phenyl-piperidine-1-carbonyl)-benzenesulfonamide;
3-(4-{2-[5-(4,6-Dimethyl-pyrimidine-5-carbonyl)-hexahydro-pyrrolo[3,4-c]pyrrol-2-yl]-ethyl}-4-phenyl-piperidine-1-carbonyl)-N-methyl-benzenesulfonamide;
3-(4-{2-[5-(4,6-Dimethyl-pyrimidine-5-carbonyl)-hexahydro-pyrrolo[3,4-c]pyrrol-2-yl]-ethyl}-4-phenyl-piperidine-1-carbonyl)-N,N-dimethyl-benzenesulfonamide;
4-[4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidine-1-carbonyl]-N-methyl-benzenesulfonamide;
4-[4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidine-1-carbonyl]-N,N-dimethyl-benzenesulfonamide;
3-[4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidine-1-carbonyl]-benzenesulfonamide;
3-[4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidine-1-carbonyl]-N-methyl-benzenesulfonamide;
3-[4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidine-1-carbonyl]-N,N-dimethyl-benzenesulfonamide;
N-[4-(4-{2-[5-(4,6-Dimethyl-pyrimidine-5-carbonyl)-hexahydro-pyrrolo[3,4-c]pyrrol-2-yl]-ethyl}-4-phenyl-piperidine-1-carbonyl)-phenyl]-methanesulfonamide;
N-{4-[4-{2-[5-(4,6Dimethyl-pyrimidine-5-carbonyl)-hexahydro-pyrrolo[3,4-c]pyrrol-2-yl]-ethyl}-4-(3-fluoro-phenyl)-piperidine-1-carbonyl]-phenyl}-methanesulfonamide;
1-[4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidin-1-yl]-ethanone;
1-(4-{2-[5-(4,6-Dimethyl-pyrimidine-5-carbonyl)-hexahydro-pyrrolo[3,4-c]pyrrol-2-yl]-ethyl}-4-phenyl-piperidin-1-yl)-ethanone;
1-(4-{2-[5-(4,6-Dimethyl-pyrimidine-5-carbonyl)-hexahydro-pyrrolo[3,4-c]pyrrolo-2-yl]-ethyl}-4-phenyl-piperidin-1-yl)-2-methyl-propan-1-one;
1-[4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidin-1-yl]-2-methyl-propan-1-one;
{5-[2-(1-Cyclopropanecarbonyl-4-phenyl-piperidin-4-yl)-ethyl]-hexahydro-pyrrolo[3,4-c]pyrrol-2-yl}-(4,6-dimethyl-pyrimidin-5-yl)-methanone;
{5-[2-(1-Cyclobutanecarbonyl-4-phenyl-piperidin-4-yl)-ethyl]-hexahydro-pyrrolo[3,4-c]pyrrol-2-yl}-(4,6-dimethyl-pyrimidin-5-yl)-methanone;
{5-[2-(1-Cyclopentanecarbonyl-4-phenyl-piperidin-4-yl)-ethyl]-hexahydro-pyrrolo[3,4-c]pyrrol-2-yl}-(4,6-dimethyl-pyrimidin-5-yl)-methanone;

{5-[2-(1-Cyclohexanecarbonyl-4-phenyl-piperidin-4-yl)-ethyl]-hexahydro-pyrrolo[3,4-c]pyrrol-2-yl}-(4,6-dimethyl-pyrimidin-5-yl)-methanone;

(4,6-Dimethyl-pyrimidin-5-yl)-(5-{2-[4-phenyl-1-(tetrahydro-pyran-4-carbonyl)-piperidin-4-yl]-ethyl}-hexahydro-pyrrolo[3,4-c]pyrrol-2-yl)-methanone;

1-(4-{2-[5-(4,6-Dimethyl-pyrimidine-5-carbonyl)-hexahydro-pyrrolo[3,4-c]pyrrol-2-yl]-ethyl}-4-phenyl-piperidin-1-yl)-3,3-dimethyl-butan-1-one;

2-Cyclopentyl-1-(4-{2-[5(4,6-dimethyl-pyrimidine-5-carbonyl)-hexahydro-pyrrolo[3,4-c]pyrrol-2-yl]-ethyl}-4-phenyl-piperidin-1-yl)-ethanone;

1-(4-{2-[5-(4,6-Dimethyl-pyrimidine-5-carbonyl)-hexahydro-pyrrolo[3,4-c]pyrrol-2-yl]-ethyl}-4-phenyl-piperidin-1-yl)-3,3,3-trifluoro-propan-1-one;

(5-{2-[1-Cyclopropanecarbonyl-4-(3-fluoro-phenyl)-piperidin-4-yl]-ethyl}-hexahydro-pyrrolo[3,4-c]pyrrol-2-yl)-(4,6-dimethyl-pyrimidin-5-yl)-methanone;

(5-{2-[1-Cyclobutanecarbonyl-4-(3-fluoro-phenyl)-piperidin-4-yl]-ethyl}-hexahydro-pyrrolo[3,4-c]pyrrol-2-yl)-(4,6-dimethyl-pyrimidin-5-yl)-methanone;

(5-{2-[1-Cyclopentanecarbonyl-4-(3-fluoro-phenyl)-piperidin-4-yl]-ethyl}-hexahydro-pyrrolo[3,4-c]pyrrol-2-yl)-(4,6-dimethyl-pyrimidin-5-yl)-methanone;

(5-{2-[1-Cyclohexanecarbonyl-4-(3-fluoro-phenyl)-piperidin-4-yl]-ethyl}-hexahydro-pyrrolo[3,4-c]pyrrol-2-yl)-(4,6-dimethyl-pyrimidin-5-yl)-methanone;

(4,6-Dimethyl-pyrimidin-5-yl)-(5-{2-[4-(3-fluoro-phenyl)-1-(tetrahydro-pyran-4-carbonyl)-piperidin-4-yl]-ethyl}-hexahydro-pyrrolo[3,4-c]pyrrol-2-yl)-methanone;

1-[4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidin-1-yl]-3,3-dimethyl-butan-1-one;

2-Cyclopentyl-1-[4-{2-[5-(4,6-dimethyl-pyrimidine-5-carbonyl)-hexahydro-pyrrolo[3,4-c]pyrrol-2-yl]ethyl}-4-(3-fluoro-phenyl)-piperidin-1-yl]-ethanone;

1-[4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidin-1-yl]-3,3,3-trifluoro-propan-1-one;

(4,6-Dimethyl-pyrimidin-5-yl)-(5-{2-[4-(3-fluoro-phenyl)-1-(1-methyl-cyclopropanecarbonyl)-piperidin-4-yl]-ethyl}-hexahydro-pyrrolo[3,4-c]pyrrol-2-yl)-methanone;

(4,6-Dimethyl-pyrimidin-5-yl)-(5-{2-[4-(3-fluoro-phenyl)-1-(1-trifluoromethyl-cyclopropanecarbonyl)-piperidin-4-yl]-ethyl}-hexahydro-pyrrolo[3,4-c]pyrrol-2-yl)-methanone;

1-[4-{2-[5-(4,6-Dimethyl-pyrimidine-5-carbonyl)-hexahydro-pyrrolo[3,4-c]pyrrol-2-yl]-ethyl}-4-(3-fluoro-phenyl)-piperidin-1-yl]-3-hydroxy-2,2-dimethyl-propan-1-one;

{5-[2-(1-Cyclopentanecarbonyl-3-phenyl-azetidin-3-yl)-ethyl]-hexahydro-pyrrolo[3,4-c]pyrrol-2-yl}-(4,6-dimethyl-pyrimidin-5-yl)-methanone;

{5-[2-(1-Cyclopentanecarbonyl-3-phenyl-pyrrolidin-3-yl)-ethyl]-hexahydro-pyrrolo[3,4-c]pyrrol-2-yl}-(4,6-dimethyl-pyrimidin-5-yl)-methanone;

2-Cyclopentyl-1-(3-{2-[5-(4,6-dimethyl-pyrimidine-5-carbonyl)-hexahydro-pyrrolo[3,4-c]pyrrol-2-yl]-ethyl}-3-phenyl-pyrrolidin-1-yl)-ethanone;

1-(3-{2-[5-(4,6-Dimethyl-pyrimidine-5-carbonyl)-hexahydro-pyrrolo[3,4-c]pyrrol-2-yl]-ethyl}-3-phenyl-pyrrolidin-1-yl)-ethanone;

1-(3-{2-[5-(4,6-Dimethyl-pyrimidine-5-carbonyl)-hexahydro-pyrrolo[3,4-c]pyrrol-2-yl]-ethyl}-3-phenyl-pyrrolidin-1-yl)-2,2-dimethyl-propan-1-one;

5-{5-[2-(1-Cyclopentanecarbonyl-3-phenyl-pyrrolidin-3-yl)-ethyl]-hexahydro-pyrrolo[3,4-c]pyrrole-2-carbonyl}-4,6-dimethyl-pyridine-2-carbonitrile;

5-(5-{2-[1-(2-Cyclopentyl-acetyl)-3-phenyl-pyrrolidin-3-yl]-ethyl}-hexahydro-pyrrolo[3,4-c]pyrrole-2-carbonyl)-4,6-dimethyl-pyridine-2-carbonitrile;

5-{5-[2-(1-Acetyl-3-phenyl-pyrrolidin-3-yl)-ethyl]-hexahydro-pyrrolo[3,4-c]pyrrole-2-carbonyl}-4,6-dimethyl-pyridine-2-carbonitrile;

5-(5-{2-[1-(2,2-Dimethyl-propionyl)-3-phenyl-pyrrolidin-3-yl]-ethyl}-hexahydro-pyrrolo[3,4-c]pyrrole-2-carbonyl)-4,6-dimethyl-pyridine-2-carbonitrile;

5-(5-{2-[1-(3,3-Difluoro-cyclobutanecarbonyl)-3-phenyl-pyrrolidin-3-yl]-ethyl}-hexahydro-pyrrolo[3,4-c]pyrrole-2-carbonyl)-4,6-dimethyl-pyridine-2-carbonitrile;

1-[3-(2-{5-[3,5-Dimethyl-1-(5-trifluoromethyl-pyridin-2-yl)-1H-pyrazole-4-carbonyl]-hexahydro-pyrrolo[3,4-c]pyrrol-2-yl}-ethyl)-3-phenyl-pyrrolidin-1-yl]-ethanone;

{5-[2-(1-Cyclopentanecarbonyl-3-phenyl-pyrrolidin-3-yl)-ethyl]-hexahydro-pyrrolo[3,4-c]pyrrol-2-yl}-[3,5-dimethyl-1-(5-trifluoromethyl-pyridin-2-yl)-1H-pyrazol-4-yl]-methanone;

(5-{2-[1-(3,3-Difluoro-cyclobutanecarbonyl)-3-phenyl-pyrrolidin-3-yl]-ethyl}-hexahydro-pyrrolo[3,4-c]pyrrol-2-yl)-[3,5-dimethyl-1-(5-trifluoromethyl-pyridin-2-yl)-1H-pyrazol-4-yl]-methanone;

5-(5-{2-[1-(2,2-Dimethyl-propionyl)-4-(3-fluoro-phenyl)-piperidin-4-yl]-ethyl}-hexahydro-pyrrolo[3,4-c]pyrrole-2-carbonyl)-4,6-dimethyl-pyridine-2-carbonitrile;

3-{3-[5-(4,6-Dimethyl-pyrimidine-5-carbonyl)-hexahydro-pyrrolo[3,4-c]pyrrol-2-yl]-1-phenyl-propyl}-azetidine-1-carboxylic acid tert-butyl ester;

{5-[3-(1-Cyclopentanecarbonyl-azetidin-3-yl)-3-phenyl-propyl]-hexahydro-pyrrolo[3,4-c]pyrrol-2-yl}-(4,6-dimethyl-pyrimidin-5-yl)-methanone;

(4,6-Dimethyl-pyrimidin-5-yl)-(5-{3-phenyl-3-[1-(2,2,2-trifluoro-ethyl)-azetidin-3-yl]-propyl}-hexahydro-pyrrolo[3,4-c]pyrrol-2-yl)-methanone;

1-(3-{3-[5-(4,6-Dimethyl-pyrimidine-5-carbonyl)-hexahydro-pyrrolo[3,4-c]pyrrol-2-yl]-1-phenyl-propyl}-azetidin-1-yl)-3-methyl-butan-1-one;

(5-{3-[1-(3,3-Difluoro-cyclobutanecarbonyl)-azetidin-3-yl]-3-phenyl-propyl}-hexahydro-pyrrolo[3,4-c]pyrrol-2-yl)-(4,6-dimethyl-pyrimidin-5-yl)-methanone;

(4,6-Dimethyl-pyrimidin-5-yl)-(5-{3-phenyl-3-[1-(propane-2-sulfonyl)-azetidin-3-yl]-propyl}-hexahydro-pyrrolo[3,4-c]pyrrol-2-yl)-methanone;

(4,6-Dimethyl-pyrimidin-5-yl)-(5-{3-phenyl-3-[1-(2,2,2-trifluoro-ethyl)-piperidin-4-yl]-propyl}-hexahydro-pyrrolo[3,4-c]pyrrol-2-yl)-methanone;

4-{3-[5-(4,6-Dimethyl-pyrimidine-5-carbonyl)-hexahydro-pyrrolo[3,4-c]pyrrol-2-yl]-1-phenyl-propyl}-piperidine-1-carboxylic acid tert-butylamide;

4-{3-[5-(4,6-Dimethyl-pyrimidine-5-carbonyl)-hexahydro-pyrrolol[3,4-c]pyrrol-2-yl]-1-phenyl-propyl}-piperidine-1-carboxylic acid isopropylamide;

4-{3-[5-(4,6-Dimethyl-pyrimidine-5-carbonyl)-hexahydro-pyrrolo[3,4-c]pyrrol-2-yl]-1-phenyl-propyl}-piperidine-1-carboxylic acid ethylamide;

4-{3-[5-(4,6-Dimethyl-pyrimidine-5-carbonyl)-hexahydro-pyrrolo[3,4-c]pyrrol-2-yl]-1-phenyl-propyl}-piperidine-1-carboxylic acid cyclopentylamide;

4-{3-[5-(4,6-Dimethyl-pyrimidine-5-carbonyl)-hexahydro-pyrrolo[3,4-c]pyrrol-2-yl]-1-phenyl-propyl}-piperidine-1-carboxylic acid 3-hydroxy-cyclopentyl ester;
4-{3-[5-(4,6-Dimethyl-pyrimidine-5-carbonyl)-hexahydro-pyrrolo[3,4-c]pyrrol-2-yl]-1-phenyl-propyl}-piperidine-1-carboxylic acid methyl ester;
{5-[3-(1-Benzenesulfonyl-piperidin-4-yl)-3-phenyl-propyl]-hexahydro-pyrrolo[3,4-c]pyrrol-2-yl}-(4,6-dimethyl-pyrimidin-5-yl)-methanone;
(4,6-Dimethyl-pyrimidin-5-yl)-(5-{3-phenyl-3-[1-(propane-2-sulfonyl)-piperidin-4-yl]-propyl}-hexahydro-pyrrolo[3,4-c]pyrrol-2-yl)-methanone;
(4,6-Dimethyl-pyrimidin-5-yl)-{5-[3-phenyl-3-(1-phenylmethanesulfonyl-piperidin-4-yl)-propyl]-hexahydro-pyrrolo[3,4-c]pyrrol-2-yl}-methanone;
(4,6-Dimethyl-pyrimidin-5-yl)-{5-[3-(1-ethanesulfonyl-piperidin-4-yl)-3-phenyl-propyl]-hexahydro-pyrrolo[3,4-c]pyrrol-2-yl}-methanone;
(4,6-Dimethyl-pyrimidin-5-yl)-{5-[3-(1-methanesulfonyl-piperidin-4-yl)-3-phenyl-propyl]-hexahydro-pyrrolo[3,4-c]pyrrol-2-yl}-methanone;
1-(4-{3-[5-(4,6-Dimethyl-pyrimidine-5-carbonyl)-hexahydro-pyrrolo[3,4-c]pyrrol-2-yl]-1-phenyl-propyl}-piperidin-1-yl)-propan-1-one;
1-(4-{3-[5-(4,6-Dimethyl-pyrimidine-5-carbonyl)-hexahydro-pyrrolo[3,4-c]pyrrol-2-yl]-1-phenyl-propyl}-piperidin-1-yl)-3-methyl-butan-1-one;
1-(4-{3-[5-(4,6-Dimethyl-pyrimidine-5-carbonyl)-hexahydro-pyrrolo[3,4-c]pyrrol-2-yl]-1-phenyl-propyl}-piperidin-1-yl)-2,2-dimethyl-propan-1-one;
1-(4-{3-[5-(4,6-Dimethyl-pyrimidine-5-carbonyl)-hexahydro-pyrrolo[3,4-c]pyrrol-2-yl]-1-phenyl-propyl}-piperidin-1-yl)-2-methoxy-ethanone;
(4,6-Dimethyl-pyrimidin-5-yl)-{5-[3-(1-methanesulfonyl-azetidin-3-yl)-3-phenyl-propyl]-hexahydro-pyrrolo[3,4-c]pyrrol-2-yl}-methanone;
{5-[3-(1-Cyclopentanesulfonyl-azetidin-3-yl)-3-phenyl-propyl]-hexahydro-pyrrolo[3,4-c]pyrrol-2-yl}-(4,6-dimethyl-pyrimidin-5-yl)-methanone;
2-Cyclopentyl-1-(4-{3-[5-(4,6-dimethyl-pyrimidine-5-carbonyl)-hexahydro-pyrrolo[3,4-c]pyrrol-2-yl]-1-phenyl-propyl}-piperidin-1-yl)-ethanone;
{5-[3-(1-Cyclopentanesulfonyl-piperidin-4-yl)-3-phenyl-propyl]-hexahydro-pyrrolo[3,4-c]pyrrol-2-yl}-(4,6-dimethyl-pyrimidin-5-yl)-methanone;
1-(4-{3-[5-(4,6-Dimethyl-pyrimidine-5-carbonyl)-hexahydro-pyrrolo[3,4-c]pyrrol-2-yl]-1-phenyl-propyl}-piperidin-1-yl)-2-methyl-propan-1-one;
{5-[3-(1-Cyclopropanesulfonyl-azetidin-3-yl)-3-phenyl-propyl]-hexahydro-pyrrolo[3,4-c]pyrrol-2-yl}-(4,6-dimethyl-pyrimidin-5-yl)-methanone;
{5-[3-(1-Cyclopropanesulfonyl-piperidin-4-yl)-3-phenyl-propyl]-hexahydro-pyrrolo[3,4-c]pyrrol-2-yl}-(4,6-dimethyl-pyrimidin-5-yl)-methanone;
(5-{3-[1-(2,2-Difluoro-ethyl)-piperidin-4-yl]-3-phenyl-propyl}-hexahydro-pyrrolo[3,4-c]pyrrol-2-yl)-(4,6-dimethyl-pyrimidin-5-yl)-methanone;
(4,6-Dimethyl-pyrimidin-5-yl)-(5-{2-[1-(3-fluoro-benzenesulfonyl)-3-phenyl-azetidin-3-yl]-ethyl}-hexahydro-pyrrolo[3,4-c]pyrrol-2-yl)-methanone;
(4,6-Dimethyl-pyrimidin-5-yl)-(5-{2-[1-(3-fluoro-benzoyl)-3-phenyl-azetidin-3-yl]-ethyl}-hexahydro-pyrrolo[3,4-c]pyrrol-2-yl)-methanone;
(4,6-Dimethyl-pyrimidin-5-yl)-(5-{2-[3-phenyl-1-(tetrahydro-pyran-4-carbonyl)-azetidin-3-yl]-ethyl}-hexahydro-pyrrolo[3,4-c]pyrrol-2-yl)-methanone;
(4,6-Dimethyl-pyrimidin-5-yl)-(5-{2-[3-phenyl-1-(tetrahydro-furan-3-carbonyl)-azetidin-3-yl]-ethyl}-hexahydro-pyrrolo[3,4-c]pyrrol-2-yl)-methanone;
2-Cyclopentyl-1-(3-{2-[5-(4,6-dimethyl-pyrimidine-5-carbonyl)-hexahydro-pyrrolo[3,4-c]pyrrol-2-yl]-ethyl}-3-phenyl-azetidin-1-yl)-ethanone;
1-(3-{2-[5-(4,6-Dimethyl-pyrimidine-5-carbonyl)-hexahydro-pyrrolo[3,4-c]pyrrol-2-yl]-ethyl}-3-phenyl-azetidin-1-yl)-2,2-dimethyl-propan-1-one;
1-(3-{2-[5-(4,6-Dimethyl-pyrimidine-5-carbonyl)-hexahydro-pyrrolo[3,4-c]pyrrol-2-yl]-ethyl}-3-phenyl-azetidin-1-yl)-3,3,3-trifluoro-propan-1-one;
(5-{2-[1-(3,3-Difluoro-cyclobutanecarbonyl)-3-phenyl-azetidin-3-yl]-ethyl}-hexahydro-pyrrolo[3,4-c]pyrrol-2-yl)-(4,6-dimethyl-pyrimidin-5-yl)-methanone;
(4,6-Dimethyl-pyrimidin-5-yl)-(5-{2-[1-(4-hydroxy-cyclohexanecarbonyl)-3-phenyl-azetidin-3-yl]-ethyl}-hexahydro-pyrrolo[3,4-c]pyrrol-2-yl)-methanone;
1-(3-{2-[5-(4,6-Dimethyl-pyrimidine-5-carbonyl)-hexahydro-pyrrolo[3,4-c]pyrrol-2-yl]-ethyl}-3-phenyl-azetidin-1-yl)-2-(tetrahydro-pyran-4-yl)-ethanone;
(4,6-Dimethyl-pyrimidin-5-yl)-(5-{2-[3-phenyl-1-(tetrahydro-furan-2-carbonyl)-azetidin-3-yl]-ethyl}-hexahydro-pyrrolo[3,4-c]pyrrol-2-yl)-methanone;
(4,6-Dimethyl-pyrimidin-5-yl)-(5-{2-[1-(1-methyl-cyclopropanecarbonyl)-3-phenyl-azetidin-3-yl]-ethyl}-hexahydro-pyrrolo[3,4-c]pyrrol-2-yl)-methanone;
1-(3-{2-[5-(4,6-Dimethyl-pyrimidine-5-carbonyl)-hexahydro-pyrrolor[3,4-c]pyrrol-2-yl]-ethyl}-3-phenyl-azetidine-1-carbonyl)-cyclopropanecarbonitrile;
(3-{2-[5-(4,6-Dimethyl-pyrimidine-5-carbonyl)-hexahydro-pyrrolo[3,4-c]pyrrol-2-yl]-ethyl}-3-phenyl-azetidin-1-yl)-(1-trifluoromethyl-cyclopropyl)-methanone;
1-(3-{2-[5-(4,6-Dimethyl-pyrimidine-5-carbonyl)-hexahydro-pyrrolo[3,4-c]pyrrol-2-yl]-ethyl}-3-phenyl-azetidin-1-yl)-3-hydroxy-2,2-dimethyl-propan-1-one;
(4,6-Dimethyl-pyrimidin-5-yl)-(5-{2-[1-(1-hydroxy-cyclopropanecarbonyl)-3-phenyl-azetidin-3-yl]-ethyl}-hexahydro-pyrrolo[3,4-c]pyrrol-2-yl)-methanone;
3-(3-{2-[5-(4,6-Dimethyl-pyrimidine-5-carbonyl)-hexahydro-pyrrolo[3,4-c]pyrrol-2-yl]-ethyl}-3-phenyl-azetidine-1-carbonyl)-cyclopentanone;
(4,6-Dimethyl-pyrimidin-5-yl)-(5-{2-[3-phenyl-1-(propane-2-sulfonyl)-azetidin-3-yl]-ethyl}-hexahydro-pyrrolo[3,4-c]pyrrol-2-yl)-methanone;
{5-[2-(1-Cyclopropanesulfonyl-3-phenyl-azetidin-3-yl)-ethyl]-hexahydro-pyrrolo[3,4-c]pyrrol-2-yl}-(4,6-dimethyl-pyrimidin-5-yl)-methanone;
(4,6-Dimethyl-pyrimidin-5-yl)-(5-{2-[1-(3-hydroxy-cyclopentanecarbonyl)-3-phenyl-azetidin-3-yl]-ethyl}-hexahydro-pyrrolo[3,4-c]pyrrol-2-yl)-methanone;
{5-[2-(1-Cyclopentanesulfonyl-3-phenyl-azetidin-3-yl)-ethyl]-hexahydro-pyrrolo[3,4-c]pyrrol-2-yl}-(4,6-dimethyl-pyrimidin-5-yl)-methanone;
1-(3-{3-[5-(4,6-Dimethyl-pyrimidine-5-carbonyl)-hexahydro-pyrrolo[3,4-c]pyrrol-2-yl]-1-phenyl-propyl}-azetidin-1-yl)-2-methyl-propan-1-one;
(4,6-Dimethyl-pyrimidin-5-yl)-(5-{3-[1-(2-methyl-propane-1-sulfonyl)-azetidin-3-yl]-3-phenyl-propyl}-hexahydro-pyrrolo[3,4-c]pyrrol-2-yl)-methanone;
(4,6-Dimethyl-pyrimidin-5-yl)-(5-{2-[3-phenyl-1-(2,2,2-trifluoro-ethyl)-azetidin-3-yl]-ethyl}-hexahydro-pyrrolo[3,4-c]pyrrol-2-yl)-methanone;
(5-{2-[1-(2,2-Difluoro-ethyl)-3-phenyl-azetidin-3-yl]-ethyl}-hexahydro-pyrrolo[3,4-c]pyrrol-2-yl)-(4,6-dimethyl-pyrimidin-5-yl)-methanone;

(5-{2-[1-(4,4-Difluoro-cyclohexanecarbonyl)-3-phenyl-azetidin-3-yl]-ethyl}-hexahydro-pyrrolo[3,4-c]pyrrol-2-yl)-(4,6-dimethyl-pyrimidin-5-yl)-methanone;

(3-{2-[5-(4,6-Dimethyl-2-trifluoromethyl-pyrimidine-5-carbonyl)-hexahydro-pyrrolo[3,4-c]pyrrol-2-yl]-ethyl}-3-phenyl-azetidin-1-yl)-(tetrahydro-furan-3-yl)-methanone (5-{2-[1-(3,5-Difluoro-benzoyl)-3-phenyl-azetidin-3-yl]-ethyl}-hexahydro-pyrrolo[3,4-c]pyrrol-2-yl)-(4,6-dimethyl-pyrimidin-5-yl)-methanone;

(2,4-Dimethyl-pyridin-3-yl)-(5-{2-[3-phenyl-1-(tetrahydro-furan-3-carbonyl)-azetidin-3-yl]-ethyl}-hexahydro-pyrrolo[3,4-c]pyrrol-2-yl)-methanone;

1-(4-{3-[5-(4,6-Dimethyl-pyrimidine-5-carbonyl)-hexahydro-pyrrolo[3,4-c]pyrrol-2-yl]-1-phenyl-propyl}-piperidin-1-yl)-2,2,2-trifluoro-ethanone;

4,6-Dimethyl-5-(5-{2-[3-phenyl-1-(tetrahydro-furan-3-carbonyl)-azetidin-3-yl]-ethyl}-hexahydro-pyrrolo[3,4-c]pyrrole-2-carbonyl)-pyridine-2-carbonitrile;

(5-{2-[1-(4,4-Difluoro-cyclohexanecarbonyl)-3-phenyl-azetidin-3-yl]-ethyl}-hexahydro-pyrrolo[3,4-c]pyrrol-2-yl)-(4,6-dimethyl-2-trifluoromethyl-pyrimidin-5-yl)-methanone;

(5-{2-[1-(3,3-Difluoro-cyclobutanecarbonyl)-3-phenyl-azetidin-3-yl]-ethyl}-hexahydro-pyrrolo[3,4-c]pyrrol-2-yl)-(4,6-dimethyl-2-trifluoromethyl-pyrimidin-5-yl)-methanone;

(4,6-Dimethyl-pyrimidin-5-yl)-(5-{3-phenyl-3-[1-(2,2,2-trifluoro-ethanesulfonyl)-piperidin-4-yl]-propyl}-hexahydro-pyrrolo[3,4-c]pyrrol-2-yl)-methanone;

5-{5-[3-(1-Methanesulfonyl-piperidin-4-yl)-3-phenyl-propyl]-hexahydro-pyrrolo[3,4-c]pyrrole-2-carbonyl}-4,6-dimethyl-pyridine-2-carbonitrile;

5-{5-[3-(1-Cyclopropanesulfonyl-azetidin-3-yl)-3-phenyl-propyl]-hexahydro-pyrrolo[3,4-c]pyrrole-2-carbonyl}-4,6-dimethyl-pyridine-2-carbonitrile;

5-{5-[3-(1-Cyclopentanesulfonyl-azetidin-3-yl)-3-phenyl-propyl]-hexahydro-pyrrolo[3,4-c]pyrrole-2-carbonyl}-4,6-dimethyl-pyridine-2-carbonitrile;

(4,4-Difluoro-cyclohexyl)-(3-{2-[5-(2,4-dimethyl-pyridine-3-carbonyl)-hexahydro-pyrrolo[3,4-c]pyrrol-2-yl]-ethyl}-3-phenyl-azetidin-1yl)-methanone;

(3,3-Difluoro-cyclobutyl)-(3-{2-[5-(2,4-dimethyl-pyridine-3-carbonyl)-hexahydro-pyrrolo[3,4-c]pyrrol-2-yl]-ethyl}-3-phenyl-azetidin-1-yl)-methanone;

(5-{2-[3-(3-Chloro-phenyl)-1-(4,4-difluoro-cyclohexanecarbonyl)-azetidin-3-yl]-ethyl}-hexahydro-pyrrolo[3,4-c]pyrrol-2-yl)-(4,6-dimethyl-pyrimidin-5-yl)-methanone;

(5-{2-[3-(3-Chloro-phenyl)-1-(3,3-difluoro-cyclobutanecarbonyl)-azetidin-3-yl]-ethyl}-hexahydro-pyrrolo[3,4-c]pyrrol-2-yl)-(4,6-dimethyl-pyrimidin-5-yl)-methanone;

{5-[3-1-(2,2-Difluoro-ethyl)-piperidin-4-yl]-3-(3-fluoro-phenyl)-propyl]-hexahydro-pyrrolo[3,4-c]pyrrol-2-yl}-(4,6-dimethyl-pyrimidin-5-yl)-methanone;

(4,6-Dimethyl-pyrimidin-5-yl)-{5-[3-[1-(3-fluoro-benzenesulfonyl)-azetidin-3-yl]-3-(3-fluoro-phenyl)-propyl]-hexahydro-pyrrolo[3,4-c]pyrrol-2-yl}-methanone;

{5-[3-(1-Cyclopentanesulfonyl-azetidin-3-yl)-3-(3-fluoro-phenyl)-propyl]-hexahydro-pyrrolo[3,4-c]pyrrol-2-yl}-(4,6-dimethyl-pyrimidin-5-yl)-methanone;

{5-[3-(1-Cyclopropanesulfonyl-azetidin-3-yl)-3-(3-fluoro-phenyl)-propyl]-hexahydro-pyrrolo[3,4-c]pyrrol-2-yl}-(4,6-dimethyl-pyrimidin-5-yl)-methanone;

(4,6-Dimethyl-pyrimidin-5-yl)-{5-[3-(3-fluoro-phenyl)-3-(1-methanesulfonyl-piperidin-4-yl)-propyl]-hexahydro-pyrrolo[3,4-c]pyrrol-2-yl}-methanone;

5-(5-{2-[1-(4,4-Difluoro-cyclohexanecarbonyl)-3-phenyl-azetidin-3-yl]-ethyl}-hexahydro-pyrrolo[3,4-c]pyrrole-2-carbonyl)-4,6-dimethyl-pyridine-2-carbonitrile;

5-(5-{2-[1-(3,3-Difluoro-cyclobutanecarbonyl)-3-phenyl-azetidin-3-yl]-ethyl}-hexahydro-pyrrolo[3,4-c]pyrrole-2-carbonyl)-4,6-dimethyl-pyridine-2-carbonitrile;

(5-{2-[1-(4,4-Difluoro-cyclohexanecarbonyl)-3-phenyl-azetidin-3-yl]-ethyl}-hexahydro-pyrrolo[3,4-c]pyrrol-2-yl)-(2,4-dimethyl-6-trifluoromethyl-pyridin-3-yl)-methanone;

(5-{2-[1-(3,3-Difluoro-cyclobutanecarbonyl)-3-phenyl-azetidin-3-yl]-ethyl}-hexahydro-pyrrolo[3,4-c]pyrrol-2-yl)-(2,4-dimethyl-6-trifluoromethyl-pyridin-3-yl)-methanone;

5-(5-{2-[1-(4,4-Difluoro-cyclohexanecarbonyl)-3-phenyl-azetidin-3-yl]-ethyl}-hexahydro-pyrrolo[3,4-c]pyrrole-2-carbonyl)-4,6-dimethyl-pyran-2-one;

(4,6-Dimethyl-pyrimidin-5-yl)-(5-{3-(3-fluoro-phenyl)-3-[1-(pyridine-2-sulfonyl)-piperidin-4-yl]-propyl}-hexahydro-pyrrolo[3,4-c]pyrrol-2-yl)-methanone;

(4,6-Dimethyl-pyrimidin-5-yl)-(5-{3-(3-fluoro-phenyl)-3-[1-(pyridine-2-sulfonyl)-azetidin-3-yl]-propyl}-hexahydro-pyrrolo[3,4-c]pyrrol-2-yl)-methanone;

3-[3-[5-(4,6-Dimethyl-pyrimidine-5-carbonyl)-hexahydro-pyrrolo[3,4-c]pyrrol-2-yl]-1-(3-fluoro-phenyl)-propyl]-azetidine-1-sulfonic acid dimethylamide;

4-[3-[5-(4,6-Dimethyl-pyrimidine-5-carbonyl)-hexahydro-pyrrolo[3,4-c]pyrrol-2-yl]-1-(3-fluoro-phenyl)-propyl]-piperidine-1-sulfonic acid dimethylamide;

(4,6-Dimethyl-pyrimidin-5-yl)-{5-[(R)-3-(3-fluoro-phenyl)-3-(1-methanesulfonyl-piperidin-4-yl)-propyl]-hexahydro-pyrrolo[3,4-c]pyrrol-2-yl}-methanone;

(4,6-Dimethyl-pyrimidin-5-yl)-{5-[(S)-3-(3-fluoro-phenyl)-3-(1-methanesulfonyl-piperidin-4-yl)-propyl]-hexahydro-pyrrolo[3,4-c]pyrrol-2-yl}-methanone;

{3-[3-[5-(4,6-Dimethyl-pyrimidine-5-carbonyl)-hexahydro-pyrrolo[3,4-c]pyrrol-2-yl]-1-(3-fluoro-phenyl)-propyl]-azetidin-1-yl}-acetonitrile;

5-{5-[3-(1-Acetyl-azetidin-3-yl)-3-phenyl-propyl]-hexahydro-pyrrolo[3,4-c]pyrrole-2-carbonyl}-4,6-dimethyl-pyridine-2-carbonitrile; and, (4-{3-[5-(4,6-Dimethyl-pyrimidine-5-carbonyl)-hexahydro-pyrrolo[3,4-c]pyrrol-2-yl]-1-phenyl-propyl}-piperidin-1 -yl)-acetonitrile.

\* \* \* \* \*